(12) United States Patent
Nishimae et al.

(10) Patent No.: US 9,365,515 B2
(45) Date of Patent: Jun. 14, 2016

(54) OXIME ESTER PHOTOINITIATORS

(71) Applicant: BASF SE, Ludwigshafen (DE)

(72) Inventors: Yuichi Nishimae, Ibaraki (JP);
Hisatoshi Kura, Takarazuka (JP);
Kazuhiko Kunimoto, Kawanishi (JP);
Ryuhei Yamagami, Osaka (JP); Keita Tanaka, Hyogo (JP)

(73) Assignee: BASF SE, Ludwigshafen (DE)

( * ) Notice: Subject to any disclaimer, the term of this patent is extended or adjusted under 35 U.S.C. 154(b) by 87 days.

(21) Appl. No.: 14/361,113

(22) PCT Filed: Dec. 3, 2012

(86) PCT No.: PCT/EP2012/074190
§ 371 (c)(1),
(2) Date: May 28, 2014

(87) PCT Pub. No.: WO2013/083505
PCT Pub. Date: Jun. 13, 2013

(65) Prior Publication Data
US 2014/0334027 A1  Nov. 13, 2014

Related U.S. Application Data

(60) Provisional application No. 61/567,662, filed on Dec. 7, 2011.

(30) Foreign Application Priority Data

Dec. 7, 2011  (EP) .................................... 11192366

(51) Int. Cl.
| | | |
|---|---|---|
| *C07D 209/00* | (2006.01) | |
| *G03F 7/031* | (2006.01) | |
| *C07D 209/80* | (2006.01) | |
| *G03F 7/00* | (2006.01) | |
| *C07D 403/12* | (2006.01) | |
| *C07D 209/86* | (2006.01) | |
| *C07D 409/04* | (2006.01) | |
| *C07D 409/14* | (2006.01) | |
| *C08F 2/50* | (2006.01) | |
| *G02B 5/20* | (2006.01) | |
| *G03F 7/20* | (2006.01) | |

(52) U.S. Cl.
CPC ............ *C07D 209/80* (2013.01); *C07D 209/86* (2013.01); *C07D 403/12* (2013.01); CPC ........ *C07D409/04* (2013.01); *C07D 409/14* (2013.01); *C08F 2/50* (2013.01); *G02B 5/201* (2013.01); *G03F 7/0007* (2013.01); *G03F 7/20* (2013.01)

(58) Field of Classification Search
CPC .. C07D 403/12; C07D 209/86; C07D 409/14; C07D 209/80; C07D 409/04; G02B 5/201; G03F 7/0007; G03F 7/20; G03F 7/031; C08F 2/50

USPC ............ 430/7, 325, 281.1, 287.1; 522/14, 36, 522/39
See application file for complete search history.

(56) References Cited

U.S. PATENT DOCUMENTS

| | | |
|---|---|---|
| 626,796 A | 6/1899 | Plummer |
| 3,579,339 A | 5/1971 | Chang et al. |
| 4,139,391 A | 2/1979 | Ikeda et al. |
| 4,575,330 A | 3/1986 | Hull |
| 4,622,286 A | 11/1986 | Sheets |
| 4,950,581 A | 8/1990 | Koike et al. |
| 5,013,768 A | 5/1991 | Kiriyama et al. |
| 5,153,095 A | 10/1992 | Kawamura et al. |
| 5,368,976 A | 11/1994 | Tajima et al. |
| 5,376,459 A | 12/1994 | Christner et al. |
| 5,650,233 A | 7/1997 | Miyake et al. |
| 5,650,263 A | 7/1997 | Wakata et al. |
| 5,677,385 A | 10/1997 | Miyake et al. |
| 5,719,008 A | 2/1998 | Hozumi et al. |
| 5,800,952 A | 9/1998 | Urano et al. |
| 5,821,016 A | 10/1998 | Satoh et al. |
| 5,840,465 A | 11/1998 | Kakinuma et al. |
| 5,847,015 A | 12/1998 | Tajima et al. |
| 5,853,446 A | 12/1998 | Carre et al. |
| 5,863,678 A | 1/1999 | Urano et al. |
| 5,866,298 A | 2/1999 | Iwamoto et al. |
| 5,879,855 A | 3/1999 | Schädeli et al. |
| 5,882,843 A | 3/1999 | Kudo et al. |
| 5,969,867 A | 10/1999 | Fukushima et al. |
| 8,349,548 B2 | 1/2013 | Matsumoto et al. |
| 8,507,725 B2 | 8/2013 | Matsumoto et al. |
| 8,507,726 B2 | 8/2013 | Studer et al. |
| 8,524,425 B2 | 9/2013 | Matsumoto et al. |
| 8,586,268 B2 | 11/2013 | Matsumoto et al. |
| 2009/0087759 A1 | 4/2009 | Matsumoto et al. |
| 2009/0292039 A1 | 11/2009 | Sewamoto et al. |
| 2010/0136491 A1 | 6/2010 | Matsumoto et al. |
| 2010/0145068 A1* | 6/2010 | Lee ................ C07C 259/06 548/444 |
| 2010/0210749 A1* | 8/2010 | Taguchi ............... C07D 209/86 522/34 |
| 2011/0134554 A1 | 6/2011 | Matsumoto et al. |
| 2013/0188270 A1 | 7/2013 | Nishimae et al. |

FOREIGN PATENT DOCUMENTS

| | | |
|---|---|---|
| DE | 2 308 830 | 8/1974 |
| DE | 29 36 039 A1 | 4/1981 |
| DE | 40 13 358 A1 | 10/1991 |
| DE | 42 28 514 A1 | 3/1994 |
| DE | 197 00 064 A1 | 7/1997 |
| EP | 0 007 086 A1 | 1/1980 |
| EP | 0 012 339 A1 | 6/1980 |
| EP | 0 033 896 A1 | 8/1981 |
| EP | 0 041 125 A1 | 12/1981 |
| EP | 0 126 541 A1 | 11/1984 |
| EP | 0 320 264 A2 | 6/1989 |
| EP | 0 339 841 A2 | 11/1989 |
| EP | 0 438 123 A2 | 7/1991 |
| EP | 0 441 232 A2 | 8/1991 |
| EP | 0 445 624 A2 | 9/1991 |
| EP | 0 497 531 A2 | 8/1992 |
| EP | 0 511 403 A1 | 11/1992 |
| EP | 0 624 826 A1 | 11/1994 |
| EP | 0 636 669 A2 | 2/1995 |
| EP | 0 678 534 A1 | 10/1995 |
| EP | 0 706 091 A1 | 4/1996 |
| EP | 0 780 729 A1 | 6/1997 |

| | | | |
|---|---|---|---|
| EP | 0 863 534 A2 | 9/1998 |
| EP | 0 881 541 A1 | 12/1998 |
| EP | 0 902 327 A2 | 3/1999 |
| EP | 0 932 256 A1 | 7/1999 |
| EP | 2 015 443 A1 | 1/2009 |
| EP | 2 072 500 A1 | 6/2009 |
| EP | 2 141 206 A1 | 1/2010 |
| GB | 2 180 358 A | 3/1987 |
| JP | 50-34443 | 11/1975 |
| JP | 50-34444 | 11/1975 |
| JP | 54-25957 B2 | 8/1979 |
| JP | 54-34327 B2 | 10/1979 |
| JP | 57-42009 A | 3/1982 |
| JP | 58-12577 B2 | 3/1983 |
| JP | 59-53836 A | 3/1984 |
| JP | 59-71048 A | 4/1984 |
| JP | 59-44615 B2 | 10/1984 |
| JP | 60-38989 A | 2/1985 |
| JP | 60-72927 A | 4/1985 |
| JP | 60-159743 A | 8/1985 |
| JP | 60-165623 A | 8/1985 |
| JP | 60-166946 A | 8/1985 |
| JP | 60-258539 A | 12/1985 |
| JP | 61-67003 A | 4/1986 |
| JP | 61-153602 A | 7/1986 |
| JP | 64-90516 A | 4/1989 |
| JP | 1-130103 A | 5/1989 |
| JP | 1-134306 A | 5/1989 |
| JP | 1-152449 A | 6/1989 |
| JP | 2-199403 A | 8/1990 |
| JP | 2-199404 A | 8/1990 |
| JP | 5-67405 A | 3/1993 |
| JP | 5-173320 A | 7/1993 |
| JP | 5-271576 A | 10/1993 |
| JP | 6-1638 A | 1/1994 |
| JP | 6-1938 A | 1/1994 |
| JP | 6-68309 A | 3/1994 |
| JP | 6-230212 A | 8/1994 |
| JP | 8-171863 A | 7/1996 |
| JP | 8-278629 A | 10/1996 |
| JP | 8-278630 A | 10/1996 |
| JP | 9-179299 A | 7/1997 |
| JP | 9-244230 A | 9/1997 |
| JP | 9-269410 A | 10/1997 |
| JP | 9-325209 A | 12/1997 |
| JP | 10-62980 A | 3/1998 |
| JP | 10-171119 A | 6/1998 |
| JP | 10-221843 A | 8/1998 |
| JP | 10-301276 A | 11/1998 |
| JP | 11-174459 A | 7/1999 |
| JP | 11-174464 A | 7/1999 |
| JP | 11-231523 A | 8/1999 |
| JP | 2000-39503 A | 2/2000 |
| JP | 2000-81701 A | 3/2000 |
| JP | 2001-40022 A | 2/2001 |
| JP | 2002-206014 A | 7/2002 |
| JP | 2004-69754 A | 3/2004 |
| JP | 2004-302245 A | 10/2004 |
| JP | 2005-77451 A | 3/2005 |
| JP | 2005-316449 A | 11/2005 |
| JP | 2005-338328 A | 12/2005 |
| JP | 2006-36750 A | 2/2006 |
| JP | 2006-53569 A | 2/2006 |
| JP | 3754065 B2 | 3/2006 |
| JP | 2011-65133 A | 3/2011 |
| JP | 2011-178776 A * | 9/2011 |
| WO | WO 90/01512 A1 | 2/1990 |
| WO | WO 96/41240 A1 | 12/1996 |
| WO | WO 99/38035 A1 | 7/1999 |
| WO | WO 03/021358 A1 | 3/2003 |
| WO | WO 2004/074328 A1 | 9/2004 |
| WO | WO 2005/080337 A1 | 9/2005 |
| WO | WO 2006/008251 A2 | 1/2006 |
| WO | WO 2008/138724 A1 | 11/2008 |
| WO | WO 2008/138732 A1 | 11/2008 |
| WO | WO 2009/019173 A1 | 2/2009 |
| WO | WO 2012/045736 A1 | 4/2012 |
| WO | WO 2013/167515 A1 | 11/2013 |

OTHER PUBLICATIONS

Computer-generated translation of JP 2011-178776 (Sep. 2011).*
U.S. Appl. No. 14/394,575, filed Oct. 15, 2014, Nishimae, et al.

* cited by examiner

*Primary Examiner* — John A McPherson

(74) *Attorney, Agent, or Firm* — McClelland, Maier & Neustadt, L.L.P.

(57) ABSTRACT

Oxime ester compounds of formula (I), wherein $R_1$, $R_2$, $R_3$, $R_4$, $R_5$, $R_6$, $R_7$, $R_8$, $R_9$, and $R_{10}$ independently of each other are hydrogen, $C_1$-$C_{20}$alkyl, (A), $COR_{14}$, $NO_2$, or $OR_{15}$; provided that at least one of $R_1$, $R_2$, $R_3$, $R_4$, $R_5$, $R_6$, $R_7$, $R_8$, $R_9$, and $R_{10}$ is (A), and provided that at least one of the remaining $R_1$, $R_2$, $R_3$, $R_4$, $R_5$, $R_6$, $R_7$, $R_8$, $R_9$, and $R_{10}$ is $COR_{14}$ or $NO_2$; $R_{11}$ is for example $C_1$-$C_{20}$alkyl, M or (B); X and $X_1$ are for example a direct bond; $R_{12}$ and $R'_{12}$ are for example hydrogen or $C_1$-$C_{20}$alkyl; $R_{13}$ and $R'_{13}$ are for example $C_6$-$C_{20}$aryl or $C_3$-$C_{20}$heteroaryl; M is (X), (Y) or (Z); $X_3$ is O, S or $NR_{19}$; $R_{14}$ and $R_{15}$ are for example phenyl; $R_{20}$, $R_{21}$, $R_{22}$, $R_{23}$, $R_{24}$, or $R_{25}$ for example are hydrogen, $COR_{14}$, $NO_2$, or (B); provided that at least two oxime ester groups are present in the molecule; are useful as photoinitiators.

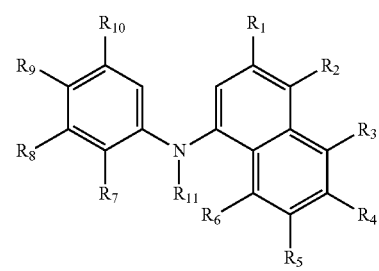

(I)

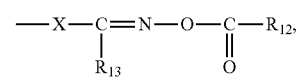

(A)

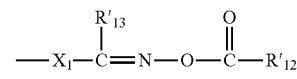

(B)

-continued
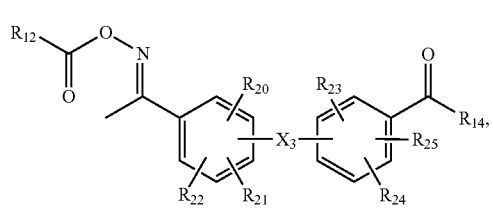
(X)
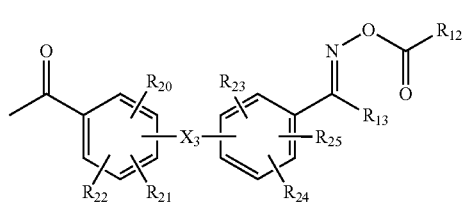
(Z)
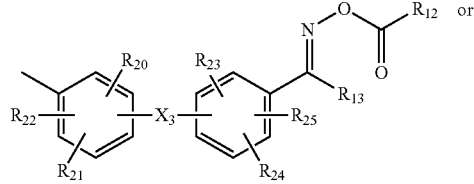
(Y) or
19 Claims, No Drawings

OXIME ESTER PHOTOINITIATORS

The invention pertains to new oxime ester compounds based on specific carbazole derivatives and their use as photoinitiators in photopolymerizable compositions, in particular in photoresist formulations, for example in resins for black matrix in color filter applications.

Oxime ester compounds having carbazole moieties are known in the art as photoinitiators. For example EP2015443, WO2008/138724 and EP2141206 disclose corresponding compounds. The extremely broad generic scope of JP 2006-36750-A (corresponding to WO2005/080337) also encompasses compounds with a carbazole moiety and inter alia condensed rings. However, the examples only show ring formation to the carbazole moiety including the oxime group. In WO2008/138732 also different carbazole-group containing photoinitiator compounds are described. Also here the broad generic scope covers a ring formation of substituents at the carbazole group, while no corresponding examples are disclosed. Further carbazole group containing photoinitiators are disclosed in WO2012/045736.

In photopolymerization technology there still exists a need for highly reactive, easy to prepare and easy to handle photoinitiators. For example, in color filter resist applications, highly pigmented resists are required for the high color quality property. With the increase of the pigment content, the curing of color resists becomes more difficult. Hence, photoinitiators having a high sensitivity are required. In addition, also such new photoinitiators must meet the high requirements of the industry regarding properties like, for example, easy handling, high solubility, thermal stability and storage stability. Furthermore the initiators in display applications should contribute to surface smoothness of a pattern, adhesiveness to the substrate etc.

It now has been found, that selected compounds are in particular suitable as photoinitiators.

Thus, subject of the invention are compounds of the formula I

Compounds of the formula I

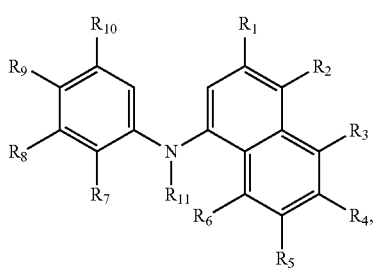
(I)

wherein $R_1, R_2, R_3, R_4, R_5, R_6, R_7, R_8, R_9$ and $R_{10}$ independently of each other are hydrogen, $C_1$-$C_{20}$alkyl,

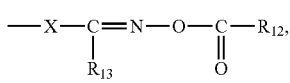

$COR_{14}$, $NO_2$, or $OR_{15}$;

provided that at least one of $R_1, R_2, R_3, R_4, R_5, R_6, R_7, R_8, R_9$, and $R_{10}$ is

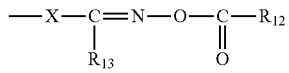

and provided that at least one of the remaining $R_1, R_2, R_3, R_4, R_5, R_6, R_7, R_8, R_9$, and $R_{10}$ is $COR_{14}$ or $NO_2$;

X is CO or a direct bond;

$R_{11}$ is $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$, $PO(OC_kH_{2k+1})_2$, or M;

or $R_{11}$ is $C_2$-$C_{20}$alkyl which is interrupted by one or more O, CO, S, C(O)O, OC(O), phenylene, naphthylene or $NR_{19}$, wherein the interrupted $C_2$-$C_{20}$alkyl is unsubstituted or substituted by one or more halogen, $OR_{15}$, $SR_{16}$, $COOR_{15}$, $CONR_{17}R_{18}$, $NR_{17}R_{18}$ or M;

or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{15}$, $NR_{17}R_{18}$, M,

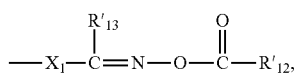

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

$R_{12}$ is hydrogen, $C_3$-$C_8$cycloalkyl, $C_2$-$C_5$alkenyl, $C_1$-$C_{20}$alkoxy or $C_1$-$C_{20}$alkyl which is unsubstituted or substituted by one or more halogen, phenyl, $C_1$-$C_{20}$alkylphenyl or CN;

or $R_{12}$ is phenyl or naphthyl, each of which is unsubstituted or substituted by one or more $C_1$-$C_6$alkyl, $C_1$-$C_4$haloalkyl, halogen, CN, $OR_{15}$, $SR_{16}$, or $NR_{17}R_{18}$;

or $R_{12}$ is $C_3$-$C_{20}$heteroaryl, benzyloxy or phenoxy, each of which is unsubstituted or substituted by one or more $C_1$-$C_6$alkyl, $C_1$-$C_4$haloalkyl and/or halogen;

$R_{13}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, $PO(OC_kH_{2k+1})_2$, SO—$C_1$-$C_{10}$alkyl, M, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$, $NR_{17}R_{18}$ or by M;

or $R_{13}$ is $C_1$-$C_{20}$alkyl which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $NR_{17}R_{18}$, $COOR_{15}$, $CONR_{17}R_{18}$, $PO(OC_kH_{2k+1})_2$,

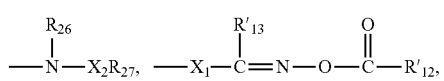

phenyl or by M, or $R_{13}$ is $C_1$-$C_{20}$alkyl which is substituted by phenyl which is substituted by one or more halogen, $C_1$-$C_{20}$alkyl, $C_1$-$C_4$haloalkyl, $OR_{15}$, $SR_{16}$ or by $NR_{17}R_{18}$;

or R$_{13}$ is C$_2$-C$_{20}$alkyl which is interrupted by one or more O, CO, S, C(O)O, OC(O), phenylene, naphthylene, or NR$_{19}$, wherein the interrupted C$_2$-C$_{20}$alkyl is unsubstituted or substituted by one or more halogen, OR$_{15}$, COOR$_{15}$, CONR$_{17}$R$_{18}$, phenyl, M, or by phenyl which is substituted by OR$_{15}$, SR$_{16}$ or NR$_{17}$R$_{18}$;

or R$_{13}$ is CN, CONR$_{17}$R$_{18}$, NO$_2$, C$_1$-C$_4$haloalkyl, S(O)$_m$—C$_1$-C$_6$alkyl; S(O)$_m$-phenyl which is unsubstituted or substituted by C$_1$-C$_{12}$alkyl or SO$_2$—C$_1$-C$_6$alkyl;

or R$_{13}$ is SO$_2$O-phenyl which is unsubstituted or substituted by C$_1$-C$_{12}$alkyl; or is diphenyl phosphinoyl or di-(C$_1$-C$_4$alkoxy)-phosphinoyl;

M is

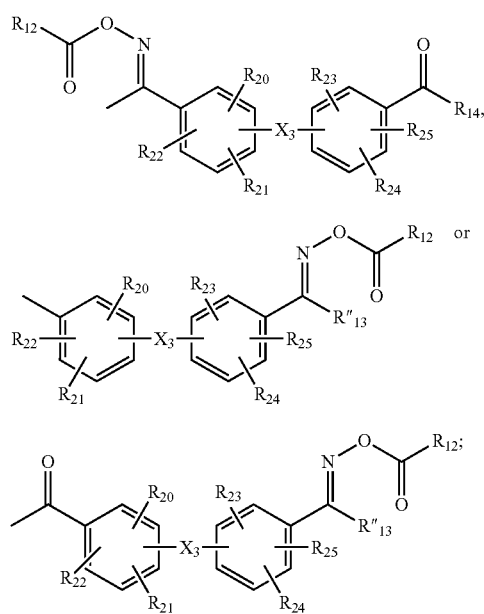

k is an integer 1-10;

m is 1 or 2;

R'$_{12}$ has one of the meanings as given for R$_{12}$;

R'$_{13}$ has one of the meanings as given for R$_{13}$;

R"$_{13}$ is C$_1$-C$_{20}$alkyl which is unsubstituted or substituted by phenyl or by phenyl which is substituted by halogen, C$_1$-C$_{20}$alkyl, C$_1$-C$_4$haloalkyl, OR$_{15}$, SR$_{16}$ or by NR$_{17}$R$_{18}$;

or R"$_{13}$ is C$_2$-C$_{20}$alkyl which is interrupted by one or more O, CO, S, C(O)O, OC(O), phenylene, naphthylene or NR$_{19}$, wherein the interrupted C$_2$-C$_{20}$alkyl is unsubstituted or substituted by one or more halogen, OR$_{15}$, COOR$_{15}$, CONR$_{17}$R$_{18}$, phenyl, or by phenyl which is substituted by OR$_{15}$, SR$_{16}$ or NR$_{17}$R$_{18}$;

or R"$_{13}$ is CN, CONR$_{17}$R$_{18}$, NO$_2$, C$_1$-C$_4$haloalkyl, S(O)$_m$—C$_1$-C$_6$alkyl; S(O)$_m$-phenyl which is unsubstituted or substituted by C$_1$-C$_{12}$alkyl or SO$_2$—C$_1$-C$_6$alkyl;

or R"$_{13}$ is SO$_2$O-phenyl which is unsubstituted or substituted by C$_1$-C$_{12}$alkyl; or is diphenyl phosphinoyl or di-(C$_1$-C$_4$alkoxy)-phosphinoyl;

or R"$_{13}$ is C$_6$-C$_{20}$aryl or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, PO(OC$_k$H$_{2k+1}$)$_2$, SO—C$_1$-C$_{10}$alkyl, SO$_2$—C$_1$-C$_{10}$alkyl, or by C$_2$-C$_{20}$alkyl which is interrupted by one or more O, CO, S, C(O)O, OC(O), phenylene, naphthylene or by NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or by NR$_{17}$R$_{18}$;

X$_1$ is O, CO, S or a direct bond;

X$_2$ is O, S, SO or SO$_2$;

X$_3$ is O, S or NR$_{19}$;

R$_{14}$ is C$_6$-C$_{20}$aryl or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, or by C$_2$-C$_{20}$alkyl which is interrupted by one or more O, S, or NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or NR$_{17}$R$_{18}$;

or R$_{14}$ is

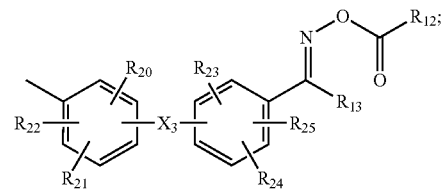

R$_{15}$ is hydrogen, phenyl-C$_1$-C$_3$alkyl, C$_1$-C$_{20}$alkyl which is unsubstituted or substituted by one or more halogen, OH, SH, CN, C$_3$-C$_6$alkenoxy, OCH$_2$CH$_2$CN, OCH$_2$CH$_2$(CO)O(C$_1$-C$_4$alkyl), O(CO)—(C$_1$-C$_4$alkyl), O(CO)—(C$_2$-C$_4$)alkenyl, O(CO)-phenyl, (CO)OH, (CO)O(C$_1$-C$_4$alkyl), C$_3$-C$_{20}$cycloalkyl, SO$_2$—(C$_1$-C$_4$haloalkyl), O(C$_1$-C$_4$haloalkyl), O(C$_1$-C$_{20}$arylene)-M, or by C$_3$-C$_{20}$cycloalkyl which is interrupted by one or more O;

or R$_{15}$ is C$_2$-C$_{20}$alkyl which is interrupted by one or more O, S or NR$_{19}$, which interrupted C$_2$-C$_{20}$alkyl is unsubstituted or substituted by O—C$_6$-C$_{20}$arylene-M;

or R$_{15}$ is (CH$_2$CH$_2$O)$_{n+1}$H, (CH$_2$CH$_2$O)$_n$(CO)—(C$_1$-C$_8$alkyl), C$_1$-C$_8$alkanoyl, C$_2$-C$_{12}$alkenyl, C$_3$-C$_6$alkenoyl or C$_3$-C$_{20}$cycloalkyl which is uninterrupted or interrupted by one or more O, S, CO or NR$_{19}$;

or R$_{15}$ is C$_1$-C$_8$alkyl-C$_3$-C$_{10}$cycloalkyl which is uninterrupted or interrupted by one or more O;

or R$_{15}$ is benzoyl which is unsubstituted or substituted by one or more C$_1$-C$_6$alkyl, halogen, OH or C$_1$-C$_3$alkoxy;

or R$_{15}$ is phenyl, naphthyl or C$_3$-C$_{20}$heteroaryl, each of which is unsubstituted or substituted by one or more halogen, OH, C$_1$-C$_{12}$alkyl, C$_1$-C$_{12}$alkoxy, CN, NO$_2$, phenyl-C$_1$-C$_3$alkyloxy, phenoxy, C$_1$-C$_{12}$alkylsulfanyl, phenylsulfanyl, N(C$_1$-C$_{12}$alkyl)$_2$, diphenylamino or

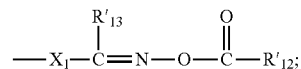

n is 1-20;

R$_{16}$ is hydrogen, C$_2$-C$_{12}$alkenyl, C$_3$-C$_{20}$cycloalkyl, or phenyl-C$_1$-C$_3$alkyl, wherein the C$_2$-C$_{12}$alkenyl, C$_3$-C$_{20}$cycloalkyl, or phenyl-C$_1$-C$_3$alkyl is uninterrupted or interrupted by one or more O, S, CO, NR$_{19}$;

or R$_{16}$ is C$_1$-C$_{20}$alkyl which is unsubstituted or is substituted by one or more OH, SH, CN, C$_3$-C$_6$alkenoxy, OCH$_2$CH$_2$CN, OCH$_2$CH$_2$(CO)O(C$_1$-C$_4$alkyl), O(CO)—(C$_2$-C$_4$)alkenyl, O(CO)—(C$_1$-C$_4$alkyl), O(CO)-phenyl or COOR$_{15}$ or S—C$_6$-C$_{20}$arylene-S-M;

or $R_{16}$ is $C_2$-$C_{20}$alkyl which is interrupted by one or more O, S, CO, $NR_{19}$, which interrupted $C_2$-$C_{20}$alkyl is unsubstituted or substituted by S—$C_6$-$C_{20}$arylene-M;

or $R_{16}$ is $(CH_2CH_2O)_nH$, $(CH_2CH_2O)_n(CO)$—($C_1$-$C_8$alkyl), $C_2$-$C_8$alkanoyl or $C_3$-$C_6$alkenoyl;

or $R_{16}$ is benzoyl which is unsubstituted or substituted by one or more $C_1$-$C_6$alkyl, halogen, OH, $C_1$-$C_4$alkoxy or $C_1$-$C_4$alkylsulfanyl;

or $R_{16}$ is phenyl, naphthyl or $C_3$-$C_{20}$heteroaryl, each of which is unsubstituted or substituted by one or more halogen, $C_1$-$C_{12}$alkyl, $C_1$-$C_4$haloalkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl$)_2$, diphenylamino, $(CO)O(C_1$-$C_8$alkyl), $(CO)$—$C_1$-$C_8$alkyl, $(CO)N(C_1$-$C_8$alkyl$)_2$ or

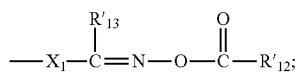

$R_{17}$ and $R_{18}$ independently of each other are hydrogen, $C_1$-$C_{20}$alkyl, $C_2$-$C_4$hydroxyalkyl, $C_2$-$C_{10}$alkoxyalkyl, $C_2$-$C_5$alkenyl, $C_3$-$C_{20}$cycloalkyl, phenyl-$C_1$-$C_3$alkyl, $C_1$-$C_8$alkanoyl, $C_1$-$C_8$alkanoyloxy, $C_3$-$C_{12}$alkenoyl, $SO_2$—($C_1$-$C_4$haloalkyl) or benzoyl;

or $R_{17}$ and $R_{18}$ are phenyl, naphthyl or $C_3$-$C_{20}$heteroaryl, each of which is unsubstituted or substituted by one or more halogen, $C_1$-$C_4$haloalkyl, $C_1$-$C_{20}$alkoxy, $C_1$-$C_{12}$alkyl, benzoyl or $C_1$-$C_{12}$alkoxy;

or $R_{17}$ and $R_{18}$ together with the N-atom to which they are attached form a 5- or 6-membered saturated or unsaturated ring which is uninterrupted or is interrupted by O, S or $NR_{19}$, and which 5- or 6-membered saturated or unsaturated ring is unsubstituted or substituted by one or more $C_1$-$C_{20}$alkyl, $C_1$-$C_{20}$alkoxy, =O, $OR_{15}$, $SR_{16}$, $NR_{28}R_{29}$, $COR_{30}$, $NO_2$, halogen, $C_1$-$C_4$-haloalkyl, CN, phenyl,

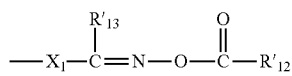

or by $C_3$-$C_{20}$cyclalkyl which is uninterrupted or is interrupted by one or more O, S, CO or $NR_{19}$;

or $R_{17}$ and $R_{18}$ together with the N-atom to which they are attached form a group

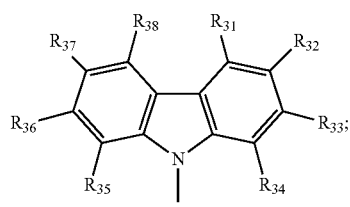

$R_{19}$ is hydrogen, $C_1$-$C_{20}$alkyl, $C_1$-$C_4$haloalkyl, $C_2$-$C_{20}$alkyl which is interrupted by one or more O, CO, C(O)O, or OC(CO), or is phenyl-$C_1$-$C_4$alkyl, $C_3$-$C_8$cycloalkyl which is uninterrupted or is interrupted by one or more O or CO, or $R_{19}$ is $COR_{30}$;

or $R_{19}$ is phenyl or naphthyl both of which are unsubstituted or substituted by one or more $C_1$-$C_{20}$alkyl, halogen, $C_1$-$C_4$haloalkyl, $OR_{15}$, $SR_{16}$, $NR_{17}R_{18}$, $COR_{14}$, or

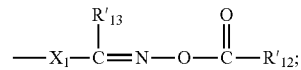

or $R_{19}$ is $C_1$-$C_6$alkylene or $C_2$-$C_6$alkenylene linked to the phenyl or naphthyl ring of the carbazole moiety and forming a 5- or 6-membered saturated or unsaturated ring;

$R_{20}$, $R_{21}$, $R_{22}$, $R_{23}$, $R_{24}$ or $R_{25}$ independently of each other are hydrogen, $COR_{14}$, $NO_2$,

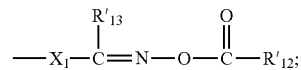

or one of $R_{21}$ and $R_{22}$, or $R_{24}$ and $R_{25}$ is

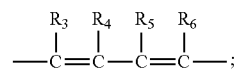

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system which is unsubstituted or substituted by one or more $C_1$-$C_{20}$alkyl, $C_1$-$C_4$haloalkyl, $C_1$-$C_{20}$alkoxy, =O, $OR_{15}$, $SR_{16}$, $NR_{17}R_{18}$, $COR_{14}$,

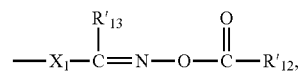

halogen, $NO_2$, CN, phenyl or by $C_3$-$C_{20}$cycloalkyl which is uninterrupted or is interrupted by one or more O, S, CO or $NR_{19}$;

$R_{26}$ is $COOR_{15}$, $CONR_{17}R_{18}$, $(CO)R_{15}$; or $R_{26}$ has one of the meanings given for $R_{17}$ and $R_{18}$;

$R_{27}$ is $COOR_{15}$, $CONR_{17}R_{18}$, $(CO)R_{15}$; or $R_{27}$ has one of the meanings given for $R_{15}$;

$R_{28}$ and $R_{29}$ independently of each other are hydrogen, $C_1$-$C_{20}$alkyl, $C_1$-$C_4$haloalkyl, $C_3$-$C_{10}$cycloalkyl or phenyl;

or $R_{28}$ and $R_{29}$ together with N-atom to which they are attached form a 5- or 6-membered saturated or unsaturated ring, which is uninterrupted or interrupted by O, S or $NR_{19}$, and which 5- or 6-membered saturated or unsaturated ring is not condensed or to which 5- or 6-membered saturated or unsaturated ring a benzene ring is condensed;

$R_{30}$ is hydrogen, OH, $C_1$-$C_{20}$alkyl, $C_1$-$C_4$haloalkyl, $C_2$-$C_{20}$alkyl which is interrupted by one or more O, CO or by $NR_{19}$, or is $C_3$-$C_{20}$cycloalkyl which is uninterrupted or is interrupted by O, S, CO or $NR_{19}$, or $R_{30}$ is phenyl, naphthyl, phenyl-$C_1$-$C_4$alkyl, $OR_{15}$, $SR_{16}$ or $NR_{17}R_{18}$;

$R_{31}$, $R_{32}$, $R_{33}$, $R_{34}$, $R_{35}$, $R_{36}$, $R_{37}$ and $R_{38}$ independently of each other are hydrogen,

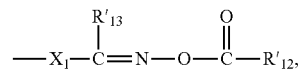

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl which is uninterrupted or is interrupted by one or more O, S, CO or $NR_{19}$;

or $R_{33}$ and $R_{34}$ or $R_{35}$ and $R_{36}$ or both, $R_{33}$ and $R_{34}$ and $R_{35}$ and $R_{36}$ are

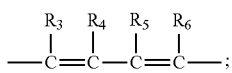

provided that at least two oxime ester groups selected from the group consisting of

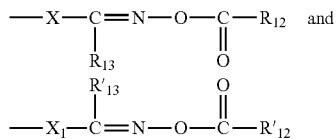

are present in the molecule.

The compounds of the formula I are characterized in that they comprise an annelated benzene ring at the carbazole moiety and in that more than one oxime ester moieties are present in the molecule. Namely the compound of the formula I comprises more than one, at least two, of the groups

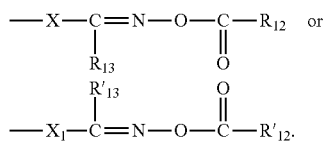

In addition the compounds of the formula I at least comprise a group $COR_{14}$ or $NO_2$. Further, via the definition of the radicals $R_{11}$, $R_{13}$, $R_{14}$, namely the group M, the introduction of a further oxime ester bearing aromatic moiety, e.g. a further carbazole group, into the molecule is an option.

$C_1$-$C_{20}$alkyl is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkyl or $C_4$-$C_{12}$- or $C_4$-$C_8$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl. $C_1$-$C_6$alkyl and $C_1$-$C_{12}$alkyl have the same meanings as given above for $C_1$-$C_{20}$alkyl up to the corresponding number of C-atoms.

$C_1$-$C_4$haloalkyl is $C_1$-$C_4$alkyl as defined above substituted by halogen as defined below. The alkyl radical is for example halogenated once, twice or three times, or mono- or polyhalogenated, up to the exchange of all H-atoms by halogen. It is for example $C_nH_xHal_y$, wherein $x+y=2n+1$ and Hal is halogen, preferably F. Specific examples are chloromethyl, trichloromethyl, trifluoromethyl or 2-bromopropyl, especially trifluoromethyl or trichloromethyl.

$C_2$-$C_4$hydroxyalkyl means $C_2$-$C_4$alkyl, which substituted by one or more, in particular one or two OH groups. The alkyl radical is linear or branched. Examples are 2-hydroxyethyl, 1-hydroxyethyl, 1-hydroxypropyl, 2-hydroxypropyl, 3-hydroxypropyl, 1-hydroxybutyl, 4-hydroxybutyl, 2-hydroxybutyl, 3-hydroxybutyl, 2,3-dihydroxypropyl, or 2,4-dihydroxybutyl.

$C_2$-$C_{10}$alkoxyalkyl is linear or branched $C_2$-$C_{10}$alkyl, which is interrupted by one O-atom. $C_2$-$C_{10}$alkyl has the same meanings as given above for $C_1$-$C_{20}$alkyl up to the corresponding number of C-atoms. Examples are methoxymethyl, methoxyethyl, methoxypropyl, ethoxymethyl, ethoxyethyl, ethoxypropyl, propoxymethyl, propoxyethyl, propoxypropyl.

$C_2$-$C_{20}$alkyl which is interrupted by one or more O, CO, S, C(O)O, OC(O), phenylene, naphthylene or $NR_{19}$, is for example interrupted 1-9, 1-5, 1-3 or once or twice by O, CO, S, C(O)O, OC(O), phenylene, naphthylene or $NR_{19}$. If more than one of the defined interrupting radicals are present they are of the same kind or different. Two O-atoms are separated by at least one methylene group, preferably at least two methylene groups, namely ethylene. The alkyl groups are linear or branched. For example the following structural units will occur, —$CH_2$—$CH_2$—O—$CH_2CH_3$, —$[CH_2CH_2O]_{y'}$—$CH_3$, wherein y=1-9, —$(CH_2$—$CH_2O)_7$—$CH_2CH_3$, —$CH_2$—$CH(CH_3)$—O—$CH_2$—$CH_2CH_3$, —$CH_2$—$CH(CH_3)$—O—$CH_2$—$CH_3$, —$CH_2$—$CH_2$—S—$CH_2CH_3$, —$CH_2$—$CH(CH_3)$—$NR_{19}$—$CH_2$—$CH_3$, —$CH_2$—$CH_2$—COO—$CH_2CH_3$ or —$CH_2$—$CH(CH_3)$—OCO—$CH_2$—$CH_2CH_3$, —$CH_2$—$CH_2$—O(CO)—$CH_2CH_3$, —$CH_2$—$CH_2$—(CO)O$CH_2CH_3$, —$CH_2$—$CH(CH_3)$—O(CO)—$CH_2$—$CH_2CH_3$,

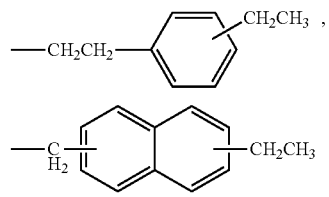

etc.

$C_3$-$C_{10}$cycloalkyl, $C_3$-$C_{10}$cycloalkyl and $C_3$-$C_8$Cycloalkyl in the context of the present application is to be understood as alkyl which at least comprises one ring. It is for example cyclopropyl, cyclobutyl, cyclopentyl, cyclohexyl, cyclooctyl, especially cyclopentyl and cyclohexyl. $C_3$-$C_{10}$cycloalkyl in the context of the present invention is also meant to cover bicyclic rings, in other words a bridged ring, such as for example

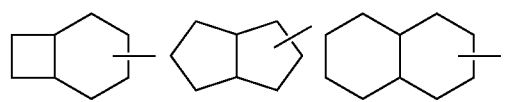

and corresponding rings. Further examples are structures like

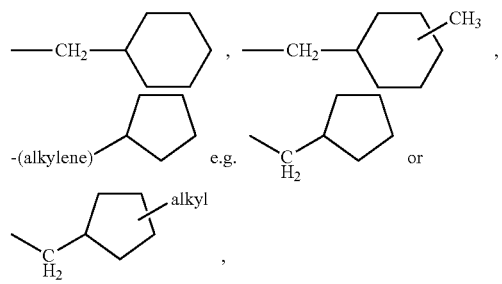

as well as bridged or fused ring systems, e.g.

etc. are also meant to be covered by the term.

$C_3$-$C_{20}$cycloalkyl which is interrupted by O, S, CO or $NR_{19}$ has the meanings given above, wherein at least one $CH_2$-group of the alkyl is exchanged by either O, S, CO or $NR_{19}$. Examples are structures like

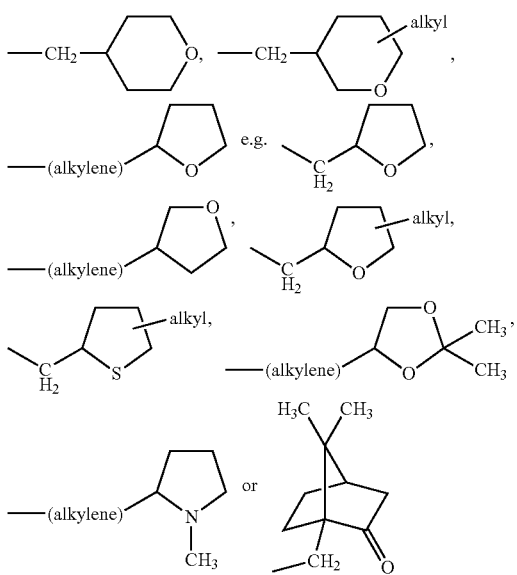

etc.

$C_1$-$C_8$alkyl-$C_3$-$C_{10}$cycloalkyl is $C_3$-$C_{10}$cycloalkyl as defined above which is substituted by one or more alkyl groups with up to 8 carbon atoms. Examples are

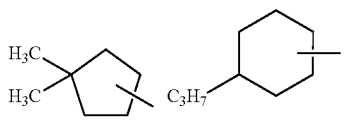

etc. Further, corresponding interrupted $C_1$-$C_8$alkyl-$C_3$-$C_{10}$cycloalkyl refers to the $C_1$-$C_8$alkyl-$C_3$-$C_{10}$cycloalkyl as defined above, where the interrupting atoms are considered as interrupting either the $C_1$-$C_8$alkyl or the $C_3$-$C_{10}$cycloalkyl, or both.

Examples are

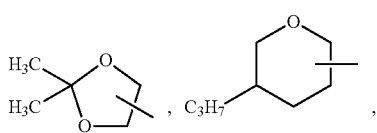

etc.

$C_1$-$C_{20}$alkoxy is linear or branched and is $C_1$-$C_{20}$alkyl, which is substituted by one-O-atom, namely $C_1$-$C_{20}$alkyl-O—. $C_1$-$C_{20}$alkyl has the same meanings as given above for $C_1$-$C_{20}$alkyl up to the corresponding number of C-atoms. $C_1$-$C_4$alkoxy is linear or branched, for example, methoxy, ethoxy, propoxy, isopropoxy, n-butyloxy, sec-butyloxy, isobutyloxy, tert-butyloxy. $C_1$-$C_8$alkoxy and $C_1$-$C_4$-alkoxy have the same meanings as described above up to the corresponding numbers of C-atoms.

$C_1$-$C_{12}$alkylsulfanyl is linear or branched and is $C_1$-$C_{12}$alkyl, which is substituted by one S-atom, namely $C_1$-$C_{12}$alkyl-S—. $C_1$-$C_{12}$alkyl has the same meanings as given above for $C_1$-$C_{20}$alkyl up to the corresponding number of C-atoms. $C_1$-$C_4$alkylsulfanyl is linear or branched, for example, methylsulfanyl, ethylsulfanyl, propylsulfanyl, isopropylsulfanyl, n-butylsulfanyl, sec-butylsulfanyl, isobutylsulfanyl, tert-butylsulfanyl.

Phenyl-$C_1$-$C_3$alkyl or phenyl-$C_1$-$C_4$alkyl is for example benzyl, phenylethyl, α-methylbenzyl, α,α-dimethylbenzyl, especially benzyl.

Phenyl-$C_1$-$C_3$alkoxyl or phenyl-$C_1$-$C_3$alkyloxy is for example benzyloxy, phenylethyloxy, α-methylbenzyloxy or α,α-dimethylbenzyloxy, especially benzyloxy.

$C_2$-$C_{12}$alkenyl or $C_2$-$C_5$alkenyl radicals are linear or branched and are mono- or polyunsaturated and are for example $C_2$-$C_{10}$-, $C_2$-$C_8$-, $C_2$-$C_5$-alkenyl e.g. vinyl, allyl, methallyl, 1,1-dimethylallyl, 1-butenyl, 3-butenyl, 2-butenyl, 1,3-pentadienyl, 5-hexenyl, 7-octenyl or dodecenyl, especially allyl. $C_2$-$C_5$alkenyl radicals have the same meanings as given above for $C_2$-$C_{12}$alkenyl radicals up to the corresponding number of C-atoms.

$C_2$-$C_{12}$alkenyl which is interrupted by one or more O, S, CO or $NR_{19}$ is for example interrupted 1-9, 1-5, 1-3 or once or twice by O, S, CO or $NR_{19}$. If more than one of the interrupting radicals are present they are of the same kind or different. Two O-atoms are separated by at least one methylene group, preferably at least two methylene groups, namely ethylene. The alkenyl groups are linear or branched and are defined as above. For example following structural units can be formed —CH=CH—O—$CH_2CH_3$, —CH=CH—O—CH=$CH_2$ etc.

$C_3$-$C_6$alkenoxy is mono or polyunsaturated, linear or branched, and has one of the meanings given for alkenyl above with the attached oxy group up to the corresponding number of C-atoms. Examples are allyloxy, methallyloxy, butenyloxy, pentenoxy, 1,3-pentadienyloxy, 5-hexenyloxy.

$C_1$-$C_8$alkanoyl=$C_1$-$C_8$alkylcarbonyl is linear or branched and is, for example, $C_1$-$C_6$- or $C_1$-$C_4$alkanoyl or $C_4$-$C_8$alkanoyl. Examples are formyl, acetyl, propionyl, butanoyl, isobutanoyl, pentanoyl, hexanoyl, heptanoyl or octanoyl, preferably acetyl.

$C_3$-$C_6$alkenoyl is mono or polyunsaturated, linear or branched, and is for example propenoyl, 2-methyl-propenoyl, butenoyl, pentenoyl, 1,3-pentadienoyl, 5-hexenoyl.

$C_6$-$C_{20}$aryloxycarbonyl is for example phenyloxycabonyl [=phenyl-O—(CO)—], naphtyloxycarbonyl, anthryloxycarbonyl etc.

$C_5$-$C_{20}$heteroaryloxycarbonyl is $C_5$-$C_{20}$heteroaryl-O—CO—.

$C_1$-$C_{20}$alkylphenyl refers to phenyl which is substituted by one or more alkyl groups, where the sum of the C atoms is up to 20.

$C_6$-$C_{20}$aryl is for example phenyl, naphthyl, anthryl, phenanthryl, pyrene, chrysene, naphthacene, triphenylene etc., in particular phenyl or naphthyl, preferably phenyl. Naphthyl is 1-naphthyl or 2-naphthyl.

In the context of the present invention $C_3$-$C_{20}$heteroaryl is meant to comprise either one ring or a multiple ring system, e.g. a fused ring-system. Examples are thienyl, benzo[b]thienyl, naphtho[2,3-b]thienyl, thianthrenyl, furyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 1H-tetrazol-5-yl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl, 10-methyl-2-phenoxazinyl, etc.

$C_3$-$C_{20}$heteroaryl in particular is thienyl, benzo[b]thienyl, carbazolyl, thianthrenyl, thioxanthyl, 1-methyl-2-indolyl or 1-methyl-3-indolyl; especially thienyl.

Substituted aryl radicals phenyl, naphthyl, $C_6$-$C_{20}$aryl or $C_5$-$C_{20}$heteroaryl etc. are substituted 1 to 7, 1 to 6 or 1 to 4 times respectively, in particular one, two or three times. It is evident that a defined aryl or heteroaryl radical cannot have more substituents than free "CH" or "NH" positions are at the defined ring.

Substituents on the phenyl ring are preferably in positions 4 or in 3,4-, 3,4,5-, 2,6-, 2,4- or 2,4,6-configuration on the phenyl ring.

Interrupted radicals which are interrupted once or more times are for example interrupted 1-19, 1-15, 1-12, 1-9, 1-7, 1-5, 1-4, 1-3 or once or twice (it is evident, that the number of interrupting atoms depends on the number of C-atoms to be interrupted).

Substituted radicals, which are substituted once or more times have for example 1-7, 1-5, 1-4, 1-3 or one or two identical or different substituents.

A radical substituted by one or more defined substituents is meant to have either one substituent or more substituents of identical or different definitions as given.

Halogen is fluorine, chlorine, bromine and iodine, especially fluorine, chlorine and bromine, preferably fluorine and chlorine.

If M is

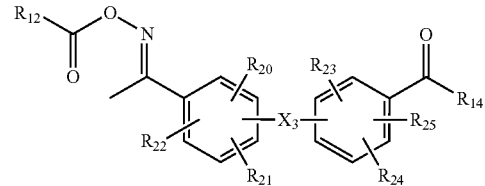

for example structures like the following are formed

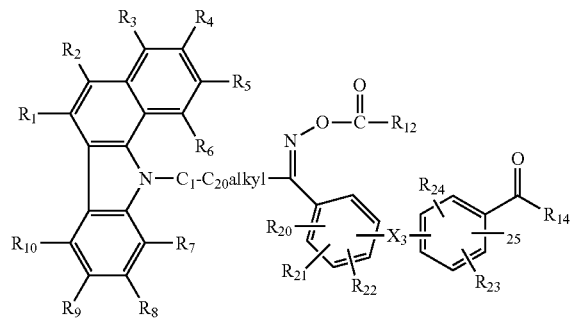

($R_{11}$=$C_1$-$C_{20}$alkyl substituted by M),

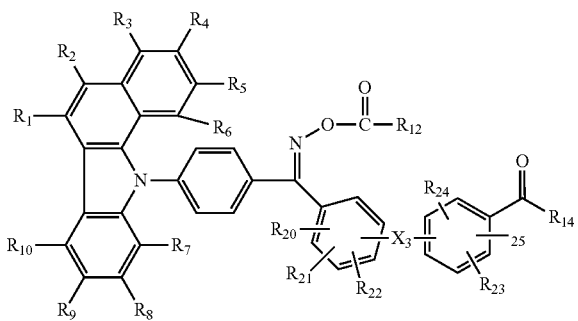

($R_{11}$=$C_6$-$C_{20}$aryl substituted by M), etc.

If M is

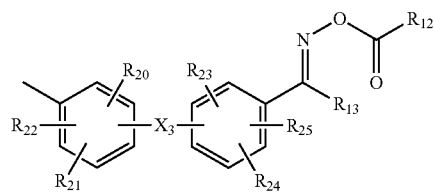

for example structures like the following are formed
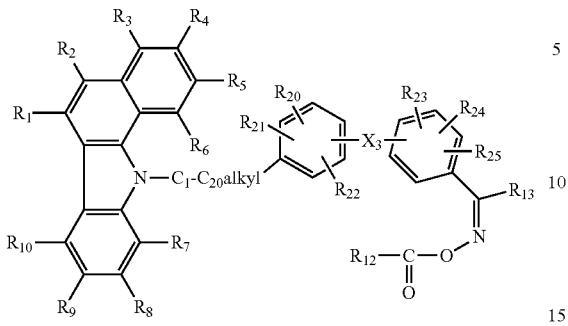
($R_{11}$=$C_1$-$C_{20}$alkyl substituted by M),
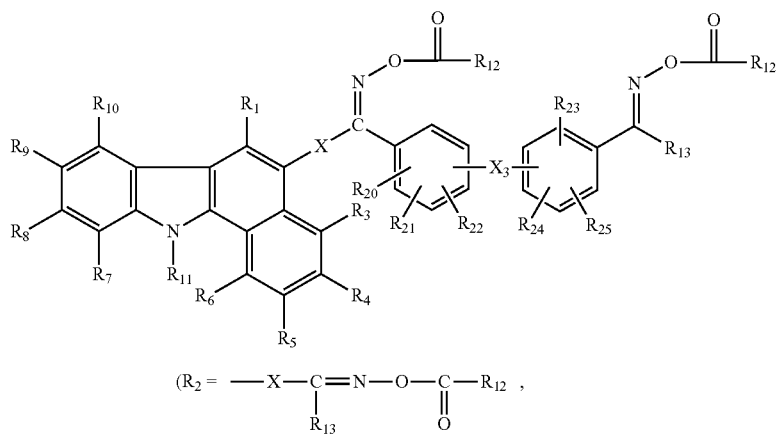
($R_2$ = —X—C(R$_{13}$)=N—O—C(=O)—$R_{12}$ ,
$R_{13}$=$C_1$-$C_{20}$alkyl, substituted by M), etc.
If M is
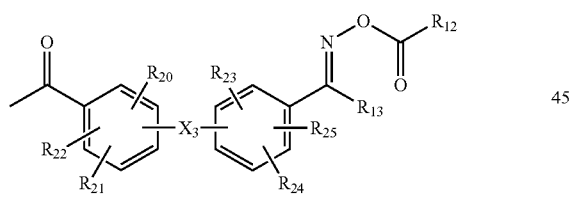
for example structures like the following are formed
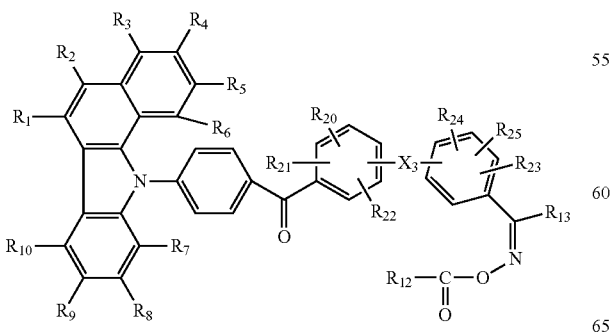
($R_{11}$=$C_6$-$C_{20}$aryl substituted by M), etc.

If R$_{14}$ is

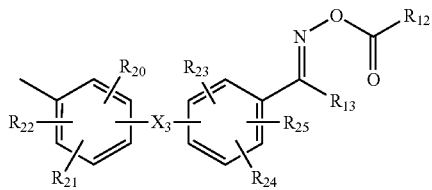

for example structures like the following are formed

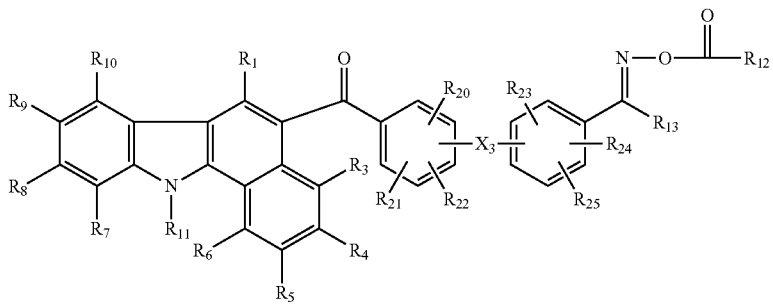

(R$_2$=COR$_{14}$), etc.

If R$_{17}$ and R$_{18}$ together with the N-atom to which they are attached form a 5- or 6-membered saturated or unsaturated ring which optionally is interrupted by O, S or NR$_{19}$, saturated or unsaturated rings are formed, for example aziridine, pyrrole, thiazole, pyrrolidine, oxazole, pyridine, 1,3-diazine, 1,2-diazine, piperidine or morpholine. Preferably, if R$_{17}$ and R$_{18}$ together with the N-atom to which they are attached form a 5- or 6-membered saturated or unsaturated ring which optionally is interrupted by O, S or NR$_{19}$, 5- or 6-membered saturated rings which are not interrupted or which are interrupted by O or NR$_{19}$, in particular by O, are formed.

If R$_{28}$ and R$_{29}$ together with N-atom to which they are attached form a 5- or 6-membered saturated or unsaturated ring, which is uninterrupted or is interrupted by O, S or NR$_{19}$, and which 5- or 6-membered saturated or unsaturated ring is not condensed or to which 5- or 6-membered saturated or unsaturated ring a benzene ring is condensed, saturated or unsaturated rings are formed, for example aziridine, pyrrole, thiazole, pyrrolidine, oxazole, pyridine, 1,3-diazine, 1,2-diazine, piperidine or morpholine, or corresponding annelated rings, e.g.

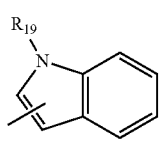

etc.

If R$_{19}$ is C$_1$-C$_6$alkylene or C$_2$-C$_6$alkenylene linked to the phenyl or naphthyl ring of the carbazole moiety and forming a 5- or 6-membered saturated or unsaturated ring, for example the following structures are formed

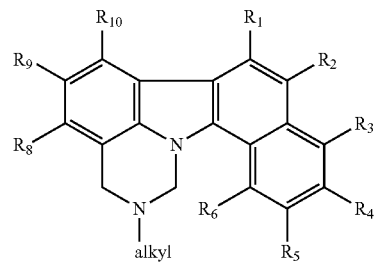

-continued

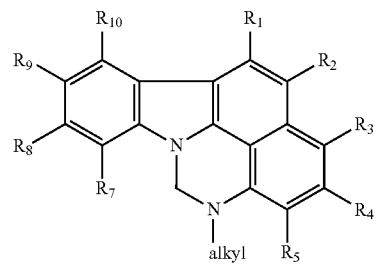

(R$_{11}$=alkyl interrupted by NR$_{19}$);

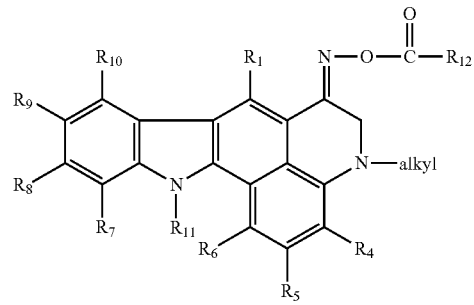

(R$_{13}$=alkyl interrupted by NR$_{19}$) etc.

If one of R$_{20}$, R$_{21}$ or R$_{22}$ and one of R$_{23}$, R$_{24}$ or R$_{25}$ together with X$_3$ and the phenyl rings to which they are attached form a heteroaromatic ring system which is unsubstituted or substituted, for example structures like the following are formed

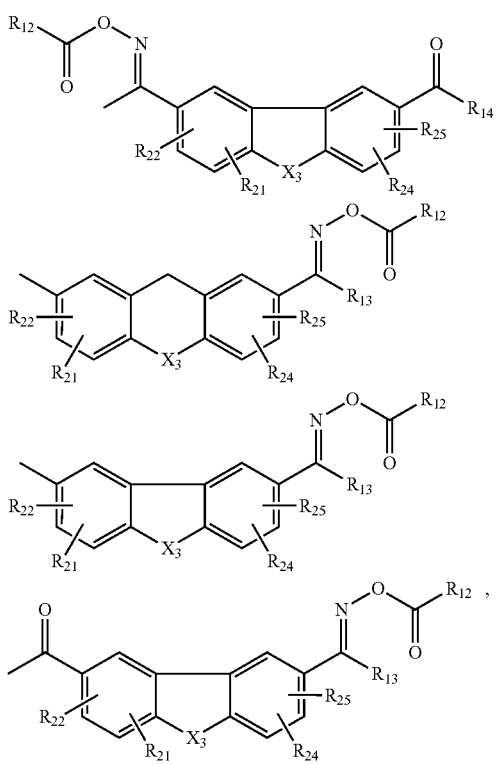

etc., in particular

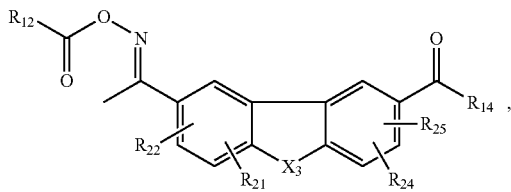

The term "provided that at least two oxime ester groups are present in the molecule" in any of the claims and the remainder of the text refers to "provided that at least two oxime ester groups selected from the group consisting of

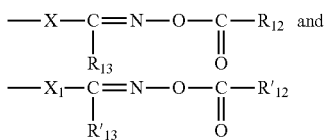

are present in the molecule.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

The term "optionally interrupted" means, that the radical to which it refers is either not interrupted or is interrupted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated in the text for the compounds according to the present invention in the context of this invention are intended to refer to all categories of the claims, that is to the claims directed to compositions, use, process, color filter etc. as well.

$R_2$ or $R_3$ for example independently of each other are $C_1$-$C_{20}$alkyl,

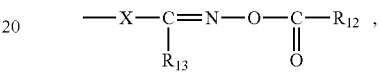

$COR_{14}$ or $NO_2$; and $R_1$, $R_3$, $R_4$, $R_5$, $R_6$, $R_7$, $R_8$ and $R_{10}$ are hydrogen.

In particular $R_2$ is $COR_{14}$ or $NO_2$ and $R_9$ is

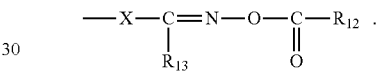

$R_1$, $R_3$, $R_4$, $R_5$, $R_6$, $R_7$, $R_8$ and $R_{10}$ preferably are hydrogen.
X preferably is a direct bond.
$X_1$ is for example O, S or a direct bond; or is for example O, CO or a direct bond; or is for example O or a direct bond; or is for example S or a direct bond; or is for example S or CO; or is for example S and a direct bond; preferably $X_1$ is a direct bond.
$X_2$ is for example O, S or SO; or is for example O or S, preferably O.
$X_3$ is for example O or $NR_{19}$; or is for example S or $NR_{19}$; preferably $NR_{19}$.
$R_{11}$ is for example $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$ or M; or is $C_2$-$C_{20}$alkyl which is interrupted by one or more O, CO, C(O)O, OC(O) phenylene or $NR_{19}$, wherein the interrupted $C_2$-$C_{20}$alkyl is unsubstituted or substituted by one or more halogen, $OR_{15}$, $SR_{16}$, $COOR_{15}$, $CONR_{17}R_{18}$, $NR_{17}R_{18}$ or M; or is phenyl, naphthyl or $C_3$-$C_{20}$heteroaryl, in particular thienyl, each of which is unsubstituted or substituted by one or more halogen, $C_1$-$C_4$haloalkyl, CN, $NO_2$, $OR_{15}$, $SR_{16}$, $NR_{17}R_{18}$, M,

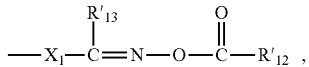

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, phenyl, $C_3$-$C_8$cycloalkyl, $OR_{15}$, $SR_{16}$ or $NR_{17}R_{18}$.

Or $R_{11}$ is for example $C_1$-$C_{20}$alkyl which is unsubstituted or substituted by one or more halogen, $OR_{15}$, $SR_{16}$, $NR_{17}R_{18}$ or M; or is $C_2$-$C_{20}$alkyl which is interrupted by one or more O, CO, C(O)O, OC(O), phenylene or NR$_{19}$, wherein the interrupted C$_1$-C$_{20}$alkyl is unsubstituted or substituted by one or more halogen, OR$_{15}$, COOR$_{15}$, NR$_{17}$R$_{18}$ or M;

or is phenyl, naphthyl or C$_3$-C$_{20}$heteroaryl, in particular thienyl, each of which is unsubstituted or substituted by one or more halogen, C$_1$-C$_4$haloalkyl, CN, NO$_2$, OR$_{15}$, NR$_{17}$R$_{18}$,

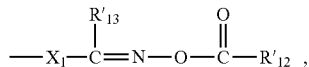

or by C$_1$-C$_{20}$alkyl which is interrupted by one or more O, S, or NR$_{19}$, or each of which is substituted by one or more C$_1$-C$_{20}$alkyl.

Or R$_{11}$ is for example C$_1$-C$_{20}$alkyl which is unsubstituted or substituted by one or more NR$_{17}$R$_{18}$; or is C$_2$-C$_{20}$alkyl which is interrupted by one or more C(O)O, OC(O) or phenylene, wherein the interrupted C$_1$-C$_{20}$alkyl is unsubstituted or substituted by NR$_{17}$R$_{18}$; or is phenyl, naphthyl or C$_3$-C$_{20}$heteroaryl, in particular thienyl, each of which is unsubstituted or substituted by

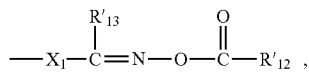

Preferably R$_{11}$ is C$_1$-C$_{20}$alkyl, phenyl or C$_3$-C$_{20}$heteroaryl, in particular thienyl, each of which is unsubstituted or substituted by

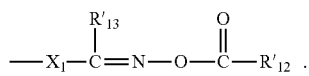

R$_{12}$ is for example hydrogen, C$_3$-C$_8$cycloalkyl, C$_2$-C$_5$alkenyl, C$_1$-C$_{20}$alkoxy, C$_1$-C$_{20}$alkyl, phenyl, naphthyl, or C$_3$-C$_{20}$heteroaryl.

Or R$_{12}$ is for example hydrogen, C$_3$-C$_8$cycloalkyl, C$_2$-C$_5$alkenyl, 01-C$_{20}$alkyl or phenyl.

Or R$_{12}$ is for example C$_3$-C$_8$cycloalkyl, C$_2$-C$_5$alkenyl, C$_1$-C$_{20}$alkyl, in particular C$_3$-C$_8$cycloalkyl or C$_1$-C$_{20}$alkyl, preferably C$_1$-C$_{20}$alkyl.

R$_{13}$ is for example C$_6$-C$_{20}$aryl, in particular phenyl or naphthyl, or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, M, or by C$_2$-C$_{20}$alkyl which is interrupted by one or more O, CO, S, C(O)O, OC(O), phenylene, naphthylene or by NR$_{19}$, or each of which is substituted by one or more C$_1$-C$_{20}$alkyl which is unsubstituted or substituted by one or more OR$_{15}$, SR$_{16}$, NR$_{17}$R$_{18}$ or by M; or R$_{13}$ is C$_1$-C$_{20}$alkyl which is unsubstituted or substituted by one or more halogen, OR$_{15}$, SR$_{16}$, C$_3$-C$_8$cycloalkyl, C$_3$-C$_{20}$heteroaryl, NR$_{17}$R$_{18}$, COOR$_{15}$, CONR$_{17}$R$_{18}$,

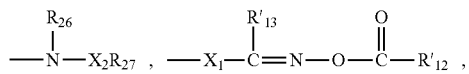

phenyl or by M; or
R$_{13}$ is C$_1$-C$_{20}$alkyl which is substituted by phenyl which is substituted by halogen, C$_1$-C$_{20}$alkyl, C$_1$-C$_4$haloalkyl, OR$_{15}$, SR$_{16}$ or by NR$_{17}$R$_{18}$; or R$_{13}$ is C$_2$-C$_{20}$alkyl which is interrupted by one or more O, CO, S, C(O)O, OC(O), phenylene, naphthylene or NR$_{19}$.

Or R$_{13}$ is for example C$_6$-C$_{20}$aryl, in particular phenyl or naphthyl, each of which is unsubstituted or substituted by one or more OR$_{15}$, SR$_{16}$, NR$_{17}$R$_{18}$, or each of which is substituted by one or more C$_1$-C$_{20}$alkyl; or R$_{13}$ is C$_1$-C$_{20}$alkyl which is unsubstituted or substituted by one or more COOR$_{15}$ or by M.

Or R$_{13}$ is for example C$_6$-C$_{20}$aryl, in particular phenyl or naphthyl, preferably phenyl, each of which is unsubstituted or substituted by OR$_{15}$; or R$_{13}$ is C$_1$-C$_{20}$alkyl which is unsubstituted or substituted by one or more COOR$_{15}$ or by M.

R'$_{12}$ has one of the meanings as given for R$_{12}$; including the examples and preferences as given above. In particular R'$_{12}$ is C$_1$-C$_{20}$ or C$_1$-C$_4$alkyl.

R'$_{13}$ has one of the meanings as given for R$_{13}$; including the examples and preferences as given above. In particular R'$_{13}$ is C$_1$-C$_{20}$alkyl which is substituted by COOR$_{15}$, especially C$_1$-C$_4$alkyl which is substituted by COOR$_{15}$.

R"$_{13}$ for example is C$_1$-C$_{20}$alkyl which is unsubstituted or substituted by phenyl or by phenyl which is substituted by halogen or C$_1$-C$_{20}$alkyl; or R"$_{13}$ is C$_2$-C$_{20}$alkyl which is interrupted by one or more O, CO, S, C(O)O, OC(O), phenylene or NR$_{19}$; or R"$_{13}$ is CN, CONR$_{17}$R$_{18}$, NO$_2$, C$_1$-C$_4$haloalkyl, S(O)$_m$—C$_1$-C$_8$alkyl, S(O)$_m$-phenyl; or R"$_{13}$ is SO$_2$O-phenyl. C$_6$-C$_{20}$aryl which is unsubstituted or substituted by one or more phenyl, halogen, C$_1$-C$_4$haloalkyl, CN, NO$_2$, OR$_{15}$, SR$_{16}$, NR$_{17}$R$_{18}$, PO(OC$_k$H$_{2k+1}$)$_2$, SO—C$_1$-C$_{10}$alkyl, SO$_2$—C$_1$-C$_{10}$alkyl, or by C$_2$-C$_{20}$alkyl which is interrupted by one or more O, CO, S, C(O)O, OC(O), phenylene, naphthylene or by NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or by NR$_{17}$R$_{18}$.

Or R"$_{13}$ for example is C$_1$-C$_{20}$alkyl which is unsubstituted or substituted by phenyl; or R"$_{13}$ is C$_2$-C$_{20}$alkyl which is interrupted by one or more O, CO, S, C(O)O, OC(O), phenylene or NR$_{19}$; R"$_{13}$ is C$_6$-C$_{20}$aryl, in particular phenyl or naphthyl, each of which is unsubstituted or substituted by one or more OR$_{15}$, SR$_{16}$, NR$_{17}$R$_{18}$, or each of which is substituted by one or more C$_1$-C$_{20}$alkyl;

In particular R"$_{13}$ is C$_1$-C$_{20}$alkyl which is unsubstituted or substituted by phenyl; preferably R"$_{13}$ is C$_1$-C$_{20}$alkyl.

M is for example

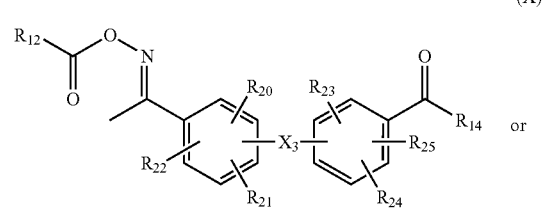

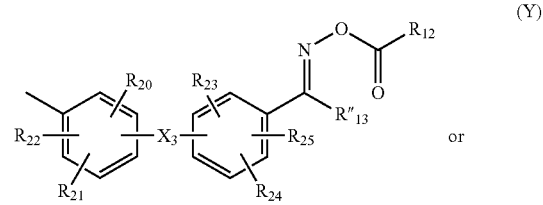

-continued

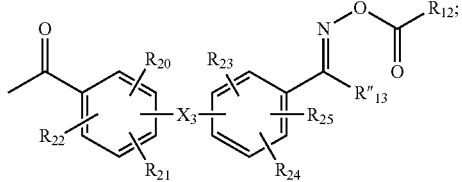

in particular a group (X), or (Z);

$R_{14}$ for example is $C_6$-$C_{20}$aryl, in particular phenyl or naphthyl, or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, $C_1$-$C_{20}$alkyl or by $C_1$-$C_{20}$alkyl which is interrupted by one or more O, S, or $NR_{19}$; or $R_{14}$ is

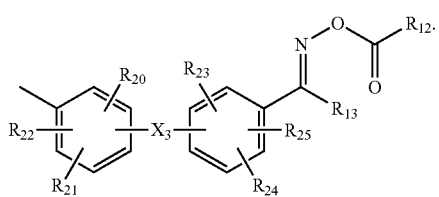

Or $R_{14}$ for example is $C_6$-$C_{20}$aryl, in particular phenyl or naphthyl, each of which is unsubstituted or substituted by one or more $OR_{15}$, $SR_{16}$, $NR_{17}R_{18}$ or by $C_1$-$C_{20}$alkyl; or $R_{14}$ is

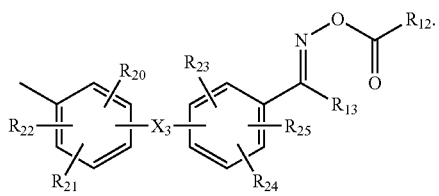

In particular $R_{14}$ is $C_6$-$C_{20}$aryl, in particular phenyl, which is unsubstituted or substituted, in particular substituted, by one or more $OR_{15}$, $NR_{17}R_{18}$ or by $C_1$-$C_{20}$alkyl; or $R_{14}$ is

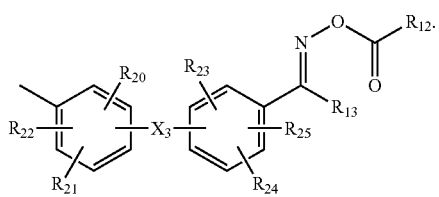

$R_{15}$ for example is hydrogen, phenyl-$C_1$-$C_3$alkyl, $C_1$-$C_{20}$alkyl which is unsubstituted or substituted by one or more halogen, OH, SH, CN, $OCH_2CH_2(CO)O(C_1$-$C_4$alkyl), $O(OC)(C_1$-$C_4$alkyl), $O(CO)$-phenyl, (CO)OH, (CO)O($C_1$-$C_4$alkyl), $C_3$-$C_{20}$cycloalkyl, $O(C_1$-$C_{20}$arylene)-M, or by $C_3$-$C_{20}$cycloalkyl which is interrupted by one or more O; or $R_{15}$ is $C_2$-$C_{20}$alkyl which is interrupted by one or more O, S or $NR_{19}$; or $R_{15}$ is $C_1$-$C_8$alkanoyl, $C_2$-$C_{12}$alkenyl, $C_3$-$C_6$alkenoyl or $C_3$-$C_{20}$cycloalkyl; or $R_{15}$ is $C_1$-$C_8$alkyl-$C_3$-$C_{10}$cycloalkyl which is uninterrupted or interrupted by one or more O; or $R_{15}$ is benzoyl; or $R_{15}$ is phenyl, naphthyl or $C_3$-$C_{20}$heteroaryl, in particular phenyl, each of which is unsubstituted or substituted by one or more halogen, OH, $C_1$-$C_{12}$alkyl, $C_1$-$C_{12}$alkoxy, CN, $NO_2$, phenoxy, $C_1$-$C_{12}$alkylsulfanyl, phenylsulfanyl, $N(C_1$-$C_{12}$alkyl)$_2$, diphenylamino or

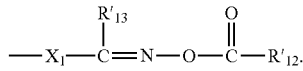

Or $R_{15}$ for example is phenyl-$C_1$-$C_3$alkyl, $C_1$-$C_{20}$alkyl which is unsubstituted or substituted by one or more halogen, OH, SH, CN, $C_3$-$C_{20}$cycloalkyl, $O(C_1$-$C_{20}$arylene)-M, or by $C_3$-$C_{20}$cycloalkyl which is interrupted by one or more O; or $R_{15}$ is $C_2$-$C_{20}$alkyl which is interrupted by one or more O, S or $NR_{19}$; or $R_{15}$ is phenyl or naphthyl, in particular phenyl, each of which is unsubstituted or substituted by one or more halogen, OH, $C_1$-$C_{12}$alkyl, $C_1$-$C_{12}$alkoxy, CN, $NO_2$, $N(C_1$-$C_{12}$alkyl)$_2$, diphenylamino or

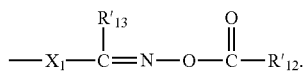

In particular $R_{15}$ is $C_1$-$C_{20}$alkyl which is unsubstituted or substituted by one or more halogen or $O(C_1$-$C_{20}$arylene)-M.

$R_{16}$ for example is $C_2$-$C_{12}$alkenyl, $C_3$-$C_{20}$cycloalkyl, phenyl-$C_1$-$C_3$alkyl or $C_1$-$C_{20}$alkyl; or $R_{16}$ is $C_2$-$C_{20}$alkyl which is interrupted by one or more O, S, CO, $NR_{19}$ or $COOR_{15}$; or $R_{16}$ is phenyl, naphthyl or $C_3$-$C_{20}$heteroaryl, in particular phenyl, each of which is unsubstituted or substituted by one or more halogen, $C_1$-$C_{12}$alkyl, $C_1$-$C_4$haloalkyl, $C_1$-$C_{12}$alkoxy, CN, $NO_2$, phenyl-$C_1$-$C_3$alkyloxy, phenoxy, $C_1$-$C_{12}$alkylsulfanyl, phenylsulfanyl, $N(C_1$-$C_{12}$alkyl)$_2$, diphenylamino, (CO)O($C_1$-$C_8$alkyl), (CO)—$C_1$-$C_8$alkyl, (CO)N($C_1$-$C_8$alkyl)$_2$ or

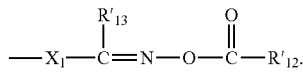

Or $R_{16}$ for example is $C_2$-$C_{12}$alkenyl, $C_3$-$C_{20}$cycloalkyl, phenyl-$C_1$-$C_3$alkyl or $C_1$-$C_{20}$alkyl; or $R_{16}$ is $C_2$-$C_{20}$alkyl which is interrupted by one or more O, S, CO, $NR_{19}$ or $COOR_{15}$; or $R_{16}$ is phenyl or naphthyl, in particular phenyl, each of which is unsubstituted or substituted by one or more halogen, $C_1$-$C_{12}$alkyl or

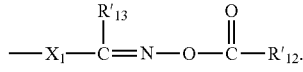

In particular $R_{16}$ is phenyl which is unsubstituted or substituted, in particular substituted, by

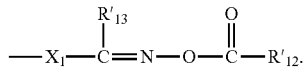

$R_{17}$ and $R_{18}$ for example are independently of each other are hydrogen, $C_1$-$C_{20}$alkyl, $C_2$-$C_4$hydroxyalkyl, $C_2$-$C_{10}$alkoxyalkyl, $C_2$-$C_5$alkenyl, $C_3$-$C_{20}$cycloalkyl, phenyl-$C_1$-$C_3$alkyl, $C_1$-$C_8$alkanoyl, $C_1$-$C_8$alkanoyloxy, $C_3$-$C_{12}$alkenoyl or benzoyl; or $R_{17}$ and $R_{18}$ are phenyl, naphthyl or $C_3$-$C_{20}$heteroaryl, in particular phenyl, each of which is unsubstituted or substituted by one or more halogen, $C_1$-$C_4$haloalkyl, $C_1$-$C_{20}$alkoxy, $C_1$-$C_{12}$alkyl, benzoyl or $C_1$-$C_{12}$alkoxy; or $R_{17}$ and $R_{18}$ together with the N-atom to which they are attached form a 5- or 6-membered saturated or unsaturated ring which is uninterrupted or is interrupted by O or $NR_{19}$; or $R_{17}$ and $R_{18}$ together with the N-atom to which they are attached form a group

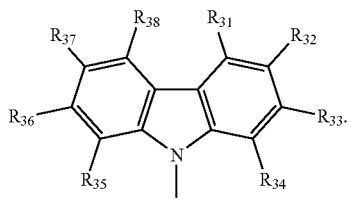

Or $R_{17}$ and $R_{18}$ for example are independently of each other are hydrogen, $C_1$-$C_{20}$alkyl or $C_2$-$C_4$hydroxyalkyl; or are phenyl which is unsubstituted or substituted by one or more halogen or $C_1$-$C_{12}$alkyl; or $R_{17}$ and $R_{18}$ together with the N-atom to which they are attached form a morpholino ring; or $R_{17}$ and $R_{18}$ together with the N-atom to which they are attached form a group

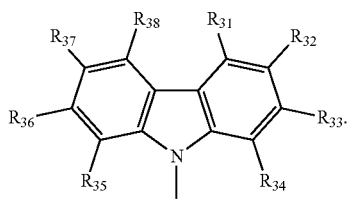

In particular $R_{17}$ and $R_{18}$ together with the N-atom to which they are attached form a group

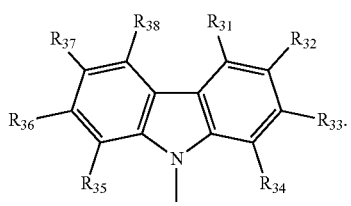

$R_{19}$ for example is hydrogen, $C_1$-$C_{20}$alkyl, $C_1$-$C_4$haloalkyl, $C_2$-$C_{20}$alkyl which is interrupted by one or more O, CO, C(O)O, or OC(CO), or is phenyl-$C_1$-$C_4$alkyl, $C_3$-$C_8$cycloalkyl, (CO)$R_{30}$; or $R_{19}$ is phenyl or naphthyl both of which are unsubstituted or substituted by one or more $C_1$-$C_{20}$alkyl, halogen, $C_1$-$C_4$haloalkyl, $OR_{15}$, $SR_{16}$, $NR_{17}R_{18}$, $COR_{14}$, or

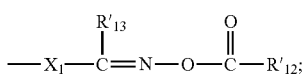

or $R_{19}$ is $C_1$-$C_6$alkylene or $C_2$-$C_6$alkenylene linked to the phenyl or naphthyl ring of the carbazole moiety and forming a 5- or 6-membered saturated or unsaturated ring.

Or $R_{19}$ for example is $C_1$-$C_{20}$alkyl, $C_1$-$C_4$haloalkyl, phenyl-$C_1$-$C_4$alkyl, $C_3$-$C_8$cycloalkyl or phenyl which is unsubstituted or substituted by one or more $C_1$-$C_{20}$alkyl.

In particular $R_{19}$ is $C_1$-$C_{20}$alkyl.

$R_{20}$, $R_{21}$, $R_{22}$, $R_{23}$, $R_{24}$, or $R_{25}$ for example independently of each other are hydrogen; or one of $R_{21}$ and $R_{22}$, or $R_{24}$ and $R_{25}$ is

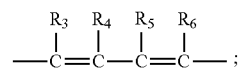

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system.

Or $R_{20}$, $R_{21}$, $R_{22}$, $R_{23}$, $R_{24}$, or $R_{25}$ for example independently of each other are hydrogen, or one of $R_{21}$ and $R_{22}$, or $R_{24}$ and $R_{25}$ is

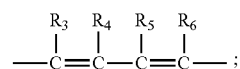

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system.

In particular $R_{20}$, $R_{21}$, $R_{22}$, $R_{23}$, $R_{24}$, or $R_{25}$ for example independently of each other are hydrogen, or one of $R_{21}$ and $R_{22}$, or $R_{24}$ and $R_{25}$ is

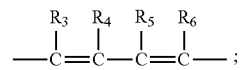

or $R_{20}$ and $R_{23}$ together with $X_3$ and the phenyl rings to which they are attached form a heteroaromatic ring system.

$R_{28}$ and $R_{29}$ for example independently of each other are $C_1$-$C_{20}$alkyl; or $R_{28}$ and $R_{29}$ together with N-atom to which they are attached form a morpholino ring.

$R_{31}$, $R_{32}$, $R_{33}$, $R_{34}$, $R_{35}$, $R_{36}$, $R_{37}$ and $R_{38}$ for example independently of each other are hydrogen,

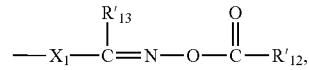

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl; or $R_{33}$ and $R_{34}$ or $R_{35}$ and $R_{36}$ or both, $R_{33}$ and $R_{34}$ and $R_{35}$ and $R_{36}$ are

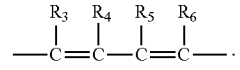

Or $R_{31}$, $R_{32}$, $R_{33}$, $R_{34}$, $R_{35}$, $R_{36}$, $R_{37}$ and $R_{38}$ for example independently of each other are hydrogen,

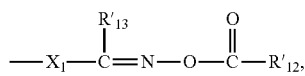

$NO_2$ or $COR_{14}$; or $R_{33}$ and $R_{34}$ or $R_{35}$ and $R_{36}$ or both, $R_{33}$ and $R_{34}$ and $R_{35}$ and $R_{36}$ are

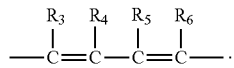

Or $R_{31}$, $R_{32}$, $R_{33}$, $R_{34}$, $R_{35}$, $R_{36}$, $R_{37}$ and $R_{38}$ for example independently of each other are hydrogen,

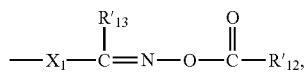

$NO_2$ or $COR_{14}$; or $R_{33}$ and $R_{34}$ or $R_{35}$ and $R_{36}$ are

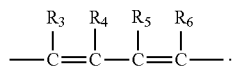

Or for example $R_{31}$, $R_{33}$, $R_{34}$, $R_{35}$, $R_{36}$, $R_{37}$ and $R_{38}$ for example independently of each other are hydrogen or

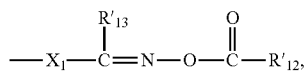

and $R_{32}$ is $NO_2$ or $COR_{14}$; or $R_{33}$ and $R_{34}$ or $R_{35}$ and $R_{36}$ are

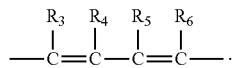

In particular $R_{31}$, $R_{32}$, $R_{33}$, $R_{34}$, $R_{35}$, $R_{36}$, $R_{37}$ and $R_{38}$ for example independently of each other are hydrogen or

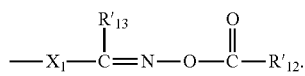

Preferably In particular $R_{31}$, $R_{32}$, $R_{33}$, $R_{34}$, $R_{35}$, $R_{36}$ and $R_{38}$ are hydrogen and $R_{37}$ is

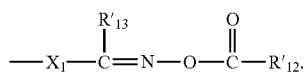

Oxime esters of formula I are prepared by methods described in the literature, for example by reaction of the corresponding oximes with an acyl halide, in particular a chloride, or an anhydride in an inert solvent such as for example t-butyl methyl ether, tetrahydrofurane (THF) or dimethylformamide in the presence of a base, for example triethylamine or pyridine, or in a basic solvent such as pyridine. As example in the following the preparation of compounds of the formula I, wherein $R_2$ is the oxime ester group and X is a direct bond is described:

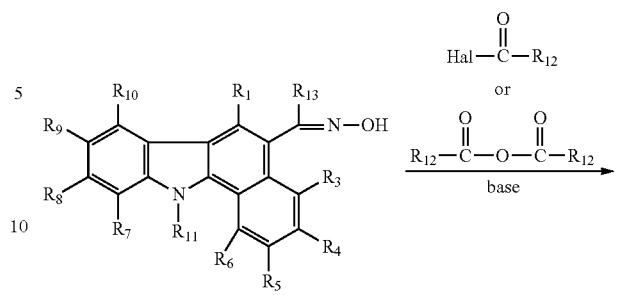

$R_1$, $R_3$, $R_4$, $R_5$, $R_6$, $R_7$, $R_8$, $R_9$, $R_{10}$, $R_{11}$ and $R_{12}$ are as defined above, Hal means a halogen atom, in particular Cl.

$R_{12}$ preferably is methyl.

Such reactions are well known to those skilled in the art, and are generally carried out at temperatures of −15 to +50° C., preferably 0 to 25° C.

When X is CO, the corresponding oxime is synthesized by the nitrosation of the methylene group with an alkyl nitrite such as for example methyl nitrite, ethyl nitrite, isopropyl nitrite, butyl nitrite or isoamyl nitrite. Then, the esterification is carried out under the same condition as mentioned above:

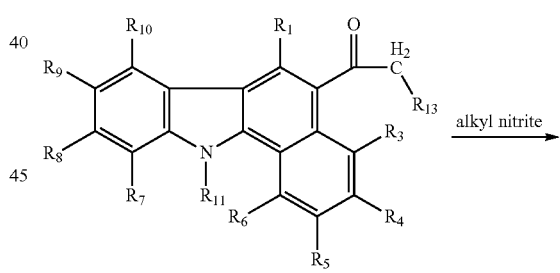

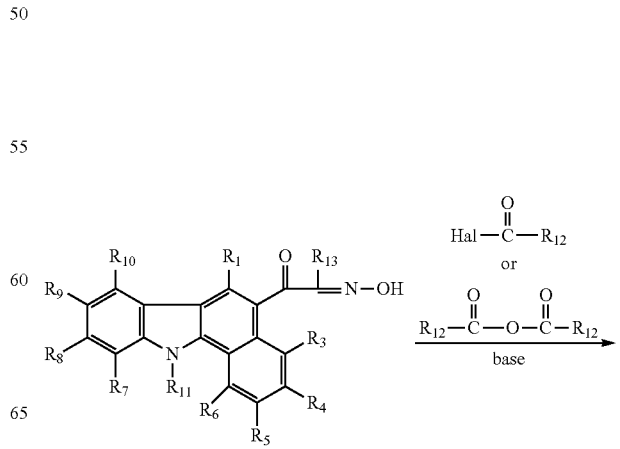

-continued

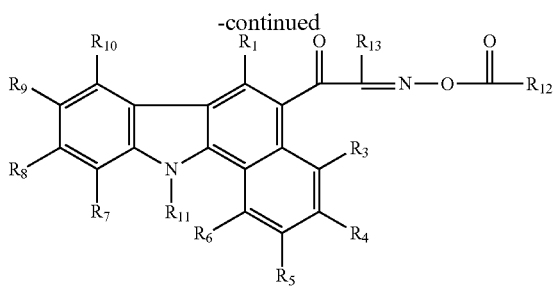

Subject of the invention therefore also is a process for the preparation of a compound of the formula I as defined above by reacting the corresponding oxime compound with an acyl halide of the formula II or an anhydride of the formula III

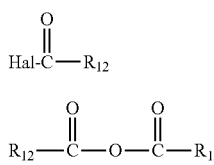

wherein Hal is a halogen, in particular Cl, and $R_{12}$ is as defined above, in the presence of a base or a mixture of bases.

The oximes required as starting materials can be obtained by a variety of methods described in standard chemistry textbooks (for instance in J. March, Advanced Organic Chemistry, 4th Edition, Wiley Interscience, 1992), or in specialized monographs, for example, S. R. Sandler & W. Karo, Organic functional group preparations, Vol. 3, Academic Press.

One of the most convenient methods is, for example, the reaction of aldehydes or ketones with hydroxylamine or its salt in polar solvents like dimethylacetamide (DMA), aqueous DMA, ethanol or aqueous ethanol. In that case, a base such as sodium acetate or pyridine is added to control the pH of the reaction mixture. It is well known that the rate of the reaction is pH-dependent, and the base can be added at the beginning or continuously during the reaction. Basic solvents such as pyridine can also be used as base and/or solvent or cosolvent. The reaction temperature is generally from room temperature to the refluxing temperature of the mixture, usually about 20-120° C.

The corresponding ketone intermediates are for example prepared by the methods described in the literature, for example in standard chemistry textbooks (for instance in J. March, Advanced Organic Chemistry, 4th Edition, Wiley Interscience, 1992). In addition, successive Friedel-Crafts reaction is effective for synthesis of the intermediates. Such reactions are well known to those skilled in the art.

Another convenient synthesis of oximes is the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis coll. vol V, pp 32 and 373, coll. vol. III, pp 191 and 513, coll. vol. II, pp. 202, 204 and 363, are suitable for the preparation of the oximes used as starting materials in the invention. Nitrous acid is usually generated from sodium nitrite. The alkyl nitrite can be for example methyl nitrite, ethyl nitrite, isopropyl nitrite, butyl nitrite, or isoamyl nitrite.

Another embodiment of the invention are the free oxime compounds of the formula (IA)

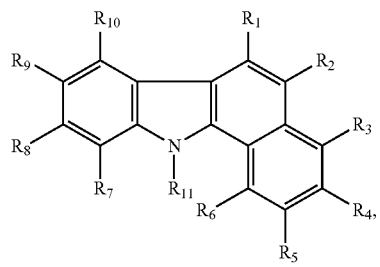

wherein
$R_1$, $R_2$, $R_3$, $R_4$, $R_5$, $R_6$, $R_7$, $R_8$, $R_9$, $R_{10}$ and $R_{11}$ are as defined above, provided that at least one group

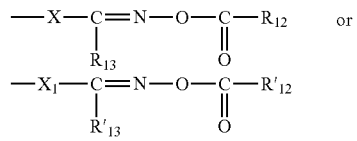

is replaced by a group

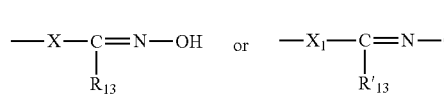

The preferences for the radicals defined for the compounds of the formula (IA) correspond to the ones as given for the compounds of the formula (I) as given in the remaining context of the description, except that defined oxime ester groups are exchanged by the corresponding free oxime radical.

Every oxime ester group can exist in two configurations, (Z) or (E). It is possible to separate the isomers by conventional methods, but it is also possible to use the isomeric mixture as such as photoinitiating species. Therefore, the invention also relates to mixtures of configurational isomers of compounds of the formula I.

Interesting are compounds of the formula I, wherein $R_9$ is

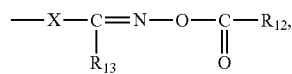

$R_2$ is $COR_{14}$ and
$R_{14}$ is

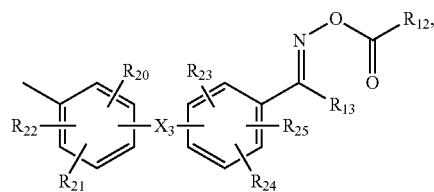

namely compounds of the formula IV:

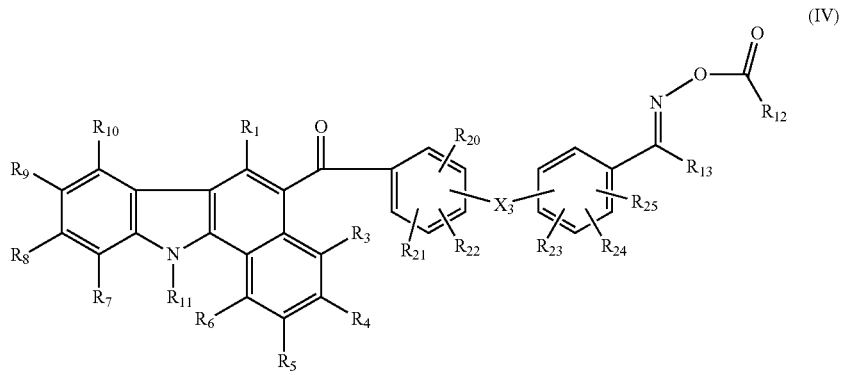

wherein and $R_1$, $R_3$, $R_4$, $R_5$, $R_6$, $R_7$, $R_8$, $R_{10}$, $R_{11}$, $R_{12}$, $R_{20}$, $R_{21}$, $R_{22}$, $R_{23}$, $R_{24}$, $R_{25}$ and $X_3$, are as defined above.

Further interesting are compounds of the formula I, wherein
$R_2$ is $COR_{14}$,
$R_9$ is

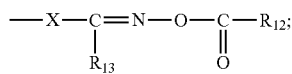

$R_{13}$ is a radical as defined above, substituted by M;
$R_{14}$ is $C_6$-$C_{20}$aryl, which is unsubstituted or substituted as defined above;
M is

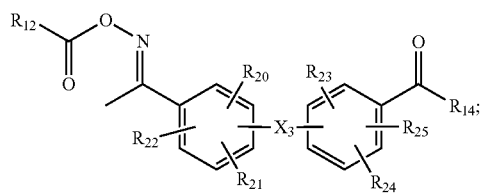

namely compounds of the formula V:

in particular Y is $C_6$-$C_{20}$arylene or $C_3$-$C_{20}$heteroarylene each of which is unsubstituted or substituted by one or more phenyl, halogen, $C_1$-$C_4$haloalkyl, CN, $NO_2$, $OR_{15}$, $NR_{17}R_{18}$, $PO(OC_kH_{2k+1})_2$, $SO$—$C_1$-$C_{10}$alkyl, $SO_2$—$C_1$-$C_{10}$alkyl, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$, or by $NR_{17}R_{18}$;
or Y is $C_1$-$C_{20}$alkylene which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $NR_{17}R_{18}$, $COOR_{15}$, $CONR_{17}R_{18}$, $PO(OC_kH_{2k+1})_2$,

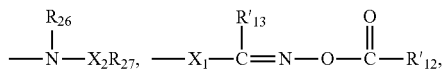

or by phenyl,
or Y is $C_2$-$C_{20}$alkylene which is interrupted by one or more O, CO, S, C(O)O, OC(O), phenylene, naphthylene or $NR_{19}$, wherein the interrupted $C_2$-$C_{20}$alkylene is unsubstituted or substituted by one or more halogen, $OR_{15}$, $COOR_{15}$, $CONR_{17}R_{18}$, phenyl, or by phenyl which is substituted by $OR_{15}$, $SR_{16}$ or $NR_{17}R_{18}$;

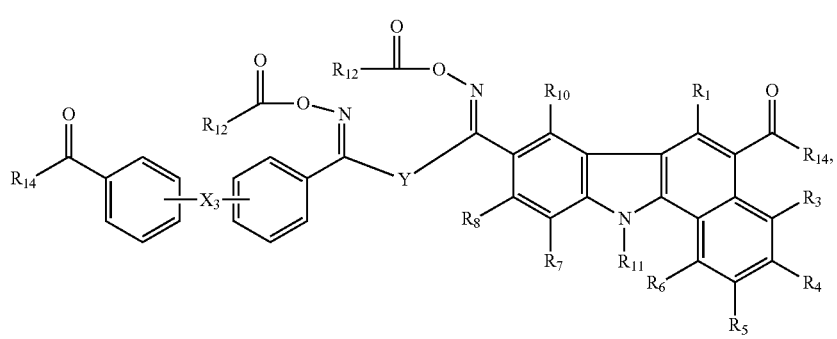

wherein Y is the radical derived from $R_{13}$, which is substituted by M, and $R_1$, $R_3$, $R_4$, $R_5$, $R_6$, $R_7$, $R_8$, $R_{10}$, $R_{11}$, $R_{12}$, $R_{14}$, $R_{20}$, $R_{21}$, $R_{22}$, $R_{23}$, $R_{24}$, $R_{25}$ and $X_3$, are as defined above.

Other interesting compounds are compounds of the formula I, wherein $R_2$ is $COR_{14}$ or $$-X-\underset{R_{13}}{C}=N-O-\underset{O}{\overset{\|}{C}}-R_{12};$$

$R_9$ is $$-X-\underset{R_{13}}{C}=N-O-\underset{O}{\overset{\|}{C}}-R_{12},$$

$R_{11}$ is as defined above, in particular $C_1$-$C_{20}$alkyl which is unsubstituted or substituted by one or more halogen or M;

or $R_{11}$ is $C_2$-$C_{20}$alkyl which is interrupted by one or more O, CO, S, C(O)O, OC(O), phenylene, naphthylene or $NR_{19}$, wherein the interrupted $C_1$-$C_{20}$alkyl is unsubstituted or substituted by one or more halogen, $OR_{15}$, $SR_{16}$, $COOR_{15}$, $CONR_{17}R_{18}$, $NR_{17}R_{18}$ or M;

or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, M, $$-X_1-\underset{R'_{13}}{C}=N-O-\underset{O}{\overset{\|}{C}}-R'_{12};$$

namely compounds of the formula VI:

(VI)

<chemical structure> wherein $R_2$ is $COR_{14}$ or $$-X-\underset{R_{13}}{C}=N-O-\underset{O}{\overset{\|}{C}}-R_{12};$$

$R_1$, $R_3$, $R_4$, $R_5$, $R_6$, $R_7$, $R_8$, $R_{10}$, $R_{11}$, $R_{12}$ and $R_{13}$ are as defined above.

Preferred are Compounds of the formula I as defined above, wherein $R_1$, $R_2$, $R_3$, $R_4$, $R_5$, $R_6$, $R_7$, $R_8$, $R_9$, and $R_{10}$ independently of each other are hydrogen, $C_1$-$C_{20}$alkyl, $$-X-\underset{R_{13}}{C}=N-O-\underset{O}{\overset{\|}{C}}-R_{12}$$

or $COR_{14}$;

provided that at least one of $R_1$, $R_2$, $R_3$, $R_4$, $R_5$, $R_6$, $R_7$, $R_8$, $R_9$ and $R_{10}$ is $$-X-\underset{R_{13}}{C}=N-O-\underset{O}{\overset{\|}{C}}-R_{12}$$

and provided that at least one of the remaining $R_1$, $R_2$, $R_3$, $R_4$, $R_5$, $R_6$, $R_7$, $R_8$, $R_9$, and $R_{10}$ is $COR_{14}$;

X is CO or a direct bond;

$R_{11}$ is $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$, $PO(OC_kH_{2k+1})_2$, or M;

or $R_{11}$ is $C_2$-$C_{20}$alkyl which is interrupted by one or more O, CO, S, C(O)O, OC(O), phenylene, naphthylene or $NR_{19}$, wherein the interrupted $C_1$-$C_{20}$alkyl is unsubstituted or substituted by one or more halogen, $OR_{15}$, $SR_{16}$, $COOR_{15}$, $CONR_{17}R_{18}$, $NR_{17}R_{18}$, or M;

or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, M, $$-X-\underset{R'_{13}}{C}=N-O-\underset{O}{\overset{\|}{C}}-R'_{12},$$

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

$R_{12}$ is $C_1$-$C_{20}$alkyl, phenyl, or $C_1$-$C_8$alkoxy;

$R_{13}$ is phenyl, naphthyl, or $C_3$-$C_{20}$heteroaryl each of which is unsubstituted or substituted by one or more phenyl, halogen, $C_1$-$C_4$haloalkyl, $OR_{15}$, $SR_{16}$, $NR_{17}R_{18}$, M, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_4$-$C_{20}$heteroaryl, $C_6$-$C_{20}$aryloxycarbonyl, $C_4$-$C_{20}$heteroaryloxycarbonyl, $OR_{15}$, $SR_{16}$, $NR_{17}R_{18}$ or by M;

or $R_{13}$ is $C_1$-$C_{20}$alkyl which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $NR_{17}R_{18}$, $COOR_{15}$, $CONR_{17}R_{18}$, $PO(OC_kH_{2k+1})_2$, phenyl or by M, or $R_{13}$ is $C_1$-$C_{20}$alkyl which is substituted by phenyl which is substituted by halogen, $C_1$-$C_{20}$alkyl, $C_1$-$C_4$haloalkyl, $OR_{15}$, $SR_{16}$ or by $NR_{17}R_{18}$;

or $R_{13}$ is $C_2$-$C_{20}$alkyl which is interrupted by one or more O, CO, S, C(O)O, OC(O), phenylene, naphthylene, or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, M, or by phenyl which is substituted by $OR_{15}$, $SR_{16}$ or $NR_{17}R_{18}$;

M is

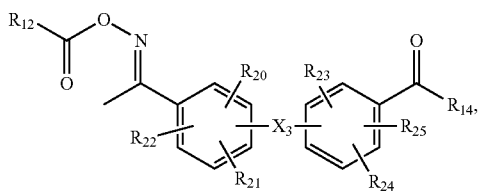

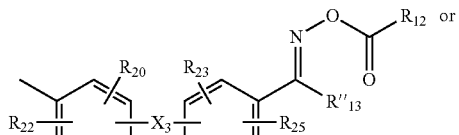

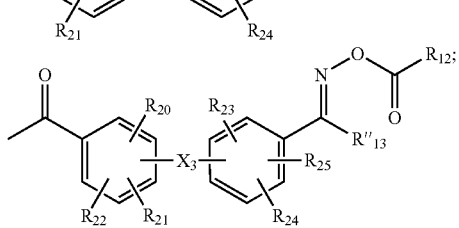

k is an integer 1-10;
m is 1 or 2;
R'$_{12}$ has one of the meanings as given for R$_{12}$;
R'$_{13}$ has one of the meanings as given for R$_{13}$;
R''$_{13}$ is C$_1$-C$_{20}$alkyl which is unsubstituted or substituted by phenyl or by phenyl which is substituted by halogen, C$_1$-C$_{20}$alkyl, C$_1$-C$_4$haloalkyl, OR$_{15}$, SR$_{16}$ or by NR$_{17}$R$_{18}$;
or R''$_{13}$ is C$_2$-C$_{20}$alkyl which is interrupted by one or more O, CO, S, C(O)O, OC(O), phenylene, naphthylene or NR$_{19}$, wherein the interrupted C$_2$-C$_{20}$alkyl is unsubstituted or substituted by one or more halogen, OR$_{15}$, COOR$_{15}$, CONR$_{17}$R$_{18}$, phenyl, or by phenyl which is substituted by OR$_{15}$, SR$_{16}$ or NR$_{17}$R$_{18}$;
or R''$_{13}$ is CN, CONR$_{17}$R$_{18}$, NO$_2$ or C$_1$-C$_4$haloalkyl;
R'''$_{13}$ is C$_6$-C$_{20}$aryl, in particular phenyl or naphthyl, each of which is unsubstituted or substituted by one or more OR$_{15}$, SR$_{16}$, NR$_{17}$R$_{18}$, or each of which is substituted by one or more C$_1$-C$_{20}$alkyl;
X$_1$ is O, CO, S or a direct bond;
X$_3$ is O, S or NR$_{19}$;
R$_{14}$ is phenyl, naphthyl, or C$_3$-C$_{20}$heteroaryl each of which is unsubstituted or substituted by one or more OR$_{15}$, SR$_{16}$, NR$_{17}$R$_{18}$, M or by C$_2$-C$_{20}$alkyl which is interrupted by one or more O, S, or NR$_{19}$, or each of which is substituted by one or more C$_1$-C$_{20}$alkyl which is unsubstituted or substituted by one or more halogen, COOR$_{15}$, CONR$_{19}$R$_{20}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or NR$_{17}$R$_{18}$;
or R$_{14}$ is

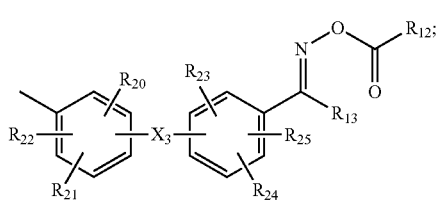

R$_{15}$ is hydrogen, phenyl-C$_1$-C$_3$alkyl, C$_1$-C$_{20}$alkyl which is unsubstituted or substituted by one or more halogen, OCH$_2$CH$_2$CN, OCH$_2$CH$_2$(CO)O(C$_1$-C$_4$alkyl), O(CO)—(C$_1$-C$_4$alkyl), O(CO)—(C$_2$-C$_4$)alkenyl, O(CO)-phenyl, (CO)OH, (CO)O(C$_1$-C$_4$alkyl), C$_3$-C$_{20}$cycloalkyl, SO$_2$—(C$_1$-C$_4$haloalkyl), O(C$_1$-C$_4$haloalkyl), O(C$_1$-C$_{20}$arylene)-M, or by C$_3$-C$_{20}$cycloalkyl which is interrupted by one or more O;
or R$_{15}$ is C$_2$-C$_{20}$alkyl which is interrupted by one or more O, S or NR$_{19}$; R$_{16}$ is methyl substituted by COOR$_{15}$;
or R$_{16}$ is phenyl unsubstituted or substituted by one or more C$_1$-C$_{12}$alkyl, C$_1$-C$_{12}$alkoxy, or

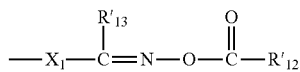

R$_{17}$ and R$_{18}$ independently of each other are hydrogen, phenyl, C$_1$-C$_{20}$alkyl, C$_1$-C$_8$alkanoyl, C$_1$-C$_8$alkanoyloxy;
or R$_{17}$ and R$_{18}$ together with the N-atom to which they are attached form a heteroaromatic ring system which is uninterrupted or is interrupted by

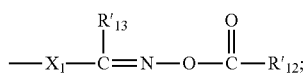

or R$_{17}$ and R$_{18}$ together with the N-atom to which they are attached form a group

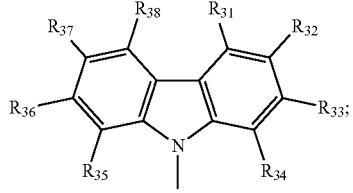

R$_{19}$ is hydrogen, C$_1$-C$_{20}$alkyl, or C$_2$-C$_{20}$alkyl which is interrupted by one or more O or CO;
or R$_{19}$ is phenyl or naphthyl both of which are unsubstituted or substituted by one or more C$_1$-C$_{20}$alkyl, halogen, C$_1$-C$_4$haloalkyl, OR$_{15}$, SR$_{16}$, NR$_{17}$R$_{18}$, COR$_{14}$, or

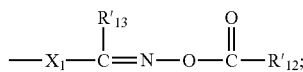

R$_{20}$, R$_{21}$, R$_{22}$, R$_{23}$, R$_{24}$, or R$_{25}$ independently of each other is hydrogen, COR$_{14}$, NO$_2$,

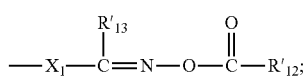

or one of R$_{21}$ and R$_{22}$ or R$_{24}$ and R$_{25}$ is

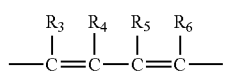

or one of R$_{20}$, R$_{21}$ or R$_{22}$ and one of R$_{23}$, R$_{24}$ or R$_{25}$ together with X$_3$ and the phenyl rings to which they are attached form a heteroaromatic ring system which is unsubstituted or substituted by one or more $C_1$-$C_{20}$alkyl, $C_1$-$C_{20}$alkoxy, $OR_{15}$, $SR_{16}$, $NR_{17}R_{18}$, $COR_{14}$,

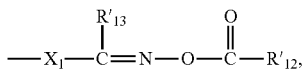

$NO_2$, phenyl;

$R_{31}$, $R_{32}$, $R_{33}$, $R_{34}$, $R_{35}$, $R_{36}$, $R_{37}$ and $R_{38}$ independently of each other are hydrogen,

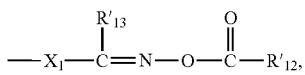

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl which is uninterrupted or is interrupted by one or more O, S, CO or $NR_{19}$;

or $R_{33}$ and $R_{34}$ or $R_{35}$ and $R_{36}$ or both, $R_{33}$ and $R_{34}$ and $R_{35}$ and $R_{36}$ are

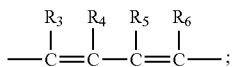

provided that at least two oxime ester groups are present in the molecule.

Further interesting are Compounds of the formula I as described above, wherein $R_1$, $R_2$, $R_3$, $R_4$, $R_5$, $R_6$, $R_7$, $R_8$, $R_9$ and $R_{10}$ independently of each other are hydrogen,

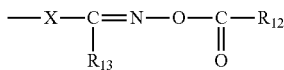

or $COR_{14}$;

provided that at least one of $R_1$, $R_2$, $R_3$, $R_4$, $R_5$, $R_6$, $R_7$, $R_8$, $R_9$, and $R_{10}$ is

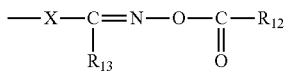

and provided that at least one of the remaining $R_1$, $R_2$, $R_3$, $R_4$, $R_5$, $R_6$, $R_7$, $R_8$, $R_9$, and $R_{10}$ is $COR_{14}$;

X is a direct bond;

$R_{11}$ is $C_1$-$C_{20}$alkyl which is unsubstituted or substituted by $NR_{17}R_{18}$;

or $R_{11}$ is $C_2$-$C_{20}$alkyl which is interrupted by one or more C(O)O, OC(O) or phenylene, wherein the interrupted $C_1$-$C_{20}$alkyl is unsubstituted or substituted by $NR_{17}R_{18}$;

or $R_{11}$ is phenyl or thienyl each of which is unsubstituted or substituted by

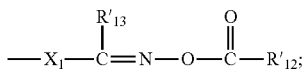

$R_{12}$ is $C_1$-$C_{20}$alkyl;

$R_{13}$ is phenyl or thienyl each of which is unsubstituted or substituted by one or more $OR_{15}$, $SR_{16}$, $NR_{17}R_{18}$, or is substituted by one or more $C_1$-$C_{20}$alkyl;

or $R_{13}$ is $C_1$-$C_{20}$alkyl which is unsubstituted or substituted by $C_3$-$C_8$cycloalkyl, $COOR_{15}$

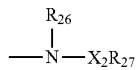

or by M;

M is

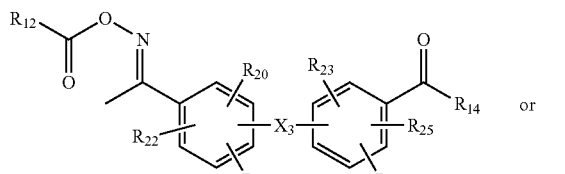

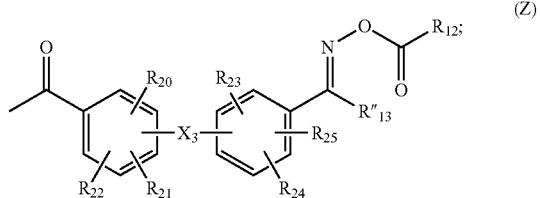

$R'_{12}$ has one of the meanings as given for $R_{12}$,
$R'_{13}$ has one of the meanings as given for $R_{13}$,
$R''_{13}$ is $C_1$-$C_{20}$alkyl, phenyl or thienyl, wherein the phenyl or thienyl is unsubstituted or substituted by $C_1$-$C_{20}$alkyl;
$X_1$ is a direct bond;
$X_2$ is O;
$X_3$ is $NR_{19}$;
$R_{14}$ is phenyl or thienyl each of which is unsubstituted or substituted by one or more $OR_{15}$, $SR_{16}$, $NR_{17}R_{18}$ or $C_1$-$C_{20}$alkyl;
or $R_{14}$ is

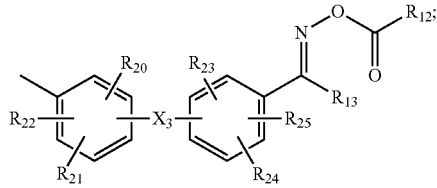

$R_{15}$ is $C_1$-$C_{20}$alkyl which is unsubstituted or substituted by one or more halogen or $O(C_1$-$C_{20}$arylene)-M;

or $R_{15}$ is $C_2$-$C_{20}$alkyl which is interrupted by one or more O, which interrupted $C_2$-$C_{20}$alkyl is unsubstituted or substituted by O—$C_6$-$C_{20}$arylene-M;

$R_{16}$ is phenyl substituted by

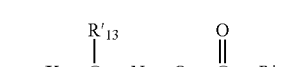

$R_{17}$ and $R_{18}$ together with the N-atom to which they are attached form a group

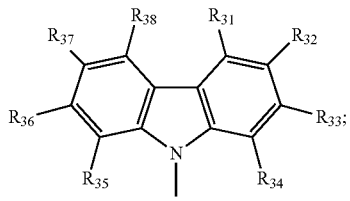

$R_{19}$ is $C_1$-$C_{20}$alkyl;
$R_{20}$, $R_{21}$, $R_{22}$, $R_{23}$, $R_{24}$, or $R_{25}$ independently of each other is hydrogen; or one of $R_{21}$ and $R_{22}$ or $R_{24}$ and $R_{25}$ is

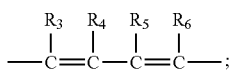

or $R_{20}$ and $R_{23}$ together with $X_3$ and the phenyl rings to which they are attached form a heteroaromatic ring system;
$R_{26}$ is $COOR_{15}$;
$R_{27}$ is $COOR_{15}$;
$R_{31}$, $R_{32}$, $R_{33}$, $R_{34}$, $R_{35}$, $R_{36}$, $R_{37}$ and $R_{38}$ independently of each other are hydrogen,

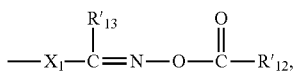

$NO_2$ or $COR_{14}$;
or $R_{33}$ and $R_{34}$ are

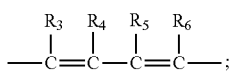

provided that at least two oxime ester groups are present in the molecule.

Emphasis has to be laid on compounds of the formula I as defined above, wherein $R_1$, $R_2$, $R_3$, $R_4$, $R_5$, $R_6$, $R_7$, $R_8$, $R_9$ and $R_{10}$ independently of each other are hydrogen or

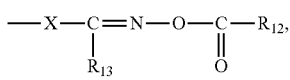

$COR_{14}$;
provided that at least one of $R_1$, $R_2$, $R_3$, $R_4$, $R_5$, $R_6$, $R_7$, $R_8$, $R_9$, and $R_{10}$ is

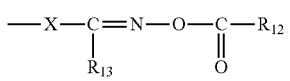

and provided that at least one of the remaining $R_1$, $R_2$, $R_3$, $R_4$, $R_5$, $R_6$, $R_7$, $R_8$, $R_9$, and $R_{10}$ is $COR_{14}$;
X is a direct bond;
$R_{11}$ is $C_1$-$C_{20}$alkyl;
or $R_{11}$ is $C_2$-$C_{20}$alkyl which is interrupted by one or more C(O)O or OC(O), wherein the interrupted $C_2$-$C_{20}$alkyl is substituted by $NR_{17}R_{18}$;

or is phenyl or thienyl each of which is unsubstituted or substituted by

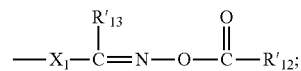

$R_{12}$ is $C_1$-$C_{20}$alkyl;
$R_{13}$ is phenyl or thienyl each of which is unsubstituted or substituted, in particular substituted, by $OR_{15}$, $SR_{16}$, $NR_{17}R_{18}$ or $C_1$-$C_{20}$alkyl;
or $R_{13}$ is $C_1$-$C_{20}$alkyl which is unsubstituted or substituted by $C_3$-$C_8$cycloalkyl, $COOR_{15}$,

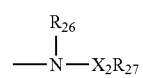

or M;
M is

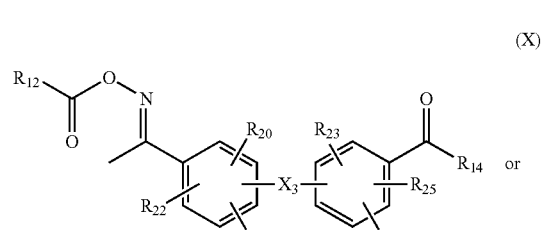

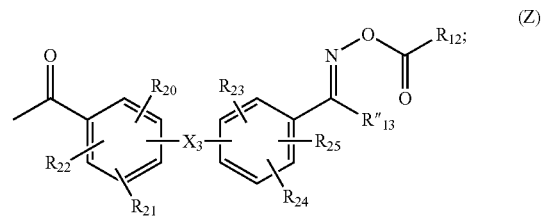

$R'_{12}$ has one of the meanings as given for $R_{12}$; ($C_1$-$C_{20}$alkyl which is unsubstituted)
$R'_{13}$ has one of the meanings as given for $R_{13}$; ($C_1$-$C_{20}$alkyl which is substituted by $COOR_{15}$)
$R''_{13}$ is $C_1$-$C_{20}$alkyl;
or $R''_{13}$ is phenyl or thienyl each of which is unsubstituted or substituted by $C_1$-$C_{20}$alkyl;
$X_1$ is a direct bond;
$X_2$ is O;
$X_3$ is $NR_{19}$;
$R_{14}$ is phenyl or thienyl each of which is unsubstituted or substituted by $OR_{15}$, $SR_{16}$, $NR_{17}R_{18}$ or $C_1$-$C_{20}$alkyl;
or $R_{14}$ is

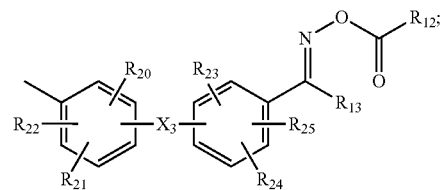

$R_{15}$ is $C_1$-$C_{20}$alkyl which is unsubstituted or substituted by halogen or O($C_1$-$C_{20}$arylene)-M;

or $R_{15}$ is $C_2$-$C_{20}$alkyl which is interrupted by one or more O, which interrupted $C_2$-$C_{20}$alkyl is unsubstituted or substituted by O—$C_6$-$C_{20}$arylene-M;

$R_{16}$ is phenyl which is substituted by

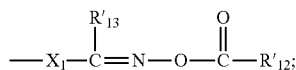

$R_{17}$ and $R_{18}$ together with the N-atom to which they are attached form a group

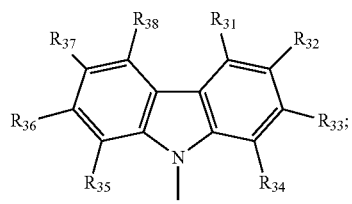

$R_{19}$ is $C_1$-$C_{20}$alkyl;

$R_{20}$, $R_{21}$, $R_{22}$, $R_{23}$, $R_{24}$ or $R_{25}$ independently of each other are hydrogen;

or one of $R_{21}$ and $R_{22}$, or $R_{24}$ and $R_{25}$ is

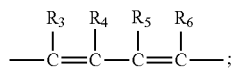

or $R_{20}$ and $R_{23}$ together with $X_3$ and the phenyl rings to which they are attached form a heteroaromatic ring system;

$R_{26}$ is COOR$_{15}$;

$R_{27}$ is COOR$_{15}$;

$R_{31}$, $R_{32}$, $R_{33}$, $R_{34}$, $R_{35}$, $R_{36}$, $R_{37}$ and $R_{38}$ independently of each other are hydrogen,

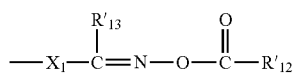

or COR$_{14}$;

or $R_{33}$ and $R_{34}$ are

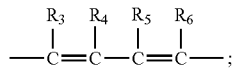

provided that at least two oxime ester groups selected from the group consisting of

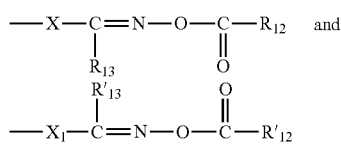

are present in the molecule.

The compounds of the formula I are suitable as radical photoinitiators.

Accordingly, subject of the invention is the use of a compound of the formula (I) as defined above for the photopolymerization of a composition comprising at least one ethylenically unsaturated photopolymerizable compound.

Another subject of the present invention therefore is a photopolymerizable composition comprising (a) at least one ethylenically unsaturated photopolymerizable compound and (b) as photoinitiator, at least one compound of the formula I as defined above.

The composition may comprise additionally to the photoinitiator (b) at least one further photoinitiator (c), and/or other additives (d).

The composition may comprise additionally to the photoinitiator (b) at least one further photoinitiator (c) or other additives (d) or both, at least one further photoinitiator (c) and other additives (d).

The unsaturated compounds (a) may include one or more olefinic double bonds. They may be of low (monomeric) or high (oligomeric) molecular mass. Examples of monomers containing a double bond are alkyl, hydroxyalkyl, cycloalkyl (which optionally interrupted by O) or amino acrylates, or alkyl, hydroxyalkyl, cycloalkyl (which optionally interrupted by O) or amino methacrylates, for example methyl, ethyl, butyl, 2-ethylhexyl or 2-hydroxyethyl acrylate, tetrahydrofurfuryl acrylate, isobornyl acrylate, methyl methacrylate, cyclohexyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, polyesters containing acrylate-, vinyl ether- or epoxy-groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the abovementioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and co-polymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl(meth)acrylates.

Other suitable polymers with acrylate or methacrylate groups in the side chains are, for example, solvent soluble or alkaline soluble polyimide precursors, for example poly(amic acid ester) compounds, having the photopolymerizable side groups either attached to the backbone or to the ester groups in the molecule, i.e. according to EP 624826. Such oligomers or polymers can be formulated with the new photoinitiators and optionally reactive diluents, like polyfunctional (meth)acrylates in order to prepare highly sensitive polyimide precursor resists.

The photopolymerizable compounds can be used alone or in any desired mixtures. It is preferred to use mixtures of polyol (meth)acrylates.

Examples of the component (a) are also polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid, for example, photosensitive compounds as described in JP 6-1638 and JP 10301276 and commercial products such as EB9696, UCB Chemicals; KAYARAD TCR1025, Nippon Kayaku Co., LTD., or an addition product formed between a carboxyl group-containing resin and an unsaturated compound having an α,β-unsaturated double bond and an epoxy group (for example, ACA200M, Daicel Industries, Ltd.).

As diluent, a mono- or multi-functional ethylenically unsaturated compound, or mixtures of several of said compounds, can be included in the above composition up to 70% by weight based on the solid portion of the composition.

Subject of the invention also is a photopolymerizable composition as described above, wherein the component (a) is a resin obtained by the reaction of a saturated or unsaturated polybasic acid anhydride with a product of the reaction of an epoxy resin and an unsaturated monocarboxylic acid.

Such components are for example described in JP06-1938, JP08-278629, JP08-278630, JP10-301276, JP2001-40022, JP10-221843, JP11-231523, JP2002-206014-A or JP2006-53569-A, the disclosure of which hereby is incorporated by reference.

The unsaturated compounds (a) can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10,000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane(meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl(meth)acrylate polymers, are described in EP 41125, and suitable waterdispersible, radiation-curable prepolymers of urethane acrylates can be found in DE 2936039. Further additives which may be included in these radiation-curable aqueous prepolymer dispersions are dispersion auxiliaries, emulsifiers, antioxidants, e.g. 2,2-thiobis(4-methyl-6t-butylphenol) or 2,6-di-t-butylphenol, light stabilizers, dyes, pigments, fillers, such as glass or alumina, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

It is of course also possible to add other known photoinitiators (c), for example mixtures with camphor quinone; benzophenone, benzophenone derivatives, such as for example given below as sensitizers; ketal compounds, as for example benzildimethylketal (Irgacure® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (Darocur® 1173), 1-hydroxy-cyclohexyl-phenylketone (Irgacure® 184), 1-(4-dodecylbenzoyl)-1-hydroxy-1-methylethane, 1-(4-isopropylbenzoyl)-1-hydroxy-1-methyl-ethane, 1-[4-(2-hydroxyethoxy)-phenyl]-2-hydroxy-2-methyl-1-propan-1-one (Irgacure® 2959); 2-hydroxy-1-{4-[4-(2-hydroxy-2-methyl-propionyl)-benzyl]-phenyl}-2-methyl-propan-1-one (Irgacure®127); 2-hydroxy-1-{4-[4-(2-hydroxy-2-methyl-propionyl)-phenoxy]-phenyl}-2-methyl-propan-1-one; 1-[4-(benzoyl-phenyl-thia)phenyl]-2-methyl-2-(p-tolylsulfonyl)-propane-1-one (Esacure® 1001M); oligomeric α-hydroxyalkyl phenyl ketones e.g. Esacure®ONE, Esacure®KIP 100; dialkoxyacetophenones, α-aminoacetophenones, e.g. (4-methylthiobenzoyl)-1-methyl-1-morpholinoethane (Irgacure® 907), (4-morpholinobenzoyl)-1-benzyl-1-dimethylaminopropane (Irgacure® 369), (4-morpholinobenzoyl)-1-(4-methylbenzyl)-1-dimethylaminopropane (Irgacure® 379), (4-(2-hydroxyethyl) aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers, phenylglyoxalic esters and derivatives thereof, e.g. methyl α-oxobenzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (Irgacure® 754); other oximeesters, e.g. 1,2-octanedione 1-[4-(phenylthio)phenyl]-2-(O-benzoyloxime) (Irgacure® OXE01), ethanone 1-[9-ethyl-6-(2-methylbenzoyl)-9H-carbazol-3-yl]-1-(0-acetyloxime) (Irgacure® OXE02), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethylbenzoyl)diphenylphosphine oxide (Darocur® TPO), ethyl (2,4,6 trimethylbenzoyl phenyl)phosphinic acid ester; bisacylphosphine oxides, e.g. bis(2,6-dimethoxy-benzoyl)-(2,4,4-trimethylpentyl)phosphine oxide, bis(2,4,6-trimethylbenzoyl)-phenylphosphine oxide (Irgacure® 819), bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]-triazene, 2-(3,4-dimethoxy-phenyl)-4,6-bis-trichloromethyl[1,3,5]triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrrylphenyl)titanium (Irgacure® 784).

Further, borate compounds can be used as coinitiators. The Darocur® and Irgacure® compounds are available from BASF SE; Esacure is available from Lamberti SPA.

Where the novel photoinitiator systems are employed in hybrid systems, use is made, in addition to the novel free-radical hardeners, of cationic photoinitiators, of peroxide compounds, such as benzoyl peroxide (other suitable peroxides are described in U.S. Pat. No. 4,950,581 column 19, lines 17-25), of aromatic sulfonium-, phosphonium- or iodonium salts as described for example in U.S. Pat. No. 4,950,581, column 18, line 60 to column 19, line 10 or cyclopentadienylarene-iron(II) complex salts, for example ($\eta^6$-iso-propylbenzene)($\eta^5$-cyclopentadienyl)iron(II) hexafluorophosphate, as well as oxime sulfonic acid esters, as are, for example described in EP780729. Also pyridinium and (iso)quinolinium salts as described e.g. in EP497531 and EP441232 may be used in combination with the new photoinitiators.

The new photoinitiators, either alone or in mixtures with other known photoinitiators and sensitizers, can be used also in the form of a dispersion or emulsion in water or aqueous solutions. In case the compounds are used in emulsions or dispersions conveniently customary dispersants or emulsifiers are added to prepare a stable emulsion or dispersion. Corresponding suitable additives are known to the person skilled in the art.

The photopolymerizable compositions generally comprise 0.05 to 25% by weight, preferably 0.01 to 10% by weight, in particular 0.01 to 5% by weight of the photoinitiator, based on the solid composition. The amount refers to the sum of all photoinitiators added, if mixtures of initiators are employed. Accordingly, the amount either refers to the photoinitiator (b) or the photoinitiators (b)+(c).

In addition to the photoinitiator the photopolymerizable mixtures may include various additives (d). Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer on top of the coating, for example poly (vinylalcohol-co-vinylacetate). Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS). Examples of such UV absorbers and light stabilisers are disclosed in WO 04/074328, page 12, line 9 to page 14, line 23, said disclosure hereby is incorporated by reference.

To accelerate the photopolymerization it is possible to add amines as component (d), for example triethanolamine, N-methyldiethanolamine, ethyl-p-dimethylaminobenzoate, 2-(dimethylamino)ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP Kokai Hei 6-68309.

It is further possible to add chain transfer agents which are customary in the art to the compositions according to the invention as component (d). Examples are mercaptans, amines and benzothiazol.

Photopolymerization can also be accelerated by adding further photosensitizers or coinitiators (as component (d)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes. Examples of suitable sensitizer compounds (d) are disclosed in WO 06/008251, page 36, line 30 to page 38, line 8, the disclosure of which is hereby incorporated by reference.

A photopolymerizable composition, comprising as further additive (d) a photosensitizer compound selected from the group consisting of benzophenone and its derivatives, thioxanthone and its derivatives, anthraquinone and its derivatives, or coumarine and its derivatives is preferred.

Examples of benzophenone derivatives, thioxanthone derivatives, anthraquinone derivatives and coumarin derivatives are benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoyl-phenylsulfanyl)-phenyl]-2-methyl-2-(toluene-4-sulfonyl)-propan-1-one, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propenyl)oxy]ethyl-benzenemethanaminium chloride; thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxyarbnylthioxanthone, 3-butoxycarbonyl-7-methylthioxanthone, 1-cyano-3chlorothioxanthone, 1-ethoxycarbonyl-3-chlorothioxanthone, 1-ethoxycarbonyl-3-ethoxythioxanthne, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]-thioxanthone, 1,3-dimethyl-2-hydroxy-9Hthioxanthen-9-one 2-ethylhexylether, 1-ethoxycarbonyl-3-(1-methyl-1-morpholinothyl)-thioxanthone, 2-methyl-6-dimethoxymethyl-thioxanthone, 2-methyl-6-(1,1-dimethxyenzyl)-thioxanthone, 2-morpholinomethylthioxanthone, 2-methyl-6-morpholinoethylhioxanthone, N-allylthioxanthone-3,4-dicarboximide, N-octylthioxanthone-3,4-dicarbximide, N-(1,1,3,3-tetramethylbutyl)-thioxanthone-3,4-dicarboximide, 1-phenoxythioanhone, 6-ethoxycarbonyl-2methoxythioxanthone, 6-ethoxycarbonyl-2-methylthioxanhone, thioxanthone-2-carboxylic acid polyethyleneglycol ester, 2-hydroxy-3-(3,4- dimethyl-9-oxo-9H-thioxanthon-2-yloxy)-N,N,N-trimethyl-1-propanaminium chloride, couarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-di methoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxycoumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin, 9,10-anthraquinone and anthracene.

The curing process can be assisted by adding photosensitizers, in particular, in compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP245639.

The compositions according to the invention may comprise as further additive (d) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP445624.

Further additives known in the art may be added as component (d), as for example flow improvers, adhesion promoters, such as vinyltrimethoxysilane, vinyltriethoxysilane vinyltris(2-methoxyethoxy)silane, N-(2-aminoethyl)-3-aminopropylmethyldimethoxysilane, N-(2-aminoethyl)3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane and 3-mercaptopropyltrimethoxysilane. Surfactants, optical brighteners, pigments, dyes, wetting agents, levelling assistants, dispersants, aggregation preventers, antioxidants or fillers are further examples for additives (d).

In order to cure thick and pigmented coatings it is appropriate to add glass microspheres or pulverized glass fibres, as described for example in U.S. Pat. No. 5,013,768.

Further suitable components (d) are, as already mentioned above, surfactants and dispersants and other components, in particular to support the application of pigments or colorants in the formulation.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least one pigment derivative.

Suitable surfactants include anionic surfactants such as alkylbenzene- or alkylnahthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOEISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to 30 parts by weight, based on 100 parts by weight of the colorant composition.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth)acrylamides, and such block co-polymers and/or comb polymers modified by post modification; polyethylenimines, which for instance is crafted with polyesters; polyamines, which for instance is crafted with polyesters; and many kinds of (modified) polyurethanes. Polymeric dispersants may also be employed. Suitable polymeric dispersants are, for example, BYK's DISPERBYK® 101, 115, 130, 140, 160, 161, 162, 163, 164, 166, 168, 169, 170, 171, 180, 182, 2000, 2001, 2009, 2020, 2025, 2050, 2070, 2090, 2091, 2095, 2096, 2150, 2163, 2164, BASFs EFKA® 4008, 4009, 4010, 4015, 4020, 4046, 4047, 4050, 4055, 4060, 4061, 4080, 4300, 4310, 4320, 4330, 4340, 4400, 4401, 4402, 4403, 4406, 4500, 4510, 4520, 4530, 4540, 4550, 4560, 4570, 4580, 4585, 4590, 4800, Ajinomoto Fine Techno's Ajisper PB®711, 821, 822, 823, 824, 827, 881, Lubrizol's SOLSPERSE® 1320, 13940, 17000, 20000, 21000, 24000, 26000, 27000, 28000, 31845, 32000, 32500, 32550, 32600, 33500, 34750, 36000, 36600, 37500, 38500, 39000, 41000, 41090, 44000, 53095, Kawaken Fine Chemicals' Hinoact KF-1300M, T-6000, T-8000, T-8000E, T-9050, Kusumoto Chemicals' Disparlon PW-36, DA-325, DA-375, DA-7301, Kyoheisha Chemical's Flowlen DOPA-15B, DOPA-15BHFS, DOPA-17HF, DOPA-22, DOPA-33, G-600, G-700, G-820, G-900, NC-500, KDG-2400 and combinations thereof.

It is preferred to use EFKA® 4046, 4047, 4060, 4061, 4300, 4310, 4320, 4330, 4340, 4585, DISPERBYK® 161, 162, 163, 164, 165, 166, 168, 169, 170, 2000, 2001, 2020, 2050, 2090, 2091, 2095, 2096, 2105, 2150, 2163, 2164, PB®711, 821, 822, 823, 824, 827, 881, SOLSPERSE®

24000, 31845, 32500, 32550, 32600, 33500, 34750, 36000, 36600, 37500, 39000, 41090, 44000, 53095, Hinoact T-6000, T-8000E, Disparlon PW-36, DA-7301, and combinations thereof as dispersant.

Suitable texture improving agents are, for example, fatty acids such as stearic acid or behenic acid, and fatty amines such as laurylamine and stearylamine. In addition, fatty alcohles or ethoxylated fatty alcohles polyols such as aliphatic 1,2-diols or epoxidized soy bean oil, waxes, resin acids and resin acid salts may be used for this purpose.

Suitable pigment dispersants are, for example, copper phthalocyanine derivatives such as BASF's EFKA® 6745, Lubrizol's SOLSPERSE® 5000, 12000, BYK's SYNERGIST 2100 and azo derivatives such as EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive (d) comprising a dispersant or a mixture of dispersants as well as a photopolymerizable composition as described above as further additive (d) comprising a pigment or a mixture of pigments or a mixture of one or more pigments with one or more dyes.

The choice of additive(s) (d) is made depending on the field of application and on properties required for this field. The additives described above are customary in the art and accordingly are added in amounts which are usual in the respective application.

Binders (e) as well can be added to the novel compositions. This is particularly expedient when the photopolymerizable compounds are liquid or viscous substances. The quantity of binder may, for example, be 2-98%, preferably 5-95% and especially 20-90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 2,000 to 2,000,000, preferably 3,000 to 1,000,000. Examples of alkali developable binders are acrylic polymer having carboxylic acid function as a pendant group, such as conventionally known copolymers obtained by copolymerizing an ethylenic unsaturated carboxylic acid such as (meth)acrylic acid, 2-carboxyethyl (meth)acrylic acid, 2-carboxypropyl(meth)acrylic acid itaconic acid, crotonic acid, maleic acid, fumaric acid and ω-carboxypolycaprolactone mono(meth)acrylate, with one or more monomers selected from esters of (meth)acrylic acid, such as methyl(meth)acrylate, ethyl(meth)acrylate, propyl(meth)acrylate, butyl(meth)acrylate, benzyl(meth)acrylate, 2-ethylhexyl(meth)acrylate, hydroxyethyl(meth)acrylate, hydroxypropyl(meth)acrylate, glycerol mono(meth)acrylate, tricyclo[5.2.1.0$^{2,6}$]decan-8-yl(meth)acrylate, glycidyl(meth) acrylate, 2-methylglycidyl(meth)acrylate, 3,4-epoxybutyl (meth)acrylate, 6,7-epoxyheptyl(meth)acrylate; vinyl aromatic compounds, such as styrene, α-methylstyrene, vinyltoluene, p-chlorostyrene, vinyl benzyl glycidyl ether; amide type unsaturated compounds, (meth)acrylamide diacetone acrylamide, N-methylolacrylamide, N-butoxymethacrylamide; and polyolefin type compounds, such as butadiene, isoprene, chloroprene and the like; methacrylonitrile, methyl isopropenyl ketone, mono-2-[(meth)acryloyloxy]ethyl succinate, N-phenylmaleimide, maleic anhydride, vinyl acetate, vinyl propionate, vinyl pivalate, polystyrene macromonomer, or polymethyl(meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferable examples of copolymers are copolymers of methyl methacrylate/methacrylic acid, co-polymers of benzyl methacrylate/methacrylic acid, copolymers of methyl methacrylate/ethyl acrylate/methacrylic acid, copolymers of benzyl methacrylate/methacrylic acid/styrene, copolymers of benzyl methacrylate/methacrylic acid/hydroxyethyl methacrylate, copolymers of methyl methacrylate/butyl methacrylate/methacrylic acid/styrene, copolymers of methyl methacrylate/benzyl methacrylate/methacrylic acid/hydroxyphenyl methacrylate. Examples of solvent developable binder polymers are poly (alkyl methacrylates), poly(alkyl acrylates), poly(benzylmethacrylate-co-hydroxyethylmethacrylate-co-methacrylic acid), poly(benzylmethacrylate-co-methacrylic acid); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), and polyesters such as poly(ethylene glycol terephtalate) and poly(hexamethylene glycol succinate) and polyimide binder resins.

The polyimide binder resin in the present invention can either be a solvent soluble polyimide or a polyimide precursor, for example, a poly(amic acid).

Preferred is a photopolymerizable composition, comprising as binder polymer (e), a copolymer of methacrylate and methacrylic acid.

Interesting further are polymeric binder components as described e.g. in JP 10-171119-A, in particular for use in color filters.

Subject of the invention further is a photopolymerizable composition as described above, wherein the component (a) is a resin obtained by the reaction of a saturated or unsaturated polybasic acid anhydride with a product of the reaction of an epoxy resin and an unsaturated monocarboxylic acid.

The photopolymerizable compositions can be used for various purposes, for example as printing ink, e.g. screen printing inks, inks for offset- or flexo printing, as a clear, white or colored finish, for example for wood, plastic or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists, solder resists, electroplating resists, or permanent resists, both liquid and dry films, as photostructurable dielectric, for printed circuit boards and electronic circuits, as resists to manufacture color filters for a variety of display applications or to generate structures in the manufacturing process of plasma-display panels and electroluminescence displays, (as for example described in U.S. Pat. No. 5,853,446, EP863534, JP 09-244230-A, JP10-62980-A, JP08-171863-A, U.S. Pat. No.

5,840,465, EP855731, JP05-271576-A, JP 05-67405-A) for the production of holographic data storage (HDS) material, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and integrated circuits, or as coatings for optical fibres, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE19700064 and EP678534.

The novel photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator systems, the powder coating formulations may also include UV absorbers. Appropriate examples are listed above in sections 1.-8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

The novel radiation-sensitive compositions further find application as negative resists, having a very high sensitivity to light and being able to be developed in an aqueous alkaline medium without swelling. They are suitable for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

The novel composition also relates to a photosensitive thermosetting resin composition and a method of forming a solder resist pattern by the use thereof, and more particularly relates to a novel photosensitive thermosetting resin composition useful as materials for the production of printed circuit boards, the precision fabrication of metallic articles, the etching of glass and stone articles, the relief of plastic articles, and the preparation of printing plates and particularly useful as a solder resist for printed circuit boards and to a method of forming a solder resist pattern by the steps of exposing a layer of the resin composition selectively to an actinic ray through a photomask having a pattern and developing the unexposed part of the layer.

The solder resist is a substance which is used during the soldering of a given part to a printed circuit board for the purpose of preventing molten solder from adhering to irrelevant portions and protecting circuits. It is, therefore, required to possess such properties as high adhesion, insulation resistance, resistance to soldering temperature, resistance to solvents, resistance to alkalis, resistance to acids, and resistance to plating.

Because the photocurable compositions according to the invention have a good thermal stability and are sufficiently resistant to inhibition by oxygen, they are particularly suitable for the production of color filters or color mosaic systems, such as described, for example, in EP 320 264. Color filters usually are employed in the manufacturing of flat panel displays such as LCD's, PDP (plasma panel display), EL (electroluminessence) display, and projection systems, image sensors, CCD (charge coupled device), and CMOS (complementary metal oxide semiconductor) sensors for scanner, digital camera and video camera.

The color filters usually are prepared by forming red, green and blue pixels and a black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating to actinic radiation and subsequent development of the pattern in an aqueous alkaline developer solution and optionally a heat treatment. Thus, by subsequently applying a red, green and blue pigmented coating, in any desired order, on top of each other with this process a color filter layer with red, green and blue color pixels can be produced.

The development is carried out by washing out the areas which were not polymerized with a suitable alkali developing solution. This process is repeated to form the image having plural colors.

In the light-sensitive resin composition of the present invention, with a process in which at least one or more picture elements are formed on a transparent substrate and then an exposure is given from a side of the transparent substrate, on which the above picture elements are not formed, the above picture elements can be utilized as a light-shielding mask. In this case, for example, in the case where an overall exposure is given, a position adjustment of a mask gets unnecessary and a concern on a position slippage thereof is removed. And, it is possible to cure all of the part on which the above picture elements are not formed. Further, in this case, it is possible as well to develop and remove a part of the portion on which the above picture elements are not formed by using partially a light-shielding mask.

Since in either case, no gap is formed between the picture elements which are formed formerly and those which are formed later, the composition of the present invention is suitable for, for example, a forming material for a color filter. To be concrete, the coloring matters, dyes and pigments of red, green and blue colors are added to the light-sensitive resin composition of the present invention, and the processes for forming an image are repeated to form the picture elements of red, green and blue colors. Then, the light-sensitive resin composition to which, for example, the black coloring materials, dyes and pigments are added is provided on an overall face. An overall exposure (or a partial exposure via a light-shielding mask) can be provided thereon to form the picture elements of a black color all over the spaces (or all but a partial region of the light-shielding mask) between the picture elements of red, green and blue colors.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

A metal support, glass, ceramics, and a synthetic resin film can be used as a support for a color filter. Glass and a synthetic resin film which is transparent and have an excellent dimension stability is particularly preferred.

The thickness of the light-sensitive resin composition layer is usually 0.1 to 50 micrometers, in particular 0.5 to 5 micrometers.

A diluted aqueous solution of an alkaline substance can be used as a developing solution for the light-sensitive resin composition of the present invention if the composition contains alkali soluble resin or alkali soluble monomers or oligomers, and further a developer solution prepared by adding a small amount of a water-miscible organic solvent thereto is included as well.

Examples of suitable alkaline materials include alkali metal hydroxides (for example, sodium hydroxide and potassium hydroxide), alkali metal carbonates (for example, sodium carbonate and potassium carbonate), alkali metal bicarbonates (for example, sodium bicarbonate and potassium bicarbonate), alkali metal silicates (for example, sodium silicate and potassium silicate), alkali metal metasilicates (for example, sodium metasilicate and potassium metasilicate), triethanolamine, diethanolamine, monoethanolamine, morpholine, tetraalkylammonium hydroxides (for example, tetramethylammonium hydroxide), or trisodium phosphate. The concentration of the alkaline substance is 0.01 to 30 weight %, and pH is preferably 8 to 14.

Suitable organic solvents which are miscible with water include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butylolactone, dimethylformamide, dimethylacetoamide, hexamethylphosphoramide, ethyl lactate, methyl lactate, epsilon-caprolactam, and N-methyl-pyrrolidinone. The concentration of the organic solvent which is miscible with water is 0.1 to 30 weight %.

Further, a publicly known surface active agent can be added. The concentration of the surface active agent is preferably 0.001 to 10 weight %.

The light sensitive resin composition of the present invention can also be developed with organic solvents, including blends of two or more solvents, not containing alkaline compounds. Suitable solvents include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butylolactone, dimethylformamide, dimethylacetamide, hexamethylphosphoramide, ethyl lactate, methyl lactate, epsilon-caprolactam, and N-methylpyrrolidinone. Optionally, water can be added to these solvents up to a level at which still a clear solution is obtained and at which sufficient solubility of the unexposed areas of the light sensitive composition is maintained.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 5 to about 60 minutes.

The pigment which can be comprised in the composition according to the present invention, including a pigmented color filter resist composition, is preferably a processed pigment, for example a powdery or pasty product prepared by finely dispersing a pigment into at least one resin selected from the group consisting of acrylic resin, vinyl chloride-vinyl acetate copolymer, maleic acid resin and ethyl cellulose resin.

The red pigment comprises, for example, an anthraquinone type pigment alone, a diketopyrolopyrole type pigment alone, a mixture of them or a mixture consisting of at least one of them and a disazo type yellow pigment or an isoindoline type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177 and C. I. Pigment Red 254, and C. I. Pigment Yellow 83 or C. I. Pigment Yellow 139 ("CI" refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 222, 242, 244, 255, 264, 272 and C.I. Pigment Yellow 12, 13, 14, 17, 20, 24, 31, 53, 55, 93, 95, 109, 110, 128, 129, 138, 139, 150, 153, 154,155, 166, 168, 185, 199, 213 and C.I. Pigment Orange 43.

Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes.

The green pigment comprises for instance a halogenated phthalocyanine type pigment alone or its mixture with a disazo type yellow pigment, an quinophthalone type yellow pigment or a metal complex, in particular C. I. Pigment Green 7 alone, C. I. Pigment Green 36 alone, or a mixture consisting of at least one member of C. I. Pigment Green 7, C. I. Pigment Green 36 and C. I. Pigment Yellow 83, C. I. Pigment Yellow 138 or C. I. Pigment Yellow 150. Other suitable green pigments are C.I. Pigment Green 15, 25 and 37.

Examples for suitable green dyes are C. I. Acid Green 3, 9, 16, C. I. Basic Green 1 and 4.

Examples for suitable blue pigments are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60. Other suitable pigments are C. I. Pigment Violet 14,19, 23, 29, 32, 37, 177 and C. I. Orange 73.

Examples for suitable blue dyes are C. I. Solvent Blue 25, 49, 68, 78, 94, C. I. Direct Blue 25, 86, 90, 108, C. I. Acid Blue 1, 7, 9, 15, 103, 104, 158, 161, C. I. Basic Blue 1, 3, 9, 25, and C. I. Disperse Blue 198.

The pigment of the photopolymeric composition for black matrix preferably comprises at least one member selected from the group consisting of carbon black, titanium black and iron oxide. However, a mixture of other pigments which, in total, give the black appearance, can also be used. For example, also C. I. Pigment Black 1, 7 and 31 can be used alone or in combination.

Other examples of the dyes used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

For any color, combinations of more than two pigments can also be used. Especially suitable in color filter applications are powdery processed pigments prepared by finely dispersing the above mentioned pigments into a resin.

The concentration of the pigment in the total solid component (pigments of various colors and resin) is for example in the range of 5% to 80% by weight, in particular in the range of 20% to 45% by weight.

The pigments in the color filter resist composition have preferably a mean particle diameter smaller than the wavelength of visible light (400 nm to 700 nm). Particularly preferred is a mean pigment diameter of <100 nm.

If necessary, the pigments may be stabilized in the photosensitive composition by pretreatment of the pigments with a dispersant to improve the dispersion stability of the pigment in the liquid formulation. Suitable additives are described above.

Preferably, the color filter resist composition according to the present invention contains additionally at least one addition polymerizable monomeric compound as component (a).

The ethylenically unsaturated compounds (a), also for the color filter resist applications are as described above Suitable examples of esters as component (a) based on polyols are trimethylolpropane tri(meth)acrylate, trimethylolpropane tri(acryloyloxypropyl)ether, trimethylolethane tri(meth)acrylate, ethylene glycol di(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth)acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth)acrylate, dipentaerythritol penta(meth)acrylate, dipentaerythritol hexa(meth)acrylate, dipentaerythritol penta(meth)acrylate mono(2-hydroxyethyl) ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol ditaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

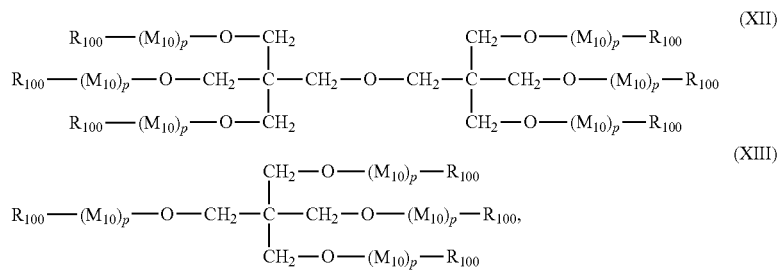

wherein
$M_{10}$ is —(CH$_2$CH$_2$O)— or —[CH$_2$CH(CH$_3$)O]—,
$R_{100}$ is —COCH=CH$_2$ or —COC(CH$_3$)=CH$_2$,
p is 0 to 6 (total of p: 3-24), and q is 0 to 6 (total of q: 2-16).

Examples of polyepoxides are those based on the abovementioned polyols and epichlorohydrin. Typical examples are bis(4-glycidyloxyphenyl)methane, 2,2-bis(4-glycidyloxyphenyl)propane, 2,2-bis(4-glycidyloxyphenyl)hexafluoropropane, 9,9-bis(4-glycidyloxyphenyl)fluorene, bis[4-(2-glycidyloxyethoxy)phenyl]methane, 2,2-bis[4-(2-glycidyloxyethoxy)phenyl]propane, 2,2-bis[4-(2-glycidyloxyethoxy)phenyl]hexafluoropropane, 9,9-bis[4-(2-glycidyloxyethoxy)phenyl]fluorene, bis[4-(2-glycidyloxypropoxy)phenyl]methane, 2,2-bis[4-(2-glycidyloxypropoxy)phenyl]propane, 2,2-bis[4-(2-glycidyloxypropoxy)phenyl]hexafluoropropane, 9,9-bis[4-(2-glycidyloxypropoxy)phenyl]fluorene, and glycidyl ethers of phenol and cresol novolacs.

Typical examples of component (a) based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryloxy)propoxyethoxy}phenyl]fluorine, and reaction products of epoxy resins based on novolacs with (meth)acrylic acid.

Polyethers obtained from the reaction of the abovementioned polyols or polyepoxides with the unsaturated compounds with a hydroxy group such as 2-hydroxyethyl(meth)acrylate, vinyl alcohol can also be used as component (a).

Other examples for suitable components (a) are unsaturated urethanes derived from a polyisocyanate and an unsaturated compound having a hydroxy group or from a polyisocyanate, a polylol and an unsaturated compound having a hydroxy group.

Other examples are polyesters, polyamides, or polyurethanes having ethylenically unsaturated groups in the chain. Suitable unsaturated polyesters and polyamides are also derived, for example, from maleic acid and diols or diamines. Some of the maleic acid can be replaced by other dicarboxylic acids. The polyesters and polyamides may also be derived from dicarboxylic acids and ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Other suitable polymers with acrylate or methacrylate groups in the side chains are, for example, solvent soluble or alkaline soluble polyimide precursors, for example poly(amic acid ester) compounds, having the photopolymerizable side groups either attached to the backbone or to the ester groups in the molecule, i.e. according to EP 624826. Such oligomers or polymers can be formulated optionally with reactive diluents, like polyfunctional (meth)acrylates in order to prepare highly sensitive polyimide precursor resists.

Further examples of the component (a) are also polymers or oligomers having at least one carboxyl function and at least two ethylenically unsaturated groups within the molecular structure, such as a resin obtained by the reaction of a saturated or unsaturated polybasic acid anhydride with a product of the reaction of phenol or cresol novolac epoxy resin and an unsaturated monocarboxylic acid, for example, commercial products such as EB9696, UCB Chemicals; KAYARAD TCR1025, Nippon Kayaku Co., LTD. Examples of the polybasic acid anhydride are maleic anhydride, succinic anhydride, itaconic anhydride, phthalic anhydride, tetrahydrophthalic anhydride, hexahydrophthalic anhydride, methyltetrahydrophathalic anhydride, glutaric anhydride, glutaconic anhydride, citraconic anhydride, diglycolic anhydride, iminodiacetic anhydride, 1,1-cyclopentanediacetic anhydride, 3,3-dimethylglutaric anhydride, 3-ethyl-3-methylglutaric anhydride, 2-phenylglutaric anhydride, homophthalic anhydride, trimellitis anhydride, chlorendic anhydride, pyromellitic dianhydride, benzophenone tetracarboxylic acid dianhydride, biphenyl tetracarboxylic acid dianhydride, and biphenylether tetracarboxylic acid dianhydride.

Other examples are the products from the polycondensation reaction and/or addition reaction of the compound of formula (XIV) with one or more abovementioned polybasic acid anhydrides.

abovementioned binder polymers which are resulting from the reaction of an unsaturated carboxylic acid compound with one or more polymerizable compounds, for example, copolymers of (meth)acrylic acid, benzyl(meth)acrylate, styrene and 2-hydroxyethyl(meth)acrylate, copolymers of (meth)acrylic acid, styrene and α-methystyrene, copolymers of (meth)acrylic acid, N-phenylmaleimide, styrene and benzyl (meth)acrylate, copolymers of (meth)acrylic acid and styrene, copolymers of (meth)acrylic acid and benzyl(meth)

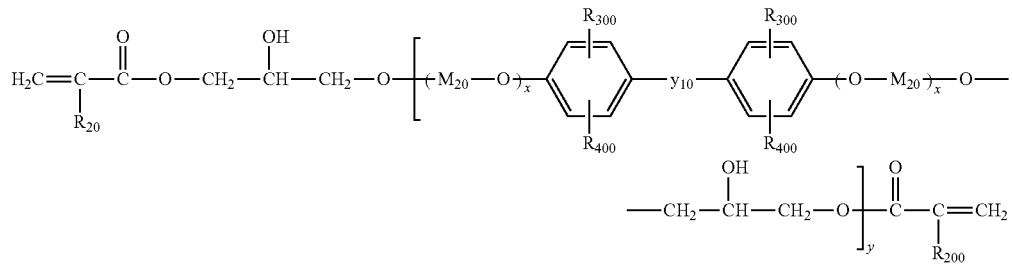

wherein $Y_{10}$ is

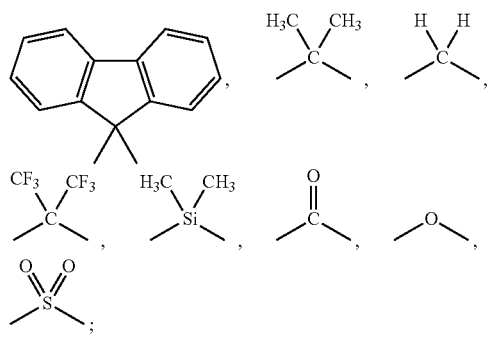

$R_{200}$ is hydrogen or methyl, $R_{300}$ and $R_{400}$ independently of each other are hydrogen, methyl, Cl, or Br, $M_{20}$ is substituted or unsubstituted alkylene having 1 to 10 carbon atoms, x is 0 to 5, and y is 1 to 10. Examples of such compounds as component (a) are described in JP2002-206014A, JP2004-69754A, JP2004-302245A, JP2005-77451 A, JP2005-316449A, JP2005-338328A and JP3754065B2.

Polymers or oligomers as abovementioned have for example a molecular weight of about 1,000 to 1,000,000, preferably 2,000 to 200,000 and an acid value of about 10 to 200 mg KOH/g, preferably 20 to 180 mg KOH/g.

A preferred photopolymerizable composition comprises as component (a) a compound having at least two ethylenically unsaturated bonds and at least one carboxylic acid group in the molecule, in particular a reaction product obtained by adding an epoxy group containing unsaturated compound to a part of the carboxyl groups of a carboxylic acid group containing polymer or a reaction product of the compound shown below with one or more polybasic acid anhydrides. Further preferred components (a) comprise a compound obtained from the reaction of a compound of the formula XIV with one or more polybasic acid anhydrides.

Further examples are reaction products obtained by adding an epoxy group containing unsaturated compound to a part of the carboxyl groups of a carboxylic acid group containing polymer. As the carboxylic acid containing polymer, the acrylate, copolymers of tetrahydrofurfuryl(meth)acrylate, styrene and (meth)acrylic acid, and the like.

Examples of the unsaturated compounds having an epoxy group are given below in the formula (V-1)-(V-15);

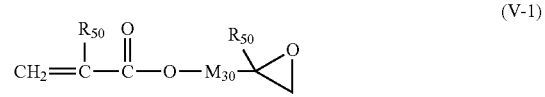
(V-1)

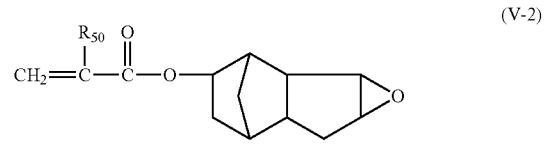
(V-2)

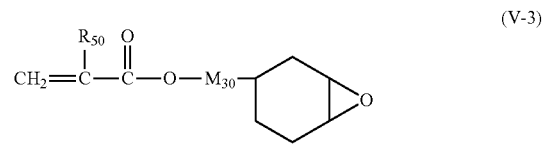
(V-3)

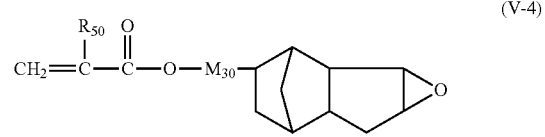
(V-4)

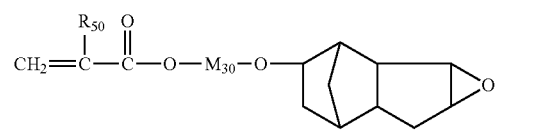
(V-5)

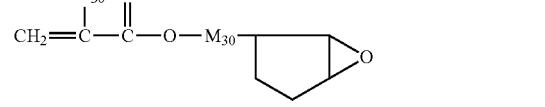
(V-6)

-continued

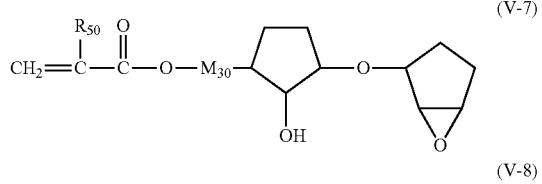 (V-7)

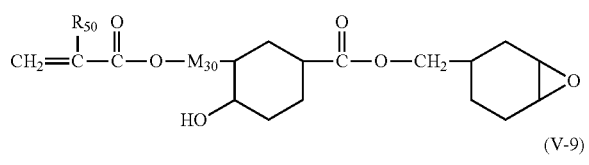 (V-8)

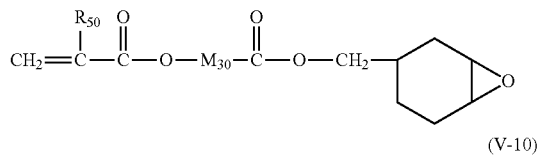 (V-9)

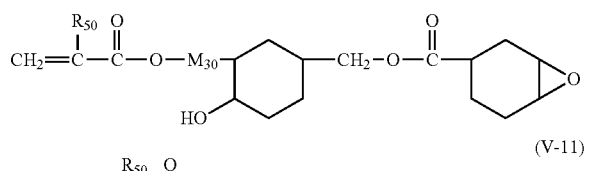 (V-10)

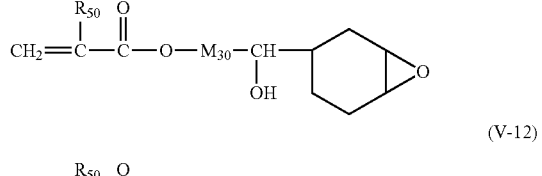 (V-11)

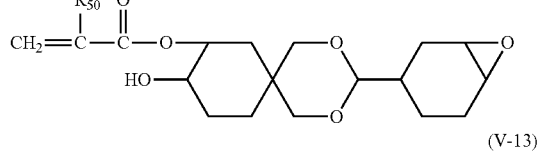 (V-12)

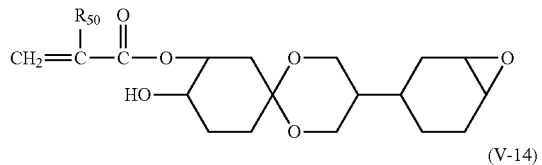 (V-13)

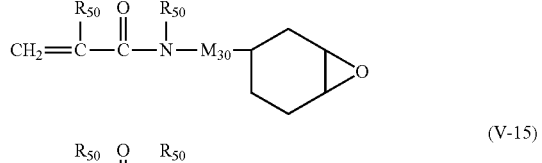 (V-14)

$$\underset{CH_2=\overset{R_{50}}{\underset{|}{C}}-\overset{O}{\overset{||}{C}}-\overset{R_{50}}{\underset{|}{N}}-M_{30}-O-M_{30}}{} \text{(V-15)}$$

wherein $R_{50}$ is hydrogen or methyl group, $M_{30}$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methyl styrene and acrylic acid or a copolymer of methyl methacrylate and acrylic acid with 3,4-epoxycyclohexylmethyl(meth)acrylate.

Unsaturated compounds having a hydroxy group such as 2-hydroxyethyl(meth)acrylate and glycerol mono(meth)acrylate can be used instead of the above mentioned epoxy group containing unsaturated compounds as the reactant for carboxylic acid group containing polymers.

Other examples are half esters of anhydride containing polymers, for example reaction products of a copolymer of maleic anhydride and one or more other polymerizable compounds with (meth)acrylates having an alcoholic hydroxy group such as 2-hydroxyethyl(meth)acrylate or having an epoxy group for example such as the compounds described in the formula (V-1)-(V-15).

Reaction products of polymers having alcoholic hydroxy groups such as copolymers of 2-hydroxyethyl(meth)acrylate, (meth)acrylic acid, benzy methacylate and styrene, with (meth)acrylic acid or (meth)acryl chloride can also be used as component (a).

Other examples are reaction products of a polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy group containing (meth)acrylic compound to all of the carboxyl groups of a carboxylic acid containing polymer as mentioned above.

The photopolymerizable compounds can be used alone or in any desired mixtures.

In a color filter resist composition the whole amount of the monomers contained in the photopolymerizable composition is preferably 5 to 80% by weight, in particular 10 to 70% by weight based on the whole solid contents of the composition, i.e. the amount of all components without the solvent(s).

As the binder used in the color filter resist composition, which is soluble in an alkaline aqueous solution and insoluble in water, for example, a homopolymer of a polymerizable compound having one or more acid groups and one or more polymerizable unsaturated bonds in the molecule, or a copolymer of two or more kinds thereof, and a copolymer of one or more polymerizable compounds having one or more unsaturated bonds copolymerizable with these compounds and containing no acid group, can be used. Such compounds can be obtained by copolymerizing one or more kinds of a low molecular compound having one or more acid groups and one or more polymerizable unsaturated bonds in the molecule with one or more polymerizable compounds having one or more unsaturated bonds copolymerizable with these compounds and containing no acid group. Examples of acids groups are, a —COOH group, a —SO₃H group, a —SO₂NHCO— group, a phenolic hydroxy group, a —SO₂NH— group, and a —CO—NH—CO— group. Among those, a high molecular compound having a —COOH group is particularly preferred.

Preferably, the organic polymer binder in the color filter resist composition comprises an alkali soluble copolymer comprising, as addition polymerizable monomer units, at least an unsaturated organic acid compound such as acrylic acid, methacrylic acid and the like. It is preferred to use as a further co-monomer for the polymer binder an unsaturated organic acid ester compound such as methyl acrylate, ethyl (meth)acrylate, benzyl(meth)acrylate, styrene and the like to balance properties such as alkaline solubility, adhesion rigidity, chemical resistance etc.

The organic polymer binder can either be a random co-polymer or a block-co-polymer, for example, such as described in U.S. Pat. No. 5,368,976.

Examples of the polymerizable compounds having one or more —COOH groups and one or more polymerizable unsaturated bonds in a molecule are (meth)acrylic acid, 2-carboxy-ethyl(meth)acrylic acid, 2-carboxypropyl(meth)acrylic acid, crotonic acid, cinnamic acid, mono[2-(meth)acryloyloxy-ethyl]succinate, mono[2-(meth)acryloyloxyethyl]adipate, mono[2-(meth)acryloyloxyethyl]phthalate, mono[2-(meth)acryloyloxyethyl]hexahydrophthalate, mono[2-(meth)acryloyloxyethyl]maleate, mono[2-(meth)acryloyloxypropyl]succinate, mono[2-(meth)acryloyloxypropyl]adipate, mono[2-(meth)acryloyloxypropyl]phthalate, mono[2-(meth)acryloyloxypropyl]hexahydrophthalate, mono[2-(meth)acryloyloxypropyl]maleate, mono[2-(meth)acryloyloxybutyl]succinate, mono[2-(meth)acryloyloxybutyl]adipate, mono[2-(meth)acryloyloxybutyl]phthalate, mono[2-(meth)acryloyloxybutyl]hexahydrophthalate, mono[2-(meth)acryloyloxybutyl]maleate, 3-(alkylcarbamoyl)acrylic acid, α-chloroacrylic acid, maleic acid, monoesterified maleic acid, fumaric acid, itaconic acid, citraconic acid, mesaconic acid, maleic anhydride, and ω-carboxypolycaprolactone mono(meth)acrylate.

Vinylbenzenesulfonic acid and 2-(meth)acrylamide-2-methylpropanesulfonic acid are examples of the polymerizable compounds having one or more —$SO_3H$ groups and one or more polymerizable unsaturated bonds.

N-methylsulfonyl(meth)acrylamide, N-ethylsulfonyl(meth)acrylamide, N-phenylsulfonyl(meth)acrylamide, and N-(p-methylphenylsulfonyl)(meth)acrylamide are examples of the polymerizable compounds having one or more —$SO_2NHCO$— groups and one or more polymerizable unsaturated bonds.

Examples of polymerizable compounds having one or more phenolic hydroxy groups and one or more polymerizable unsaturated bonds in a molecule include hydroxyphenyl(meth)acrylamide, dihydroxyphenyl(meth)acrylamide, hydroxyphenyl-carbonyloxyethyl(meth)acrylate, hydroxyphenyloxyethyl(meth)acrylate, hydroxyphenylthioethyl(meth)acrylate, dihydroxyphenylcarbonyloxyethyl(meth)acrylate, dihydroxyphenyloxyethyl(meth)acrylate, and dihydroxy-phenylthioethyl(meth)acrylate.

Examples of the polymerizable compounds having one or more —$SO_2NH$— groups and one or more polymerizable unsaturated bonds in the molecule include compounds represented by formula (a) or (b):

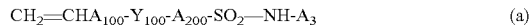

$CH_2$=$CHA_{100}$-$Y_{100}$-$A_{200}$-$SO_2$—NH-$A_3$ (a)

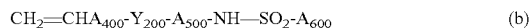

$CH_2$=$CHA_{400}$-$Y_{200}$-$A_{500}$-NH—$SO_2$-$A_{600}$ (b)

wherein $Y_{100}$ and $Y_{200}$ each represents —COO—, —$CONA_{700}$-, or a single bond; $A_{100}$ and $A_{400}$ each represents H or $CH_3$; $A_{200}$ and $A_{500}$ each represents $C_1$-$C_{12}$alkylene optionally having a substituent, cycloalkylene, arylene, or aralkylene, or $C_2$-$C_{12}$alkylene into which an ether group and a thioether group are inserted, cycloalkylene, arylene, or aralkylene; $A_{300}$ and $A_{600}$ each represents H, $C_1$-$C_{12}$alkyl optionally having a substituent, a cycloalkyl group, an aryl group, or an aralkyl group; and $A_{700}$ represents H, $C_1$-$C_{12}$alkyl optionally having a substituent, a cycloalkyl group, an aryl group, or an aralkyl group.

The polymerizable compounds having one or more —CO—NH—CO— group and one or more polymerizable unsaturated bond include maleimide and N-acryloyl-acrylamide. These polymerizable compounds become the high molecular compounds comprising a —CO—NH—CO— group, in which a ring is formed together with a primary chain by polymerization. Further, a methacrylic acid derivative and an acrylic acid derivative each having a —CO—NH—CO— group can be used as well. Such methacrylic acid derivatives and the acrylic acid derivatives include, for example, a methacrylamide derivative such as N-acetylmethacrylamide, N-propionylmethacrylamide, N-butanoylmethacrylamide, Npentanoylmethacrylamide, N-decanoylmethacrylamide, N-dodecanoylmethacrylamide, N-benzoylmethacrylamide, N-(p-methylbenzoyl)methacryl-amide, N-(p-chlorobenzoyl)methacrylamide, N-(naphthyl-carbonyl)methacrylamide, N-(phenylacetyl)-methacrylamide, and 4-methacryloylaminophthalimide, and an acrylamide derivative having the same substituent as these. These polymerizable compounds polymerize to be compounds having a —CO—NH—CO— group in a side chain.

Examples of polymerizable compounds having one or more polymerizable unsaturated bond and containing no acid group include a compound having a polymerizable unsaturated bond, selected from esters of (meth)acrylic acid, such as methyl(meth)acrylate, ethyl(meth)acrylate, propyl(meth)acrylate, butyl(meth)acrylate, tetrahydrofurfuryl(meth)acrylate, benzyl(meth)acrylate, 2-ethylhexyl(meth)acrylate, hydroxyethyl(meth)acrylate, hydroxypropyl(meth)acrylate, hydroxybutyl(meth)acrylate, glycerol mono(meth)acrylate, dihydroxypropyl(meth)acrylate, allyl(meth)acrylate, cyclohexyl(meth)acrylate, phenyl(meth)acrylate, methoxyphenyl(meth)acrylate, methoxyethyl(meth)acrylate, phenoxyethyl(meth)acrylate, methoxydiethyleneglycol(meth)acrylate, methoxytriethyleneglycol(meth)acrylate, methoxypropyl(meth)acrylate, methoxydipropyleneglycol(meth)acrylate, isobornyl meth(acrylate), dicyclopentadienyl(meth)acrylate, 2-hydroxy-3-phenoxypropyl(meth)acrylate, tricyclo[5.2.1.0$^{2,6}$]decan-8-yl(meth)acrylate, aminoethyl(meth)acrylate, N,N-dimethylaminoethyl(meth)acrylate, aminopropyl(meth)acrylate, N,N-dimethylaminopropyl(meth)acrylate, glycidyl(meth)acrylate, 2-methylglycidyl(meth)acrylate, 3,4-epoxybutyl(meth)acrylate, 6,7-epoxyheptyl(meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methystyrene, dimethoxystyrene, vinylbenzyl methyl ether, vinylbenzyl glycidyl ether, indene, 1-methylindene; vinyl or allyl esters, such as vinyl acetate, vinyl propionate, vinyl butylate, vinyl pivalate, vinyl benzoate, vinyl trimethylacetate, vinyl diethylacetate, vinyl barate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethybutyl ether, vinyl hydroxyethoxyethyl ether, vinyl dimethylaminoethyl ether, vinyl diethylaminoethyl ether, vinyl butylaminoethyl ether, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; amide type unsaturated compounds, such as (meth)acrylamide, N,N-dimethyl(meth)acrylamide, N,N-diethyl(meth)acrylamide, N,N-dibutyl(meth)acrylamide, N,N-diethylhexyl(meth)acrylamide, N,N-dicyclohexyl(meth)acrylamide, N,N-diphenyl(meth)acrylamide, N-methyl-N-phenyl(meth)acrylamide, N-hydroxyethyl-N-methyl(meth)acrylamide, N-methyl(meth)acrylamide, N-ethyl(meth)acrylamide, N-propyl(meth)acrylamide, N-butyl(meth)acrylamide, N-hydroxyethyl(meth)acrylamide, N-heptyl(meth)acrylamide, N-octyl(meth)acrylamide, N-ethyhexyl(meth)acrylamide, N-hydroxyethyl(meth)acrylamidecyclohexyl, N-benzyl(meth)acrylamide, N-phenyl(meth)acrylamide, N-tolyl (meth)acrylamide, N-hydroxyphenyl(meth)acrylamide, N-naphthyl(meth)acrylamide, N-phenylsulfonyl(meth)acrylamide, N-methylphenylsulfonyl(meth)acrylamide and N-(meth)acryloylmorpholine, diacetone acrylamide, N-methylol acrylamide, N-butoxyacrylamide; polyolefin type compounds, such as butadiene, isoprene, chloroprene and the like; (meth)acrylonitrile, methyl isopropenyl ketone, maleimide, N-phenylmaleimide, N-methylphenylmaleimide, N-methoxyphenylmaleimide, N-cyclohexylmaleimide, N-alkylmaleimide, maleic anhydride, polystyrene macromonomer, polymethyl(meth)acrylate macromonomer, polybutyl(meth)acrylate macromonomer; crotonates, such as butyl crotonate, hexyl crotonate, glycerine monocrotonate; and itaconates, such as dimethyl itaconate, diethyl itaconate, dibutyl itaconate; and maleates or fumarates, such as dimethyl mareate, dibutyl fumarate.

Preferable examples of copolymers are copolymers of methyl(meth)acrylate and (meth)acrylic acid, copolymers of benzyl(meth)acrylate and (meth)acrylic acid, copolymers of methyl(meth)acrylate/, ethyl(meth)acrylate and (meth)acrylic acid, copolymers of benzyl(meth)acrylate, (meth)acrylic acid and styrene, copolymers of benzyl(meth)acrylate, (meth)acrylic acid and 2-hydroxyethyl(meth)acrylate, copolymers of methyl(meth)acrylate/, butyl(meth)acrylate, (meth)acrylic acid and styrene, copolymers of methyl(meth)acrylate, benzyl(meth)acrylate, (meth)acrylic acid and hydroxyphenyl(meth)acrylate, copolymers of methyl(meth)acrylate, (meth)acrylic acid and polymethyl(meth)acrylate macromonomer, copolymers of benzyl(meth)acrylate, (meth)acrylic acid and polymethyl(meth)acrylate macromonomer, copolymers of tetrahydrofurfuryl(meth)acrylate, styrene and (meth)acrylic acid, copolymers of methyl (meth)acrylate, (meth)acrylic acid and polystyrene macromonomer, copolymers of benzyl(meth)acrylate, (meth)acrylic acid and polystyrene macromonomer, copolymers of benzyl(meth)acrylate, (meth)acrylic acid, 2-hydroxyethyl(meth)acrylate and polystyrene macromonomer, copolymers of benzyl(meth)acrylate, (meth)acrylic acid, 2-hydroxypropyl(meth)acrylate and polystyrene macromonomer, copolymers of benzyl(meth)acrylate, (meth)acrylic acid, 2-hydroxy-3-phenoxypropyl(meth)acrylate and polymethyl(meth)acrylate macromonomer, copolymers of methyl(meth)acrylate, (meth)acrylic acid, 2-hydroxyethyl (meth)acrylate and polystyrene macromonomer, copolymers of benzyl(meth)acrylate, (meth)acrylic acid, 2-hydroxyethyl (meth)acrylate and polymethyl(meth)acrylate macromonomer, copolymers of N-phenylmaleimide, benzyl(meth)acrylate, (meth)acrylic acid and styrene, copolymers of benzyl (meth)acrylate, (meth)acrylic acid, N-phenylmaleimide, mono-[2-(meth)acryloyloxyethyl]succinate and styrene, copolymers of allyl(meth)acrylate, (meth)acrylic acid, N-phenylmaleimide, mono-[2-(meth)acryloyloxyethyl]succinate and styrene, copolymers of benzyl(meth)acrylate, (meth)acrylic acid, N-phenylmaleimide, glycerol mono (meth)acrylate and styrene, copolymers of benzyl(meth)acrylate, ω-carboxypolycaprolactone mono(meth)acrylate, (meth)acrylic acid, N-phenylmaleimide, glycerol mono (meth)acrylate and styrene, and copolymers of benzyl(meth)acrylate, (meth)acrylic acid, N-cyclohexylmaleimide and styrene.

There can be used as well hydroxystyrene homo- or co-polymers or a novolak type phenol resin, for example, poly (hydroxystyrene) and poly(hydroxystyrene-co-vinylcyclohexanol), a novolak resin, a cresol novolak resin, and a halogenated phenol novolak resin. More specifically, it includes, for example, the methacrylic acid copolymers, the acrylic acid copolymers, the itaconic acid copolymers, the crotonic acid co-polymers, the maleic anhydride co-polymers, for example, with styrene as a co-monomer, and maleic acid copolymers, and partially esterified maleic acid copolymers each described in, for example, JP 59-44615-B4 (the term "JP-B4" as used herein refers to an examined Japanese patent publication), JP 54-34327-B4, JP 58-12577-B4, and JP 54-25957-B4, JP 59-53836-A, JP 59-71048-A, JP 60-159743-A, JP 60-258539-A, JP 1-152449-A, JP 2-199403-A, and JP 2-199404-A, and which copolymers can be further reacted with an amine, as e.g disclosed in U.S. Pat. No. 5,650,263; further, a cellulose derivative having a carboxyl group on a side chain can be used, and particularly preferred are copolymers of benzyl(meth)acrylate and (meth) acrylic acid and copolymers of benzyl(meth)acrylate, (meth) acrylic acid and other monomers, for example as described in U.S. Pat. No. 4,139,391, JP 59-44615-B4, JP 60-159743-A and JP 60-258539-A.

With respect to those having carboxylic acid groups among the above organic binder polymers, it is possible to react some or all of the carboxylic acid groups with glycidyl(meth)acrylate or an epoxy(meth)acrylate to obtain photopolymerizable organic binder polymers for the purpose of improving the photosensitivity, coating film strength, the coating solvent and chemical resistance and the adhesion to the substrate. Examples are disclosed in, JP 50-34443-B4 and JP 50-34444-B4, U.S. Pat. No. 5,153,095, by T. Kudo et al. in J. Appl. Phys., Vol. 37 (1998), p. 3594-3603, U.S. Pat. No. 5,677,385, and U.S. Pat. No. 5,650,233.

The weight-average molecular weight of the binders is preferably 500 to 1,000,000, e.g. 3,000 to 1,000,000, more preferably 5,000 to 400,000.

These compounds may be used singly or as a mixture of two or more kinds. The content of the binder in the light-sensitive resin composition is preferably 10 to 95 weight %, more preferably 15 to 90 weight % based on the whole solid matters.

Further, in the color filter the total solid component of each color may contain an ionic impurity-scavenger, e.g. an organic compound having an epoxy group. The concentration of the ionic impurity scavenger in the total solid component generally is in the range from 0.1% by weight to 10% by weight.

Examples of color filters, especially with respect to the above described combinations of pigments and ionic impurity scavenger are given in EP 320264. It is understood, that the photoinitiators according to the present invention, i.e. the compounds of the formula I in the color filter formulations described in EP 320264 can replace the triazine initiator compounds.

The compositions according to this invention can comprise additionally a crosslinking agent which is activated by an acid, for example as described in JP 10-221843A, and a compound which generates acid thermally or by actinic radiation and which activates a crosslinking reaction.

The compositions according to this invention can also comprise latent pigments which are transformed into finely dispersed pigments during the heat treatment of the latent pigment containing photosensitive pattern or coating. The heat treatment can be performed after exposure or after development of the latent pigment-containing photoimageable layer. Such latent pigments are soluble pigment precursors which can be transformed into insoluble pigments by means of chemical, thermal, photolytic or radiation induced methods as described, for example, in U.S. Pat. No. 5,879,855. This transformation of such latent pigments can be enhanced by adding a compound which generates acid at actinic exposure or by adding an acidic compound to the composition. Therefore, a color filter resist can also be prepared, which comprises a latent pigment in a composition according to this invention.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. No. 5,368,976; U.S. Pat. No. 5,800,952; U.S. Pat. No. 5,882,843; U.S. Pat. No. 5,879,855; U.S. Pat. No. 5,866,298; U.S. Pat. No. 5,863,678; JP 06-230212A; EP320264; JP 09-269410A; JP 10-221843A; JP 01-090516A; JP 10-171119A, U.S. Pat. No. 5,821,016, U.S. Pat. No. 5,847,015, U.S. Pat. No. 5,882,843, U.S. Pat. No. 5,719,008, EP881541, or EP902327.

The photoinitiators of the present invention can be used in color filter resists, for example, such as those given as examples above, or can partially or fully replace the known photoinitiators in such resists. It is understood by a person skilled in the art that the use of the new photoinitiators of the present invention is not limited to the specific binder resins, crosslinkers and formulations of the color filter resist examples given hereinbefore but can be used in conjunction with any radically polymerizable component in combination with a dye or color pigment or latent pigment to form a photosensitive color filter ink or color filter resist.

Accordingly, subject of the invention also is a color filter prepared by providing red, green and blue (RGB) colour elements and, optionally a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder and a photopolymerization initiator of formula I or I' as described above or a photoinitiator mixture of a compound of the formula I or I'. The monomer and binder components, as well as suitable pigments are as described above. In the manufacture of color filters the transparent electrode layer can either be applied on the surface of the transparent substrate or can be provided on the surface of the red, green and blue picture elements and the black matrix. The transparent substrate is for example a glass substrate which can additionally have an electrode layer on its surface.

It is preferred to apply a black matrix between the color areas of different color in order to improve the contrast of a color filter.

The photosensitive compositions of the present invention, as already stated above, are also suitable for the preparation of the black matrix of color filters. Said black matrix composition for example comprises a photoinitiator compound of the formula I of the present invention, an organic binder, in particular an organic binder, which is an epoxy acrylate resin having a carboxyl group, a black coloring material, a polymer dispersant, in particular a polymer dispersant containing a basic functional group.

The person skilled in the art is familiar with such formulations. Examples of suitable black matrix compositions and the components (other than the photoinitiator) as described above are given in JP Patent No. 3754065, the disclosure of which hereby is incorporated by reference.

Instead of forming a black matrix using a photosensitive composition and patterning the black photosensitive composition photolithographically by patternwise exposure (i.e. through a suitable mask) to form the black pattern separating the red green and blue coloured areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

There are different methods known how and at which step in the color filter manufacturing process the black matrix can be applied. It can either be applied directly on the transparent substrate prior to formation of the red, green and blue (RGB) colour filter as already mentioned above, or it can be applied after the RGB colour filter is formed on the substrate.

In a different embodiment of a color filter for a liquid crystal display, according to U.S. Pat. No. 626,796, the black matrix can also be applied on the substrate opposite to the RGB color filter element-carrying substrate, which is separated from the former by a liquid crystal layer.

If the transparent electrode layer is deposited after applying the RGB color filter elements and—optionally—the black matrix, an additional overcoat film as a protective layer can be applied on the color filter layer prior to deposition of the electrode layer, for example, as described in U.S. Pat. No. 5,650,263.

To form an overcoat layer of a color filter, photosensitive resin or thermosetting resin compositions are employed. The photosensitive composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009A, JP1-130103A and JP1-134306A. In this regard, it is difficult to selectively form a protective layer with good precision using the above-mentioned thermosetting resins. The photosensitive composition, however, allows to easily remove the unnecessary parts of the protective layer by photolithography.

It is obvious to those skilled in the art, that the photosensitive compositions of the present invention can be used for generating red, green and blue color pixels and a black matrix, for the manufacture of a color filter, regardless, of the above described differences in processing, regardless, of additional layers which can be applied and regardless of differences in the design of the color filter. The use of a composition according to the present invention to form colored elements shall not be regarded as limited by different designs and manufacturing processes of such color filters.

The photo-sensitive composition of the present invention can suitably be used for forming a color filter but will not be limited to this application. It is useful as well for a recording material, a resist material, a protective layer, a dielectric layer, in display applications and display elements, a paint, and a printing ink.

The photosensitive compositions according to the invention are also suitable for manufacturing interlayer insulating layers or dielectric layers in a liquid crystal display, and more particularly in a reflection type liquid crystal display including an active matrix type display having a thin film transistor (TFT) as a switching device, and a passive matrix type without a switching device.

In recent years, liquid crystal displays have, for example, been widely used for pocket-type TV sets and terminal devices for communication by virtue of its small thickness and light weight. A reflection type liquid crystal display without necessity of using a back light is in particular in demand because it is ultra-thin and light-weight, and it can significantly reduce power consumption. However, even if a back light is removed out of a presently available transmission type color liquid crystal display and a light reflection plate is added to a lower surface of the display, it would cause a problem in that the efficiency of utilizing lights is low, and it is not possible to have practical brightness. As a solution to this problem, there have been suggested various reflection type liquid crystal displays for enhancing an efficiency of utilizing lights. For instance, a certain reflection type liquid crystal display is designed to include a pixel electrode having reflection function.

The reflection type liquid crystal display includes an insulating substrate and an opposing substrate spaced away from the insulating substrate. A space between the substrates is filled with liquid crystals. A gate electrode is formed on the insulating substrate, and both the gate electrode and the insulating substrate are covered with a gate insulating film. A semiconductor layer is then formed on the gate insulating film above the gate electrode. A source electrode and a drain electrode are also formed on the gate insulating film in contact with the semiconductor layer. The source electrode, the drain electrode, the semiconductor layer, and the gate electrode cooperate with one another to thereby constitute a bottom gate type TFT as a switching device.

An interlayer insulating film is formed covering the source electrode, the drain electrode, the semiconductor layer, and the gate insulating film therewith. A contact hole is formed throughout the interlayer insulating film on the drain electrode. A pixel electrode made of aluminum is formed on both the interlayer insulating film and an inner sidewall of the contact hole. The drain electrode of the TFT is eventually in contact with the pixel electrode through the interlayer insulating film. The interlayer insulating layer is generally designed to have a roughened surface by which the pixel electrode acts as a reflection plate which diffuses lights to get a wider angle for viewing (angle of visibility).

The reflection type liquid crystal display remarkably enhances an efficiency of using lights by virtue that the pixel electrode acts as a light reflection plate.

In the above-mentioned reflection type liquid crystal display, the interlayer insulating film is designed to have projections and recesses by photolithography. To form and control a fine shape of the projections and recesses in micrometer order for surface roughness and to form contact holes, photolithography methods using positive and negative photoresists are used. For these resists the compositions according to the invention are especially suitable.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. In a liquid crystal cell, the spacing between the substrates in the cell is maintained constant by sparsely distributing glass or polymer spheres about several micrometers in diameter as spacers between the substrates. The spacers are thus held between the substrates to maintain the distance between the substrates at a constant value. The distance is determined by the diameter of the spacers. The spacers assure the minimum spacing between the substrates; i.e., they prevent a decrease in distance between the substrates. However, they cannot prevent the substrates from being separated apart from each other, i.e. the increase in distance between the substrates. Additionally, this method of using spacer beads has problems of the uniformity in the diameter of spacer beads and difficulty in the even dispersion of spacer beads on the panel, as well as nonuniform orientation and decrease in brightness and/or optical aperture depending on the location of spacers on pixel array region. Liquid crystal displays having a large image display area have recently been attracting much attention. However, the increase in the area of a liquid crystal cell generally produces the distortion of the substrates constituting the cell. The layer structure of the liquid crystal tends to be destroyed due to the deformation of the substrate. Thus, even when spacers are used for maintaining the spacing between the substrates constant, a liquid crystal display having a large image display area is unfeasible because the display experiences disturbances. Instead of the above spacer sphere dispersion method, a method of forming columns in the cell gap as spacers has been proposed. In this method, columns of a resin are formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In recent years, as the spread of the touch panel type liquid crystal displays such as mobile audio players and handheld game platforms, the mechanical stress to liquid crystal panel tends to grow. The demand for spacer that controls the cell gap to raise mechanical strength becomes strong thus the multi-spacer method is used. According to the multi-spacer method, when cell gap narrows by pressure from the outside, adding to main-spacer that controls the cell gap normally lower sub-spacer supports the cell gap against external stress. The multi-spacer can follow the contraction of liquid crystal at low temperature conditions by main-spacer and prevent to generate bubbles inside the liquid crystal.

The multi-spacer which contains main-spacer and sub-spacer is formed in the same step using, for example, a halftone mask as described in JPA-2011065133. The photosensitive compositions according to the invention are eligible for manufacturing process using halftone mask.

In a color liquid crystal display panel, such spacers are formed in the nonimaging area under black matrix of color filter elements. Therefore, the spacers formed using photosensitive compositions do not decrease brightness and optical aperture.

Photosensitive compositions for producing protective layer with spacers for color filters are disclosed in JP 2000-81701A and dry film type photoresists for spacer materials are also disclosed in JP 11-174459A and JP 11-174464A. As described in the documents, the photosensitive compositions, liquid and dry film photoresists, are comprising at least an alkaline or acid soluble binder polymer, a radically polymerizable monomer, and a radical initiator. In some cases, thermally crosslinkable components such as epoxide and carboxylic acid may additionally be included.

The steps to form spacers using a photosensitive composition are as follows:

a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a postbaking is carried out to thermally cure the composition.

The photocurable compositions according to the invention are suitable for producing spacers for liquid crystal displays (as described above) because of their high sensitivity.

The photosensitive compositions according to the invention are also suitable for manufacturing microlens arrays used in liquid crystal display panels, image sensors and the like.

Microlenses are microscopic passive optical components that fit on active optoelectronic devices such as detectors, displays, and light emitting devices (light-emitting diodes, transversal and vertical cavity lasers) to improve their optical input or output quality. The areas of applications are wide and cover areas such as telecommunications, information technology, audio-visual services, solar cells, detectors, solid-state light sources, and optical interconnects.

Present optical systems use a variety of techniques to obtain efficient coupling between microlenses and microoptical devices.

The microlens arrays are used for condensing illuminating light on the picture element regions of a nonluminescent display device, such as a liquid crystal display devices, to increase the brightness of the display, for condensing incident light or as a means for forming an image on the photoelectric conversion regions of a line image sensor used for example in facsimiles and the like to improve the sensitivity of these devices, and for forming an image to be printed on a photosensitive means used in liquid crystal printers or light emitting diode (LED) printers.

The most common application is their use to improve the efficiency of photodetector arrays of a solid-state image sensing device such as a charge coupled device (CCD). In a detector array, the collection of as much light as possible in each detector element or pixel is wanted. If a microlens is put on top of each pixel, the lens collects incoming light and focuses it onto an active area that is smaller than the size of the lens.

According to the prior-art, microlens arrays can be produced by a variety of methods; for each of them compositions according to the present invention may be employed.

(1) A method for obtaining convex lenses wherein a pattern of the lenses in a planar configuration is drawn on a thermoplastic resin by a conventional photolithographic technique or the like, and then the thermoplastic resin is heated to a temperature above the softening point of the resin to have flowability, thereby causing a sag in the pattern edge (so called "reflowing") (see, e.g., JP 60-38989A, JP 60-165623A, JP 61-67003A, and JP 2000-39503A). In this method, when the thermoplastic resin used is photosensitive, a pattern of the lenses can be obtained by exposure of this resin to light.

(2) A method for forming a plastic or glass material by the use of a mold or a stamper. As lens material, a photocurable resin and a thermosetting resin can be used in this method (see, e.g., WO99/38035).

(3) A method for forming convex lenses on the basis of a phenomenon in which when a photosensitive resin is exposed to light in a desired pattern by the use of an aligner, unreacted monomers move from the unexposed regions to the exposed regions, resulting in a swell of the exposed regions (see, e.g., Journal of the Research Group in Microoptics Japanese Society of Applied Physics, Colloquium in Optics, Vol. 5, No. 2, pp. 118-123 (1987) and Vol. 6, No. 2, pp. 87-92 (1988)).

On the upper surface of a supporting substrate, a photosensitive resin layer is formed. Thereafter, with the use of a separate shading mask, the upper surface of the photosensitive resin layer is illuminated with light from a mercury lamp or the like, so that the photosensitive resin layer is exposed to the light. As a result, the exposed portions of the photosensitive resin layer swell into the shape of convex lenses to form the light condensing layer having a plurality of microlens.

(4) A method for obtaining convex lenses wherein a photosensitive resin is exposed to light by a proximity exposure technique in which a photomask is not brought into contact with the resin, to cause a blur at the pattern edge, so that the amount of photochemical reaction products is distributed depending upon the degree of blurring at the pattern edge (see, e.g., JP 61-153602A).

(5) A method for generating a lens effect wherein a photosensitive resin is exposed to light with a particular intensity distribution to form a distribution pattern of refractive index depending upon the light intensity (see, e.g., JP 60-72927A and JP 60-166946A).

The photosensitive compositions according to the invention can be used in any one of the above-mentioned methods to form microlens arrays using photocurable resin compositions.

A particular class of techniques concentrates on forming microlenses in thermoplastic resins like photoresist. An example is published by Popovic et al. in the reference SPIE 898, pp. 23-25 (1988). The technique, named reflow technique, comprises the steps of defining the lenses' footprint in a thermoplastic resin, e.g. by photolithography in a photosensitive resin like a photoresist, and subsequently heating this material above its reflow temperature. The surface tension draws the island of photoresist into a spherical cap with a volume equal to the original island before the reflow. This cap is a plano-convex microlens. Advantages of the technique are, amongst others, the simplicity, the reproducibility, and the possibility of integration directly on top of a light-emitting or light-detecting optoelectronic device.

In some cases, an overcoat layer is formed on the patterned lens units with a rectangular shape prior to reflowing to avoid a sagging of the island of the resin in the middle without reflow into a spherical cap in the reflow step. The overcoat acts as a permanent protective layer. The coating layer is also made of a photosensitive composition. Microlens arrays can also be fabricated by the use of a mold or a stamper as, for example, disclosed in EP0932256. A process of manufacturing the planar microlens array is as follows: a release agent is coated on a shaping surface of a stamper on which convex portions are densely arranged, and a photocurable synthetic resin material having a high refractive index is set on the shaping surface of the stamper. Next, the base glass plate is pushed onto the synthetic resin material, thereby spreading the synthetic resin material, and the synthetic resin material is cured by irradiating with ultraviolet radiation or by heating and is shaped to form the convex microlenses. Thereafter the stamper is peeled off. Then, a photocurable synthetic resin material having a low refractive index is additionally coated onto the convex microlenses as an adhesive layer and a glass substrate which is made into a cover glass plate is pushed onto the synthetic resin material, thereby spreading the same. The synthetic resin material is then cured and finally the planar microlens array is formed.

As disclosed in U.S. Pat. No. 5,969,867, a similar method using a mold is applied for the production of a prism sheet, which is used as a part of backlight units for color liquid crystal display panels to enhance the brightness. A prism sheet forming a prism row on one side is mounted on the light-emitting surface of the backlight. For fabricating a prism sheet, an active energy ray-curable composition is cast and spread in a lens mold which is made of metal, glass or resin and forms the lens shape of the prism row, etc., after which a transparent substrate sheet is placed onto it and active energy rays from an active energy ray-emitting source are irradiated through the sheet for curing. The prepared lens sheet is then released from the lens mold to obtain the lens sheet.

The active energy ray-curable composition used to form the lens section must have a variety of properties, including adhesion to the transparent substrate, and suitable optical characteristics.

Lenses at least with some photoresists in the prior art are not desirable for some applications since the optical transmittance in the blue end of the optical spectrum is poor. Because the photocurable compositions according to the invention have low yellowing properties, both thermally and photochemically, they are suitable for the production of microlens arrays as described above.

The novel radiation-sensitive compositions are also suitable for photo-lithographic steps used in the production process of plasma display panels (PDP), particularly for the imaging forming process of barrier rib, phosphor layer and electrodes.

The PDP is a planar display for displaying images and information by virtue of the emission of light by gas discharge. By the construction of panel and the method of operation, it is known in two types, i.e. DC (direct current) type and AC (alternating current) type.

By way of example, the principle of the DC type color PDP will be briefly explained. In the DC type color PDP, the space intervening between two transparent substrates (generally glass plates) is divided into numerous minute cells by latticed barrier ribs interposed between the transparent substrates. In the individual cells a discharge gas, such as He or Xe, is sealed. On the rear wall of each cell there is a phosphor layer which, on being excited by the ultraviolet light generated by the discharge of the discharge gas, emits visible light of three primary colors. On the inner faces of the two substrates, electrodes are disposed as opposed to each other across the relevant cells. Generally, the cathodes are formed of a film of transparent electroconductive material such as NESA glass. When a high voltage is applied between these electrodes formed on the fore wall and the rear wall, the discharge gas which is sealed in the cells induces plasma discharge and, by virtue of the ultraviolet light radiated consequently, incites the fluorescent elements of red, blue, and green colors to emit lights and effect the display of an image. In the full-color display system, three fluorescent elements severally of the three primary colors of red, blue, and green mentioned above jointly form one picture element.

The cells in the DC type PDP are divided by the component barrier ribs of a lattice, whereas those in the AC type PDP are divided by the barrier ribs which are arranged parallel to each other on the faces of the substrates. In either case, the cells are divided by barrier ribs. These barrier ribs are intended to confine the luminous discharge within a fixed area to preclude false discharge or cross talk between adjacent discharge cells and ensure ideal display.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

The compounds of the formula I are also suitable as photoinitiators in the holographic data storage application. Said photoinitiators generate radicals and initiate polymerization of monomer upon irradiation with blue laser radiation, suitable for holographic data storage. The wavelength range of the blue laser is 390-420 nm, preferably 400-410 nm and particularly 405 nm. Holographic storage systems (holographic recording media) are for example used to record and to retrieve a large amount of data with fast access time. The photoinitiators of the invention are for example in particular suitable for systems as described for example in WO 03/021358.

The holographic data storage system is preferably comprised of a matrix network of low-refractive index matrix precursors and high-refractive index photopolymerizable monomers.

The matrix precursor and photoactive monomer can be selected such that (a) the reaction by which the matrix precursor is polymerized during the cure is independent from the reaction by which the photoactive monomer will be polymerized during writing of a pattern, e.g. data, and (b) the matrix polymer and the polymer resulting from polymerization of the photoactive monomer (the photopolymer) are compatible with each other. The matrix is considered to be formed when the photorecording material, i.e. the matrix material plus the photoactive monomer, photoinitiator and/or additives, exhibits an elastic modulus of at least about $10^5$ Pa, generally about $10^5$ Pa to about $10^9$ Pa.

The media matrix is formed by in-situ polymerization which yields as cross-linked network in the presence of the photopolymerizable monomers which remain "dissolved" and unreacted. The matrix containing un-reacted, photopolymerizable monomers can also be formed by other means, for example by using a solid-resin matrix material in which the photoreactive, liquid monomer is homogeneously distributed. Then, monochromatic exposure generates the holographic pattern, which according to the light intensity distribution, polymerizes the photoreactive monomers in the solid pre-formed matrix. The unreacted monomers (where light intensity was at a minimum) diffuse through the matrix, producing a modulation of the refractive index that is determined by the difference between the refractive indices of the monomer and the matrix and by the relative volume fraction of the monomer. The thickness of the recording layer is in the range of several micrometers up to a thickness of one millimeter. Because of such thick holographic data storage layers it is required that the photoinitiator combines high photoreactivity with low absorbance, in order to render the layer transparent at the laser wavelength to assure that the extent of photopolymerization is as little as possible dependent on the exposure depth into the recording layer.

It was found that the photoinitiators of the present invention combine high reactivity with low absorbance at 405 nm and are suitable for this application. Dyes and sensitizers can also be added to the formulations. Suitable dyes and sensitizers for blue laser radiation are for example coumarines, xanthones, thioxanthones, see list above. In particular relevant are thioxanthones, coumarins and benzophenones as mentioned under items 1., 2. and 3. in the list given above.

It was found that the photoinitiators allow photopolymerization of monomers in thick layers, such as required for holographic data storage, with high sensitivity and yield recording layers which are sensitive to blue laser radiation. The photoinitiators, when applied at a concentration of 2-8 wt % in the photosensitive layer of 20 micron thickness yield an absorbance of the layer which comprises the photoinitiator, of less than 0.4, preferably less than 0.2 at the laser wavelength.

The photoinitiators are in particular suitable for the preparation of optical articles (for example optical waveguides) or holographic recording media e.g. comprising a polymer and an organic photoinitiator as described above, having a maximum absorption at a UV wavelength in the range of 340-450 nm, wherein the refractive index contrast adjusted sensitivity is greater than $3\times10^{-6}$ $\Delta n/(mJ/cm^2)$. For example, the polymer is formed by polymerizing a material comprising component 1 and component 2, wherein component 1 comprises a NCO-terminated pre-polymer and component 2 comprises a polyol. Component 1 is, for example, diphenylmethane diisocyanate, toluene diisocyanate, hexamethylene diisocyanate, a derivative of hexamethylene diisocyanate, a methylenebiscyclohexylisocyanate, a derivative of methylenebiscyclohexylisocyanate. Component 2 is for example a polyol of propylene oxide. Preferably, the photoactive monomer is an acrylate monomer. In such media the shrinkage induced by writing is usually less than 0.25%.

Photocuring further is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel photoinitiators for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists. When used in image-forming materials the novel photoinitiators provide excellent performance in generating so called printout images, whereby a color change is induced due to irradiation. To form such printout images different dyes and/or their leuco form are used and examples for such print out image systems can be fount e.g. in WO96/41240, EP706091, EP511403, U.S. Pat. No. 3,579,339 and U.S. Pat. No. 4,622,286.

The novel photoinitiator is also suitable for a photopatternable composition for forming a dielectric layer of a multilayer layer circuit board produced by a sequential build-up process.

The invention, as described above, provides compositions, as well as a process, for producing pigmented and nonpigmented paints and varnishes, powder coatings, printing inks, printing plates, adhesives, pressure sensitive adhesives, dental compositions, gel coats, photoresists for electronics, etch resists, both liquid and dry films, solder resists, resists to manufacture color filters for a variety of display applications (a color filter resist contains pigments, pigments and dyes (i.e.

hybrid systems) or dyes alone), resists to generate structures in the manufacturing processes of plasma-display panels (e.g. barrier rib, phosphor layer, electrode), electroluminescence displays and LCD (e.g. interlayer insulating layers, spacers, multi-spacers, microlens arrays), for encapsulating electrical and electronic components, for producing magnetic recording materials, micromechanical parts, waveguides, optical switches, plating masks, colour proofing systems, glass fibre cable coatings, screen printing stencils, three-dimensional objects by means of stereolithography, image recording materials for holographic recordings (e.g. for holographic data storage (HDS)), microelectronic circuits, decolorizing materials, formulations containing microcapsules, photoresist materials for a UV and visible laser direct imaging system and for forming dielectric layers in a sequential build-up layer of a printed circuit board; wherein the process comprises irradiating a composition as described above with electromagnetic radiation in the range from 150 to 600 nm, or with electron beam or with X-rays.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are, for example, silicon wafers. The layer thickness of the photosensitive layer for photographic materials and offset printing forms is generally from about 0.5 µm to 10 µm, while for printed circuits it is from 0.1 µm to about 100 µm. Following the coating of the substrates, the solvent is removed, generally by drying, to leave a coat of the photoresist on the substrate.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate, ethyl 3-ethoxypropionate, 2-methoxypropylacetate, methyl-3-methoxypropionate, 2-heptanone, 2-pentanone, and ethyl lactate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, or a glass substrate by transferring the layer via lamination.

The quantity applied (coat thickness) and the nature of the substrate (layer support) are dependent on the desired field of application. The range of coat thicknesses generally comprises values from about 0.1 µm to more than 100 µm, for example 0.1 µm to 1 cm, preferably 0.5 µm to 1000 µm.

Following the coating of the substrates, the solvent is removed, generally by drying, to leave an essentially dry resist film of the photoresist on the substrate.

The photosensitivity of the novel compositions can extend in general from about 150 nm to 600 nm, for example 190-600 nm, (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, low-, medium-, high- and super high-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as $F_2$ excimer lasers at 157 nm exposure, KrF excimer lasers for exposure at 248 nm and ArF excimer lasers for exposure at 193 nm are also suitable. Lasers in the visible region can also be employed.

The term "imagewise" exposure includes both, exposure through a photomask comprising a predetermined pattern, for example a slide, a chromium mask, a stencil mask or a reticle, as well as exposure by means of a laser or light beam, which for example is moved under computer control over the surface of the coated substrate and in this way produces an image. Suitable UV laser exposure systems for the purpose are, for example, provided by Etec and Orbotech (DP-100™ DIRECT IMAGING SYSTEM). Other examples of laser light sources are, for example excimer lasers, such as $F_2$ excimer lasers at 157 nm exposure, KrF excimer lasers for exposure at 248 nm and ArF excimer lasers for exposure at 193 nm. Further suitable are solid state UV lasers (e.g. Gemini from ManiaBarco, DI-2050 from PENTAX) and violet laser diodes with 405 nm output (DI-2080, DI-PDP from PENTAX). Lasers in the visible region can also be employed. And the computer-controlled irradiation can also be achieved by electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37.

Following the imagewise exposure of the material and prior to development, it may be advantageous to carry out thermal treatment for a short time. After the development a thermal post bake can be performed to harden the composition and to remove all traces of solvents. The temperatures employed are generally 50-250° C., preferably 80-220° C.; the duration of the thermal treatment is in general between 0.25 and 60 minutes.

The photocurable composition may additionally be used in a process for producing printing plates or photoresists as is described, for example, in DE4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis or organic solvents. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents. Depending on the substrate also solvents, e.g. organic solvents, can be used as developer, or, as mentioned above mixtures of aqueous alkalis with such solvents. Particularly useful solvents for solvent development include methanol, ethanol, 2-propanol, 1-propanol, butanol, diacetone alcohol, ethylene glycol monomethyl ether, ethylene glycol monoethyl ether, ethylene glycol mono-n-butyl ether, diethyleneglycol dimethyl ether, propyleneglycol monomethyl ether acetate, ethyl-3-ethoxypropionate, methyl-3-methoxypropionate, n-butyl acetate, benzyl alcohol, acetone, methyl ethyl ketone, cyclopentanone, cyclohexanone, 2-heptanone, 2-pentanone, epsilon-caprolactone, gamma-butylolactone, dimethylformamide, dimethylacetamide, hexamethylphosphoramide, ethyl lactate, methyl lactate, epsilon-caprolactam, and N-methyl-pyrrolidinone. Optionally, water can be added to these solvents up to a level at which still a clear solution is obtained and at which sufficient solubility of the unexposed areas of the light sensitive composition is maintained.

The invention therefore also provides a process for the photopolymerization of compounds containing ethylenically unsaturated double bonds, i.e. monomeric, oligomeric or polymeric compounds containing at least one ethylenically unsaturated double bond, which comprises adding to these compounds at least one photoinitiator of the formula I as described above and irradiating the resulting composition with electromagnetic radiation, in particular light of the wavelength 150 to 600 nm, in particular 190-600 nm, with electron beam, or with X-rays.

In other words, adding to these compounds containing ethylenically unsaturated double bonds at least one photoinitiator of the formula I as described above and irradiating the resulting composition with electromagnetic radiation, in particular light of the wavelength 150 to 600 nm, in particular 190-600 nm, with electron beam, or with X-rays.

The invention further provides a coated substrate which is coated on at least one surface with a composition as described above, and describes a process for the photographic production of relief images, in which a coated substrate is subjected to imagewise exposure and then the unexposed portions are removed with a developer. Imagewise exposure may be effected by irradiating through a mask or by means of a laser or electron beam as already described above. Of particular advantage in this context is the laser beam exposure already mentioned above.

The compounds of the invention have a good thermal stability, low volatility, good storage stability and high solubility, and are also suitable for photopolymerisations in the presence of air (oxygen). Further, they cause only low yellowing in the compositions after photopolymerization.

The examples which follow illustrate the invention in more detail, without restriciting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

PREPARATION EXAMPLES

Example 1

Synthesis of [11-(2-ethylhexyl)-5-(2,4,6-trimethyl-benzoyl)-11H-benzo[a]carbazole-8-yl]-{2-[6-(2-{[11-(2-ethylhexyl)-5-(2,4,6-trimethyl-benzoyl)-11H-benzo[a]carbazole-8-yl]-acetoxyimino-methyl}-phenoxy)-2,2,3,3,4,4,5,5-octafluoro-hexyloxy]-phenyl}-methanone oxime O-acetate 1.a Synthesis of 11-(2-ethylhexyl)-11H-benzo[a]carbazole

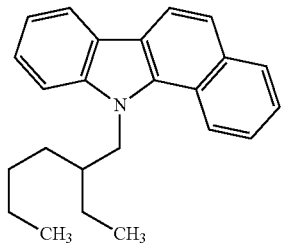 [SMILES: CCCCC(CC)Cn1c2ccccc2c2ccc3ccccc3c21]

11H-Benzo[a]carbazole can be prepared according to some procedures, for instance, the procedure described in SYNLETT, 2006, 7, 1021. The structure is confirmed by the $^1$H-NMR spectrum (CDCl$_3$). δ [ppm]: 7.29 (td, 1H), 7.44 (td, 1H), 7.53 (td), 7.57-7.61 (m, 3H), 7.66 (d, 1H), 8.01 (d, 1H), 8.11-8.15 (m, 3H), 8.77 (br, 1H).

To 11H-benzo[a]carbazole (0.70 g; 3.22 mmol) in dimethyl formamide (DMF) (3 mL) is added sodium hydride (0.19 g; 4.67 mmol) at 0° C. After stirring for 1 h at 0° C., 1-bromo-2-ethylhexane (1.24 g; 6.44 mmol) is added at 0° C., and the mixture is stirred at room temperature overnight. The reaction mixture is poured into ice-water, and the crude product is extracted twice with AcOEt (acetic acid ethyl ester). The combined organic layer is washed with H$_2$O and brine, dried over MgSO$_4$, concentrated and dried in vacuo to give a yellow liquid as a crude product (1.08 g). The product is used for the next reaction without further purification. The structure is confirmed by $^1$H-NMR spectrum (CDCl$_3$). δ [ppm]: 0.80-0.92 (m, 6H), 1.16-1.47 (m, 8H), 2.27 (m, 1H), 4.65-

4.69 (m, 2H), 7.27 (td, 1H), 7.44-7.59 (m, 4H), 7.66 (d, 1H), 8.02 (d, 1H), 8.14 (d, 1H), 8.18 (d, 1H), 8.54 (d, 1H).

1.b Synthesis of [11-(2-ethylhexyl)-8-(2-fluorobenzoyl)-11H-benzo[a]carbazol-5-yl]-(2,4,6-trimethylphenyl)-methanone

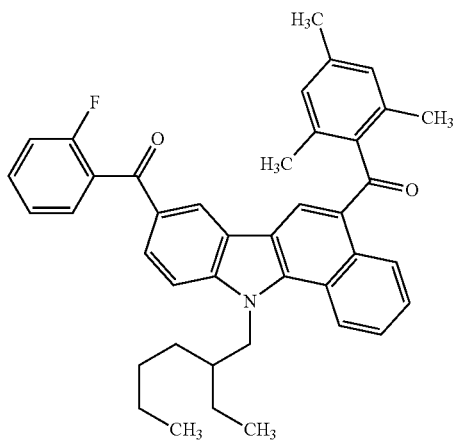 [SMILES: CCCCC(CC)Cn1c2ccc(C(=O)c3ccccc3F)cc2c2cc(C(=O)c3c(C)cc(C)cc3C)c3ccccc3c21]

To 11-(2-ethylhexyl)-11H-benzo[a]carbazole (47.16 g; 143.0 mmol) in $CH_2Cl_2$ (400 mL) are added 2,4,6-trimethylbenzoyl chloride (27.45 g; 150.0 mmol) and $AlCl_3$ (20.00 g; 150.0 mmol) at 0° C. After stirring at room temperature for 2 hours, $AlCl_3$ (22.93 g; 172.0 mmol) is added at 0° C. and 2-fluorobenzoyl chloride (23.78 g; 150.0 mmol) is added dropwise, and then the mixture is stirred at room temperature for 3 hours. The reaction mixture is poured into ice-water, and the crude product is extracted twice with $CH_2Cl_2$. The combined organic layer is washed with water and brine, dried over $MgSO_4$. After 230 ml of n-hexane are added, the $CH_2Cl_2$ is removed by concentration to give a beige solid. It is collected by filtration, and washed with n-hexane. Then it is dried to give a beige solid (81.81 g; 95.7%). The structure is confirmed by $^1$H-NMR spectrum ($CDCl_3$). δ [ppm]: 0.84 (t), 0.89 (t), 1.18-1.42 (m), 2.20 (s), 2.28-2.31 (m), 2.40 (s), 4.72-4.76 (m), 6.96 (s), 7.19 (t), 7.29 (t), 7.52-7.60 (m), 7.70-7.84 (m), 8.38 (s), 8.63-8.66 (m), 9.56 (d); $^{19}$F-NMR spectrum ($CDCl_3$). δ [ppm]: −111.58.

1.c Synthesis of [2-(6-{2-[11-(2-Ethylhexyl)-5-(2,4,6-trimethyl-benzoyl)-11H-benzo-[a]carbazol-8-carbonyl]-phenoxy}-2,2,3,3,4,4,5,5-octafluoro-hexyloxy)-phenyl]-[11-(2-ethylhexyl)-5-(2,4,6-trimethyl-benzoyl)-11H-benzo[a]carbazol-8-yl]-methanone

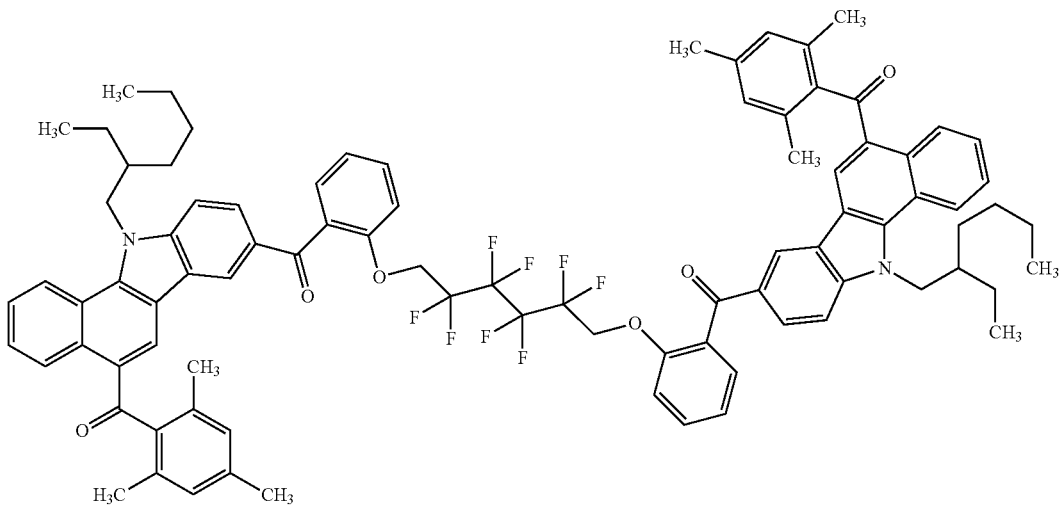 [SMILES: CCCCC(CC)Cn1c2ccc(C(=O)c3ccccc3OCC(F)(F)C(F)(F)C(F)(F)C(F)(F)COc3ccccc3C(=O)c3ccc4c(c3)c3cc(C(=O)c5c(C)cc(C)cc5C)c5ccccc5c3n4CC(CC)CCCC)cc2c2cc(C(=O)c3c(C)cc(C)cc3C)c3ccccc3c21]

To [11-(2-ethylhexyl)-5-(2,4,6-trimethyl-benzoyl)-11,11b-dihydro-4aH-benzo[a]carbazol-8-yl]-(2-fluoro-phenyl)-methanone (2.99 g; 5.00 mmol) in pyridine (15 mL) are added 2,2,3,3,4,4,5,5-octafluoro-1,6-hexanediol (0.59 g; 2.25 mmol) and sodium hydride (0.40 g; 10.00 mmol) at room temperature. The mixture is heated at 100° C., and it is stirred overnight. After it is cooled at room temperature, the reaction mixture is poured into ice-water. The crude product is extracted twice with ethyl acetate. The combined organic layer is washed with water and brine, dried over $MgSO_4$, and concentrated to give a brown solid. The crude product is purified by column chromatography on silica gel eluting with a mixed solvent of $CH_2Cl_2$ and n-hexane (3:1) to give a yellow solid (0.74 g, 23%). The structure is confirmed by $^1$H-NMR spectrum ($CDCl_3$). δ [ppm]: 0.80-0.92 (m), 1.16-1.47 (m), 2.20 (m), 2.22 (d), 2.26-2.29 (m), 2.40 (d), 3.31 (m), 4.68 (t), 4.74 (t), 6.97 (d), 7.12-7.31 (m), 7.47-7.59 (m), 7.68-7.83 (m), 8.31 (d), 8.38 (s), 8.63 (t), 8.64 (s), 9.57 (m); $^{19}$F-NMR spectrum ($CDCl_3$). δ [ppm]: −123.96, −119.86

1.d Synthesis of [11-(2-Ethylhexyl)-5-(2,4,6-trim-ethyl-benzoyl)-11H-benzo[a]carbazol-8-yl]-{2-[6-(2-{[11-(2-ethylhexyl)-5-(2,4,6-trimethyl-benzoyl)-11H-benzo[a]-carbazol-8-yl]-hydroxyimino-methyl}-phenoxy)-2,2,3,3,4,4,5,5-octafluoro-hexyloxy]-phenyl}-methanone oxime

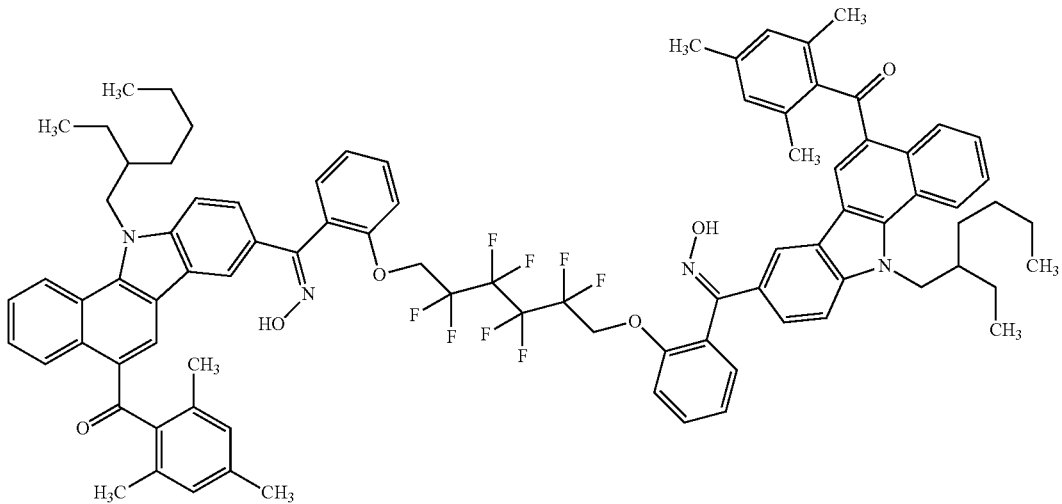 [SMILES: CCCCC(CC)Cn1c2ccc(/C(=N\O)c3ccccc3OCC(F)(F)C(F)(F)C(F)(F)C(F)(F)COc3ccccc3/C(=N/O)c3ccc4c(c3)c3cc(C(=O)c5c(C)cc(C)cc5C)c5ccccc5c3n4CC(CC)CCCC)cc2c2cc(C(=O)c3c(C)cc(C)cc3C)c3ccccc3c21]

To [2-(6-{2-[11-(2-ethylhexyl)-5-(2,4,6-trimethyl-benzoyl)-11H-benzo[a]carbazol-8-carbonyl]-phenoxy}-2,2,3,3,4,4,5,5-octafluoro-hexyloxy)-phenyl]-[11-(2-ethylhexyl)-5-(2,4,6-trimethyl-benzoyl)-11H-benzo[a]carbazol-8-yl]-methanone (0.74 g; 0.52 mmol) in pyridine (5 mL) is added hydroxylammonium chloride (0.14 g; 2.08 mmol) at room temperature. The mixture is heated to 100° C., and then the mixture is stirred overnight. After it is cooled to room temperature, the reaction mixture is poured into ice-water, and the crude is extracted twice with ethyl acetate. The combined organic layer is washed with water and brine, dried over MgSO$_4$, and concentrated to give an orange solid. The crude product is purified by column chromatography on silica gel eluting with a mixed solvent of CH$_2$Cl$_2$ and n-hexane (1:1) to give a yellow solid (0.53 g, 36%). The structure is confirmed by $^1$H-NMR spectrum (CDCl$_3$). δ [ppm]: 0.80 (t), 0.87 (t), 1.17-1.59 (m), 2.15 (s), 2.25 (m), 2.36 (s), 4.47 (m), 4.66-4.70 (m), 6.90 (s), 7.07 (d), 7.20-7.26 (m), 7.44-7.84 (m), 7.56 (d), 7.66-7.74 (m), 7.96 (s), 8.23 (s), 8.61 (d), 9.50 (s); $^{19}$F-NMR spectrum (CDCl$_3$). δ [ppm]: −127.77, −123.73

1.e [11-(2-Ethylhexyl)-5-(2,4,6-trimethyl-benzoyl)-11H-benzo[a]carbazol-8-yl]-{2-[6-(2-{[11-(2-ethyl-hexyl)-5-(2,4,6-trimethyl-benzoyl)-11H-benzo[a]carbazol-8-yl]-acetoxyimino-methyl}-phenoxy)-2,2,3,3,4,4,5,5-octafluoro-hexyloxy]-phenyl}-methanone oxime O-acetate

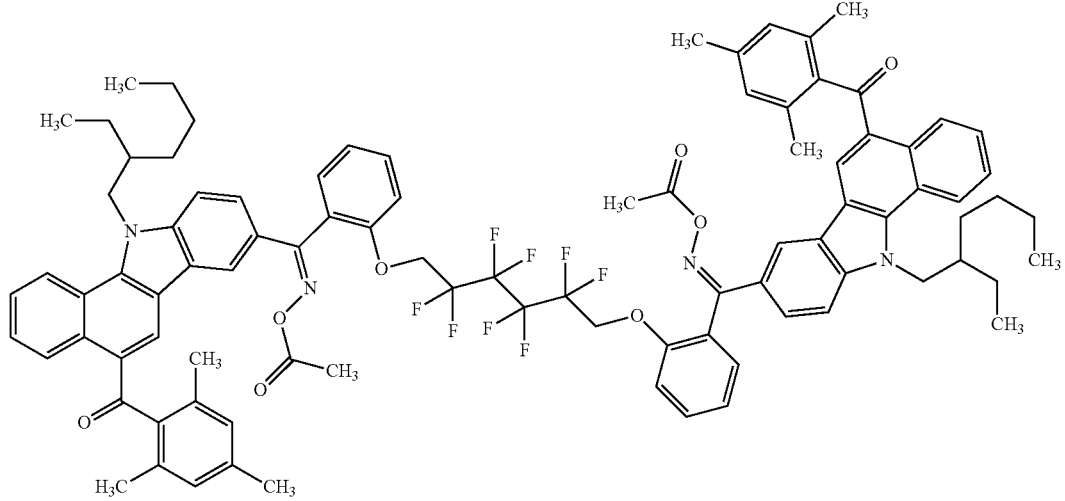 [SMILES: CCCCC(CC)Cn1c2ccc(/C(=N\OC(C)=O)c3ccccc3OCC(F)(F)C(F)(F)C(F)(F)C(F)(F)COc3ccccc3/C(=N/OC(C)=O)c3ccc4c(c3)c3cc(C(=O)c5c(C)cc(C)cc5C)c5ccccc5c3n4CC(CC)CCCC)cc2c2cc(C(=O)c3c(C)cc(C)cc3C)c3ccccc3c21]

To [11-(2-ethylhexyl)-5-(2,4,6-trimethyl-benzoyl)-11H-benzo[a]carbazol-8-yl]-{2-[6-(2-{[11-(2-ethylhexyl)-5-(2,4,6-trimethyl-benzoyl)-11H-benzo[a]carbazol-8-yl]-hydroxy-imino-methyl}-phenoxy)-2,2,3,3,4,4,5,5-octafluoro-hexyloxy]-phenyl}-methanone oxime (0.27 g; 0.19 mmol) in ethyl acetate (5 mL) are added triethylamine (0.19 g; 1.86 mmol) and acetyl chloride (0.15 g; 1.86 mmol) at 0° C. The mixture is stirred for 4.5 hours. After the reaction is completed, the reaction mixture is added into water. Then, the crude product is extracted with ethyl acetate. The combined organic layer is washed with water and brine, dried over MgSO$_4$, and concentrated to give a yellow solid. The crude product is purified by column chromatography on silica gel eluting with a mixed solvent of methanol and CH$_2$Cl$_2$ (2:98) to give a yellow solid (0.13 g; 46%). The structure is confirmed by $^1$H-NMR spectrum (CDCl$_3$). δ [ppm]: 0.78 (t), 0.82 (t), 1.14-1.39 (m), 1.99 (s), 2.17 (s), 2.22-2.25 (m), 2.35 (s), 4.49 (m), 4.67 (m), 6.91-6.95 (m), 7.09-7.16 (m), 7.34-7.47 (m), 7.66-7.76 (m), 8.35 (s), 8.43 (d), 8.61 (d), 9.52 (dd); $^{19}$F-NMR spectrum (CDCl$_3$). δ [ppm]: −123.82, −119.71

Example 2

Synthesis of 1-(11-(2-ethylhexyl)-5-{4-[6-(4-{[11-(2-ethylhexyl)-8-(3,5,5-trimethyl-hexanoyl)-11H-benzo[a]carbazol-5-yl]-acetoxyimino-methyl}-phenoxy)-2,2,3,3,4,4,5,5-octafluoro-hexyloxy]-benzoyl}-11H-benzo[a]carbazol-8-yl}-3,5,5-trimethyl-hexan-1-one oxime O-acetate 2.a Synthesis of 1-{11-(2-ethylhexyl)-5-[4-(6-{4-[11-(2-ethylhexyl)-8-(3,5,5-trimethyl-hexanoyl)-11H-benzo[a]carbazole-5-carbonyl]-phenoxy}-2,2,3,3,4,4,5,5-octafluoro-hexyloxy)-benzoyl]-11H-benzo[a]carbazol-8-yl}-3,5,5-trimethyl-hexan-1-one

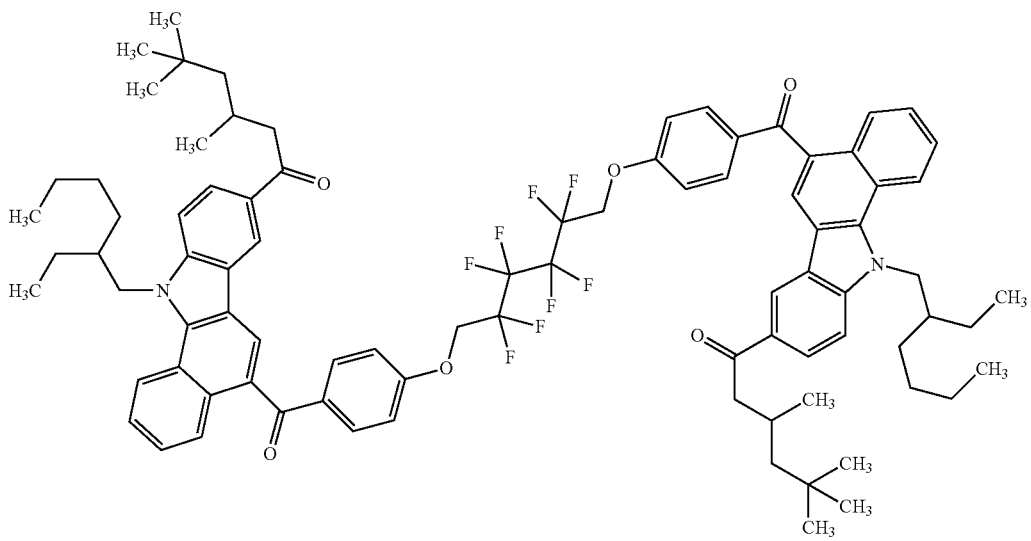 [SMILES: CCCCC(CC)Cn1c2ccc(C(=O)CC(C)CC(C)(C)C)cc2c2cc(C(=O)c3ccc(OCC(F)(F)C(F)(F)C(F)(F)C(F)(F)COc4ccc(C(=O)c5cc6c7cc(C(=O)CC(C)CC(C)(C)C)ccc7n(CC(CC)CCCC)c6c6ccccc56)cc4)cc3)c3ccccc3c21]

To 1-[11-(2-ethylhexyl)-5-(4-fluoro-benzoyl)-11H-benzo[a]carbazol-8-yl]-3,5,5-trimethyl-hexan-1-one (1.18 g; 2.00 mmol) in pyridine (5 mL) are added 2,2,3,3,4,4,5,5-octafluoro-1,6-hexanediol (0.24 g; 0.90 mmol) and sodium hydroxide (0.16 g; 4 mmol) at 80° C., and the mixture is stirred at 100° C. for 43 hours. After the reaction is completed, the reaction mixture is cooled to room temperature, and poured into ice water. The crude product is extracted with ethyl acetate, and the combined organic layer is washed with water and brine, dried over MgSO$_4$, and concentrated to give a yellow resin. The crude is purified by column chromatography on silica gel eluting with a mixed solvent of CH$_2$Cl$_2$ and n-hexane (1:1) to give a yellow solid (0.40 g; 32%). The structure is confirmed by $^1$H-NMR spectrum (CDCl$_3$). δ [ppm]: 0.81-0.92 (m), 1.03 (d), 1.18-1.46 (m), 2.27-2.35 (m), 2.89-2.96 (m), 3.02-3.08 (m), 4.60 (t), 4.74 (m), 7.06 (d), 7.58 (m), 7.66 (t), 7.99 (m), 8.14 (dd), 8.33 (s), 8.43 (d), 8.61 (d), 8.68 (d); $^{19}$F-NMR spectrum (CDCl$_3$). δ [ppm]: −123.32, −119.45.

2.b Synthesis of 1-(11-(2-Ethylhexyl)-5-{4-[6-(4-{[11-(2-ethylhexyl)-8-(3,5,5-trimethyl-hexanoyl)-11H-benzo[a]carbazol-5-yl]-hydroxylimino-methyl}-phenoxy)-2,2,3,3,4,4,5,5-octafluoro-hexyloxy]-benzoyl}-11H-benzo[a]carbazol-8-yl}-3,5,5-trimethyl-hexan-1-one oxime over MgSO$_4$, and concentrated to give an orange solid. The crude is purified by column chromatography on silica gel eluting with a mixed solvent of methanol and CH$_2$Cl$_2$ (2:98) to give a yellow solid (0.18 g; 17%). The structure is confirmed by $^1$H-NMR spectrum (CDCl$_3$). δ [ppm]: 0.80-0.85 (m), 0.88-0.92 (m), 1.17-1.48 (m), 1.93 (br), 2.28 (br), 2.88 (d), 4.59 (t), 4.71 (br), 7.05 (d), 7.55-7.61 (m), 7.63-7.67 (m), 7.73 (d), 7.98 (d), 8.25 (d), 8.55 (d), 8.61 (d); $^{19}$F-NMR spectrum (CDCl$_3$). δ [ppm]: −123.36, −119.36.

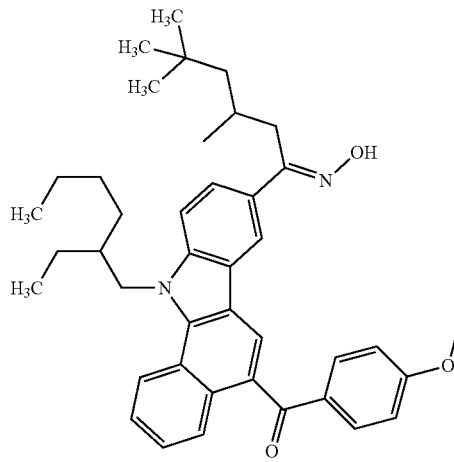

To 1-{11-(2-ethylhexyl)-5-[4-(6-{4-[11-(2-ethylhexyl)-8-(3,5,5-trimethyl-hexanoyl)-11H-benzo[a]carbazole-5-carbonyl]-phenoxy}-2,2,3,3,4,4,5,5-octafluoro-hexyloxy)-benzoyl]-11H-benzo[a]carbazol-8-yl}-3,5,5-trimethyl-hexan-1-one (0.40 g; 0.28 mmol) in ethyl acetate (5 mL) and N-methylpyrrolidone (NMP) (0.5 mL) are added sodium acetate (94 mg; 1.14 mmol) and hydroxylammonium chloride (81 mg; 1.14 mmol) at 80° C. The mixture is stirred at 80° C. overnight. After the reaction is completed, the reaction mixture is cooled to room temperature, and poured into ice-water. The crude product is extracted with ethyl acetate. The combined organic layer is washed with water and brine, dried 2.c Synthesis of 1-(11-(2-ethylhexyl)-5-{4-[6-(4-{[11-(2-ethylhexyl)-8-(3,5,5-trimethyl-hexanoyl)-11H-benzo[a]carbazol-5-yl]-acetoxylimino-methyl}-phenoxy)-2,2,3,3,4,4,5,5-octafluoro-hexyloxy]-benzoyl}-11H-benzo[a]carbazol-8-yl}-3,5,5-trimethyl-hexan-1-one oxime O-acetate

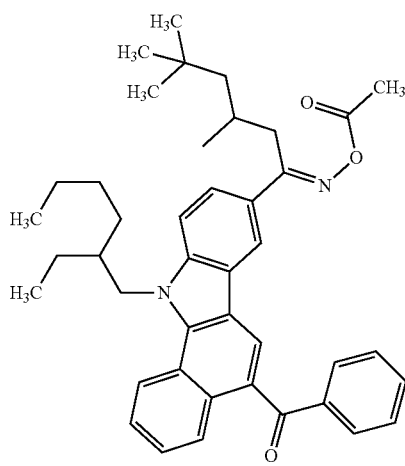
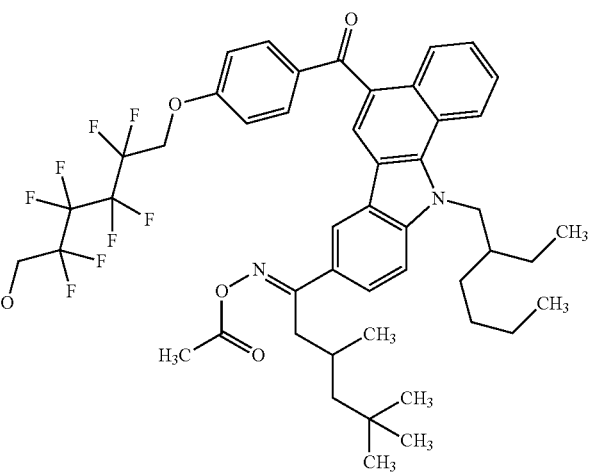

To 1-(11-(2-ethylhexyl)-5-{4-[6-(4-{[11-(2-ethylhexyl)-8-(3,5,5-trimethyl-hexanoyl)-11H-benzo[a]carbazol-5-yl]-hydroxylimino-methyl}-phenoxy)-2,2,3,3,4,4,5,5-octafluoro-hexyloxy]-benzoyl}-11H-benzo[a]carbazol-8-yl}-3,5,5-trimethyl-hexan-1-one oxime (0.18 g; 0.13 mmol) in ethyl acetate (3 mL) are added triethyl amine (0.13 g; 1.25 mmol) and acetyl chloride (0.10 g; 1.25 mmol) at 0° C. The mixture is stirred at room temperature for 6 hours. After the reaction is completed, the reaction mixture is added into ice-water. Then, the crude product is extracted with ethyl acetate. The combined organic layer is washed with water and brine, dried over MgSO$_4$, and concentrated to give a yellow solid. The crude product is purified by column chromatography on silica gel eluting with a mixed solvent of methanol and CH$_2$Cl$_2$ (0.5:99.5) to give a yellow solid (90 mg; 47%). The structure is confirmed by $^1$H-NMR spectrum (CDCl$_3$). δ [ppm]: 0.79-0.84 (m), 0.89-0.93 (m), 1.18-1.43 (m), 1.93 (br), 2.24 (s), 2.28-2.30 (m), 2.90-2.95 (m), 4.59 (t), 4.75-4.77 (m), 7.05 (d), 7.59 (d), 7.66 (t), 7.87 (dd), 7.98 (d), 8.32 (s), 8.40 (s), 8.47 (d), 8.63 (d), $^{19}$F-NMR spectrum (CDCl$_3$). δ [ppm]: –123.35, –119.51.

Example 3

Synthesis of 4-(11-(2-ethylhexyl)-5-{4-[3-(1-acetoxyimino-3-propoxycarbonyl-propyl)carbazole-9-yl]-benzoyl}-11H-benzo[a]carbazol-8-yl)-4-acetoxy-imino-butyric acid ethyl ester 3.a Synthesis of [11-(2-ethylhexyl)-11H-benzo[a]carbazol-5-yl]-(4-fluorophenyl)-methanone

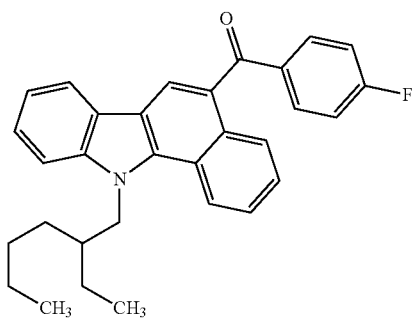 [SMILES: CCCCC(CC)Cn1c2ccccc2c2cc(C(=O)c3ccc(F)cc3)c3ccccc3c21]

To 11-(2-ethylhexyl)-11H-benzo[a]carbazole (10.0 g, 30.6 mmol) in CH$_2$Cl$_2$ (150 mL) are added 4-fluorobenzoyl chloride (5.03 g, 31.7 mmol) and AlCl$_3$ (4.58 g, 34.3 mmol) at 0° C. After stirring for 0.5 hour, the reaction mixture is stirred for 2 hours at room temperature. The reaction mixture is poured into ice-water, and the crude product is extracted with CH$_2$Cl$_2$. The organic layer is washed with water and brine, dried over MgSO$_4$. After concentration, the crude product is purified by column chromatography on silica gel eluting with a mixed solvent of n-hexane and CH$_2$Cl$_2$ (1:1) to obtain an off-white solid (8.14 g; 57%). The structure is confirmed by $^1$H-NMR spectrum (CDCl$_3$). δ [ppm]: 0.83 (t), 0.89 (t), 1.18-1.52 (m), 2.24-2.31 (m), 4.68-4.80 (m), 7.16 (t), 7.31 (t), 7.50 (t), 7.55-7.60 (m), 7.65 (t), 7.97 (dd), 8.06 (d), 8.31 (s), 8.50 (d), 8.65 (d); $^{19}$F-NMR spectrum (CDCl$_3$). δ [ppm]–106.30.

3.b Synthesis of 4-(11-(2-Ethylhexyl)-5-(4-fluoro-benzoyl)-11H-benzo[a]carbazol-8-yl]-4-oxo-butyric acid ethyl ester

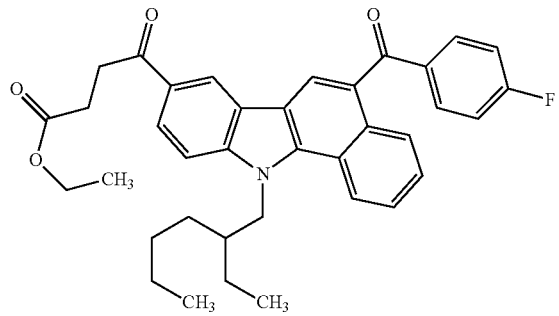 [SMILES: CCCCC(CC)Cn1c2ccc(C(=O)CCC(=O)OCC)cc2c2cc(C(=O)c3ccc(F)cc3)c3ccccc3c21]

To compound the [11-(2-ethylhexyl)-11H-benzo[a]carbazol-5-yl]-(4-fluorophenyl)methanone (4.025 g, 8.912 mmol) in CH$_2$Cl$_2$ (45 mL) are added ethylsuccinyl chloride (1.64 g, 10.0 mmol) and AlCl$_3$ (3.97 g, 29.8 mmol) at 0° C. After stirring for 0.5 hour, the reaction mixture is stirred for 2 hours at room temperature. The reaction mixture is poured into ice-water, and the crude product is extracted with CH$_2$Cl$_2$. The organic layer is washed with water and brine, dried over MgSO$_4$. After concentration, the residue is recrystallized with a mixed solvent of CH$_2$Cl$_2$ and n-hexane to obtain an off-white solid (3.92 g; 76%). The structure is confirmed by $^1$H-NMR spectrum (CDCl$_3$) δ [ppm]: 0.83 (t), 0.89 (t), 1.18-1.50 (m), 2.24-2.32 (m), 2.82 (t), 3.45 (t), 4.17 (q), 4.66-4.81 (m), 7.60 (d), 7.61 (t), 7.68 (t), 7.99 (dd), 8.17 (d), 8.31 (s), 8.50 (d), 8.61 (d), 8.71 (s); $^{19}$F-NMR spectrum (CDCl$_3$). δ [ppm]: –105.75.

3.c Synthesis of 4-[5-(4-Carbazol-9-yl-benzoyl)-11-(2-ethylhexyl)-11H-benzo[a]carbazol-8-yl]-4-oxo-butyric acid ethyl ester

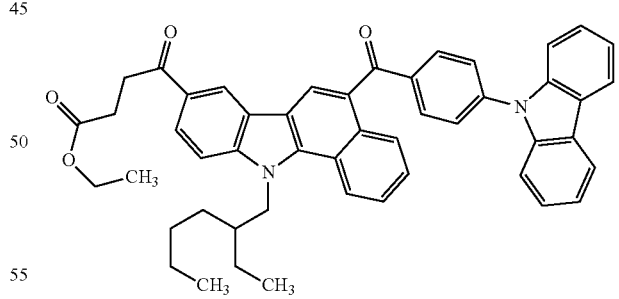

To 4-(11-(2-ethylhexyl)-5-(4-fluoro-benzoyl)-11H-benzo[a]carbazol-8-yl]-4-oxo-butyric acid ethyl ester (1.01 g, 1.75 mmol) in dimethylsulfoxide (DMSO) (10 mL) are added K$_2$CO$_3$ (738 mg, 5.33 mmol) and carbazole (297 mg, 1.77 mmol). The reaction mixture is heated to 150° C. and stirred overnight. After cooling to room temperature, the reaction mixture is poured into water, and the crude product is extracted with CH$_2$Cl$_2$. The organic layer is washed with water and brine, dried over MgSO$_4$. After concentration, the crude product is purified by column chromatography on silica gel eluting with CH$_2$Cl$_2$ to obtain a brown resin (760 mg; 60%). The structure is confirmed by $^1$H-NMR spectrum (CDCl$_3$). δ [ppm]: 0.84 (t), 0.92 (t), 1.20-1.52 (m), 2.28-2.36 (m), 2.82 (t), 3.48 (t), 4.16 (q), 4.74-4.21 (m), 7.33 (t), 7.46 (t), 7.60 (d), 7.63 (d), 7.68 (t), 7.72 (t), 7.77 (d), 8.15 (t), 8.19 (d), 8.22 (d), 8.50 (s), 8.58 (d), 8.67 (d), 8.81 (s).

3.d Synthesis of 4-(11-(2-ethylhexyl)-5-{4-[3-(3-propoxycarbonyl-propionyl)-carbazole-9-yl]-benzoyl}-11H-benzo[a]carbazol-8-yl)-4-oxo-butyric acid ethyl ester

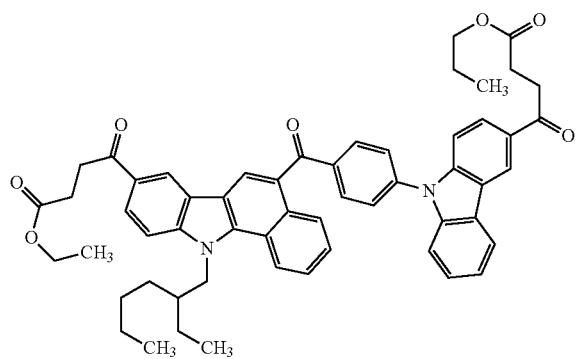 [SMILES: CCCCC(CC)Cn1c2ccc(C(=O)CCC(=O)OCC)cc2c2cc(C(=O)c3ccc(-n4c5ccccc5c5cc(C(=O)CCC(=O)OCCC)ccc54)cc3)c3ccccc3c21]

To 4-[5-(4-carbazol-9-yl-benzoyl)-11-(2-ethylhexyl)-11H-benzo[a]carbazol-8-yl]-4-oxo-butyric acid ethyl ester (760 mg, 1.04 mmol) in CH$_2$Cl$_2$ (5 mL) are added ethylsuccinyl chloride (184 mg, 1.11 mmol) and AlCl$_3$ (737 mg, 5.52 mmol) at 0° C. After stirring for 0.5 hour, the reaction mixture is stirred for 2 hours at room temperature. The reaction mixture is poured into ice-water, and the crude product is extracted with CH$_2$Cl$_2$. The organic layer is washed with water and brine, dried over MgSO$_4$. After concentration, the crude product is purified by column chromatography on silica gel eluting with a mixed solvent of CH$_2$Cl$_2$ and AcOEt (10:1) to obtain off-white resin (257 mg; 30%). The structure is confirmed by $^1$H-NMR spectrum (CDCl$_3$). δ [ppm]: 0.84 (t), 0.92 (t), 1.22-1.55 (m), 2.30-2.38 (m), 2.84 (t), 3.49 (t), 4.12 (q), 4.16 (q), 4.71-4.88 (m), 7.40 (t), 7.51 (t), 7.58-7.72 (m), 7.76 (d), 8.14 (d), 8.19 (d), 8.21 (d), 8.25 (d), 8.50 (s), 8.60 (d), 8.67 (d), 8.82 (d).

3.e Synthesis of 4-(11-(2-Ethylhexyl)-5-{4-[3-(1-hydroxyimino-3-propoxycarbonyl-propyl)-carbazole-9-yl]-benzoyl}-11H-benzo[a]carbazol-8-yl)-4-hydroxyimino-butyric acid ethyl ester

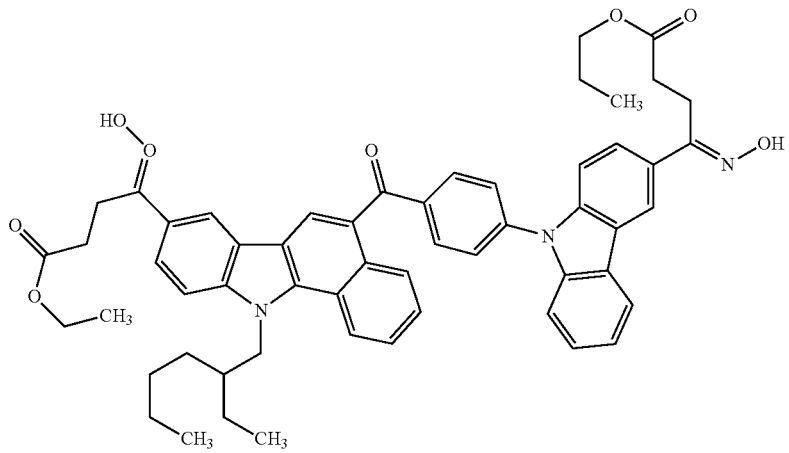

To 4-(11-(2-ethylhexyl)-5-{4-[3-(3-propoxycarbonyl-propionyl)-carbazole-9-yl]-benzoyl}-11H-benzo[a]carbazol-8-yl)-4-oxo-butyric acid ethyl ester (257 mg, 0.295 mmol) in pyridine (10 mL) is added hydroxylammonium chloride (62 mg, 0.89 mmol), and it is stirred at 80° C. for 5 hours. After it is cooled to room temperature, the reaction mixture is poured into water, and the crude product is extracted with ethyl acetate. The organic layer is washed with water and brine, dried over MgSO$_4$. After concentration, the crude product is purified by column chromatography on silica gel eluting with ethyl acetate to obtain an off-white resin (260 mg; 95%). The structure is confirmed by $^1$H-NMR spectrum (CDCl$_3$). δ [ppm]: 0.83 (t), 0.90 (t), 1.20-1.53 (m), 2.25-2.33 (m), 2.68 (t), 3.26 (t), 4.08 (q), 4.12 (q), 4.76-4.78 (m), 7.33 (t), 7.46 (t), 7.56-7.84 (m), 8.16 (d), 8.20 (d), 8.36 (d), 8.44 (s), 8.65 (d).

3.f Synthesis of 4-(11-(2-ethylhexyl)-5-{4-[3-(1-acetoxyimino-3-propoxycarbonyl-propyl)-carbazole-9-yl]-benzoyl}-11H-benzo[a]carbazol-8-yl)-4-acetoxyimino-butyric acid ethyl ester

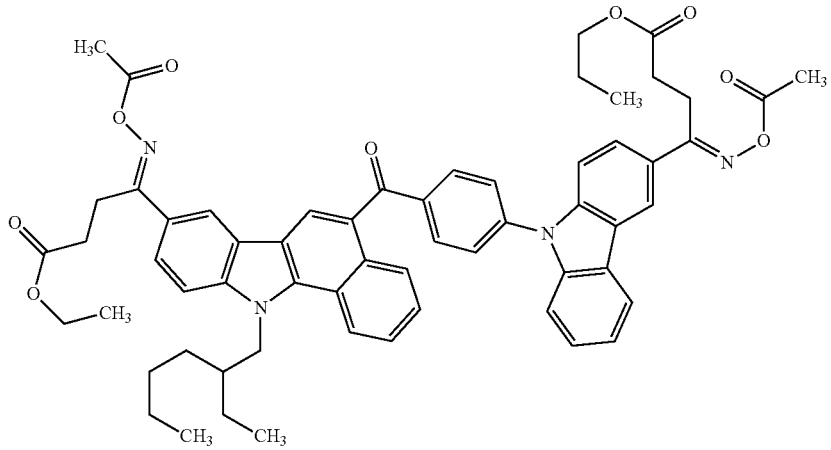 [SMILES: CCCCC(CC)Cn1c2ccc(/C(CCC(=O)OCC)=N/OC(C)=O)cc2c2cc(C(=O)c3ccc(-n4c5ccccc5c5cc(/C(CCC(=O)OCCC)=N/OC(C)=O)ccc54)cc3)c3ccccc3c21]

To 4-(11-(2-ethylhexyl)-5-{4-[3-(1-hydroxyimino-3-propoxycarbonyl-propyl)-carbazole-9-yl]-benzoyl}-11H-benzo[a]carbazol-8-yl)-4-hydroxyimino-butyric acid ethyl ester (260 mg, 0.289 mmol) in tetrahydrofurane (THF) (5 mL) are added triethylamine (86 mg, 0.84 mmol) and acetyl chloride (66 mg, 0.84 mmol) at 0° C. After stirring for 1.5 hours, the reaction mixture is poured into water, and the crude product is extracted with ethyl acetate. The organic layer is washed with water and brine, dried over $MgSO_4$. After concentration, the crude product is purified by column chromatography on silica gel eluting with ethyl acetate to obtain an off-white resin (169 mg; 60%). The structure is confirmed by $^1$H-NMR spectrum (CDCl$_3$). δ [ppm]: 0.84 (t), 0.91 (t), 1.19-1.54 (m), 2.28 (s), 2.31 (s), 2.60-2.69 (m), 3.27-3.35 (m), 4.09 (q), 4.14 (q), 4.73-4.85 (m), 7.36 (t), 7.49 (t), 7.56-7.78 (m), 7.85 (d), 7.89 (d), 8.20 (d), 8.22 (d), 3.23 (d), 8.49 (s), 8.53 (s), 8.60 (d), 8.67 (d).

Example 4

Synthesis of 1,6-bis-[11-(2-ethylhexyl)-5-(2,4,6-trimethyl-benzoyl)-11H-benzo[a]carbazol-8-yl]hexane-1,6-dione dioxime O-diacetate 4.a Synthesis of 1,6-bis-[11-(2-ethylhexyl)-5-(2,4,6-trimethyl-benzoyl)-11H-benzo[a]-carbazol-8-yl]-hexane-1,6-dione

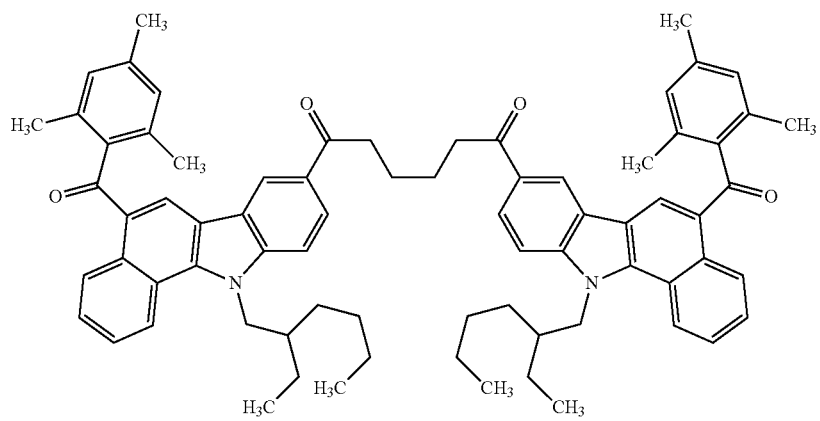

To 11-(2-ethylhexyl)-11H-benzo[a]carbazole (1.65 g; 5.00 mmol) in $CH_2Cl_2$ (15 mL) are added 2,4,6-trimethylbenzoyl chloride (0.92 g; 5.11 mmol) and $AlCl_3$ (0.70 g; 5.25 mmol) at 0° C. After stirring at room temperature for 1 hour, $AlCl_3$ (0.70 g; 5.30 mmol) is added at 0° C. and adipoyl chloride (0.43 g; 2.33 mmol) is added dropwise, and then the mixture is stirred at room temperature overnight. The reaction mixture is poured into ice-water, and the crude product is extracted twice with CH$_2$Cl$_2$. The combined organic layer is washed with water and brine, dried over MgSO$_4$, and concentrated to give a green solid. The crude product is purified by column chromatography on silica gel eluting with a mixed solvent of CH$_2$Cl$_2$ and n-hexane (1:1) to give a beige solid (0.85 g; 34.4%). The structure is confirmed by $^1$H-NMR spectrum (CDCl$_3$). δ [ppm]: 0.82 (t, 6H), 0.89 (t, 6H), 1.17-1.42 (m, 16H), 1.93 (br, 4H), 2.21 (s, 12H), 2.26 (m, 2H), 2.40 (s, 6H), 3.18 (br, 4H), 4.69 (m, 4H), 6.97 (s, 4H), 7.54 (d, 2H), 7.69-7.78 (m, 4H), 8.08 (s, 2H), 8.39 (s, 2H), 8.61 (br, 4H), 9.53 (d, 2H).

4.b Synthesis of 1,6-bis-[11-(2-ethylhexyl)-5-(2,4,6-trimethyl-benzoyl)-11H-benzo[a]-carbazol-8-yl]-hexane-1,6-dione dioxime mixture is stirred at 100° C. overnight. After the reaction is completed, the reaction mixture is cooled at room temperature, and poured into ice-water. The crude product is extracted with ethyl acetate. The combined organic layer is washed with water and brine, dried over MgSO$_4$, and concentrated to give a yellow solid. The crude is purified by column chromatography on silica gel eluting with a mixed solvent of CH$_2$Cl$_2$ and n-hexane (3:1) to give a yellow solid (0.40 g; 46.2%). The structure is confirmed by $^1$H-NMR spectrum (CDCl$_3$). δ [ppm]: 0.79-0.86 (m, 12H), 1.15-1.38 (m, 16H), 1.70 (br, 2H), 2.17 (s, 12H), 2.20 (m, 2H), 2.33 (s, 6H), 2.93 (br, 4H), 4.57 (m, 4H), 6.92 (s, 4H), 7.41 (d, 2H), 7.61 (dd, 2H), 7.67-7.77 (m, 4H), 8.14 (s, 2H), 8.34 (s, 2H), 8.58 (d, 2H), 9.55 (d, 2H).

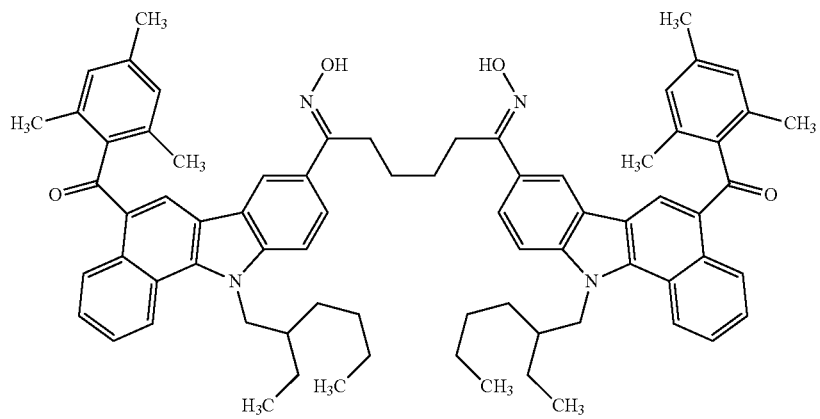

To 1,6-bis-[11-(2-ethylhexyl)-5-(2,4,6-trimethyl-benzoyl)-11H-benzo[a]carbazol-8-yl]-hexane-1,6-dione (0.85 g; 0.80 mmol) in pyridine (8 mL) is added hydroxylammounim chloride (0.23 g; 3.18 mmol) at 60° C., and the 4.c Synthesis of 1,6-bis-[11-(2-ethylhexyl)-5-(2,4,6-trimethyl-benzoyl)-11H-benzo[a]-carbazol-8-yl] hexane-1,6-dione dioxime O-diacetate

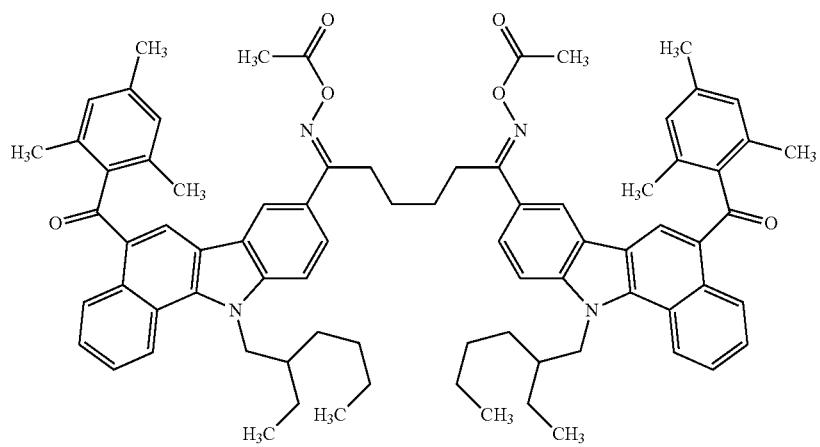

To 1,6-bis-[11-(2-ethylhexyl)-5-(2,4,6-trimethyl-benzoyl)-11H-benzo[a]carbazol-8-yl]-hexane-1,6-dione dioxime (0.40 g; 0.37 mmol) in dimethyl acetamide (5 mL) are added triethyl amine (0.12 g; 1.23 mmol) and acetyl chloride (0.09 g; 1.15 mmol) at 0° C. The mixture is stirred at room temperature overnight. After the reaction is completed, the reaction mixture is added into ice water. Then, the crude product is extracted with ethyl acetate. The combined organic layer is washed with water and brine, dried over MgSO$_4$, and concentrated to give a beige powder. The crude product is purified by column chromatography on silica gel eluting with a mixed solvent of CH$_2$Cl$_2$ and n-hexane (3:1) to give a yellow solid (0.35 g; 82%). The structure is confirmed by $^1$H-NMR spectrum (CDCl$_3$). δ [ppm]: 0.79-0.85 (m, 12H), 1.18-1.33 (m, 16H), 1.72 (br, 4H), 2.19-2.22 (m, 20H), 2.35 (s, 6H), 2.98 (br, 4H), 4.50 (m, 4H), 6.93 (s, 4H), 7.39 (d, 2H), 7.61 (d, 2H), 7.68-7.78 (m, 4H), 8.25 (s, 2H), 8.34 (s, 2H), 8.55 (d, 2H), 9.53 (d, 2H).

Example 5

Synthesis of 1-[11-[4-(1-acetoxyimino-ethyl)-phenyl]-5-(2,4,6-trimethyl-benzoyl)-11H-benzo[a]carbazol-8-yl]-3-methyl-butan-1-one oxime O-acetate 5.a Synthesis of 1-(4-Benzo[a]carbazol-11-yl-phenyl)-ethanone

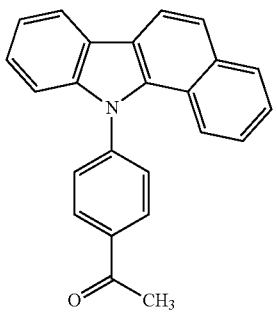 [SMILES: CC(=O)c1ccc(-n2c3ccccc3c3ccc4ccccc4c32)cc1]

To 11H-benzo[a]carbazole (2.00 g, 9.22 mmol) in DMSO (20 mL) is added K$_2$CO$_3$ (3.85 g, 27.9 mmol) at 180° C., and then the mixture is stirred for 1 hour. To the mixture is added 4-fluoroacetophenone (1.28 g, 9.228 mmol). After stirring for 8 hours, the reaction mixture is cooled to room temperature, and poured into water. The crude product is extracted with ethyl acetate, and it is washed with water and brine. The organic layer is dried over MgSO$_4$. After concentration, the crude product is purified by column chromatography on silica gel eluting with CH$_2$Cl$_2$ to obtain an off-white solid (160 mg; 5%). The structure is confirmed by $^1$H-NMR spectrum (CDCl$_3$). δ [ppm]: 2.75 (s), 7.20 (d), 7.23 (t), 7.34-7.46 (m), 7.65 (d), 7.75 (d), 8.00 (d), 8.19 (d), 8.22 (d), 8.25 (d).

5.b Synthesis of 1-{4-[5-(2,4,6-trimethyl-benzoyl)-benzo[a]carbazol-11-yl]-phenyl}-ethanone

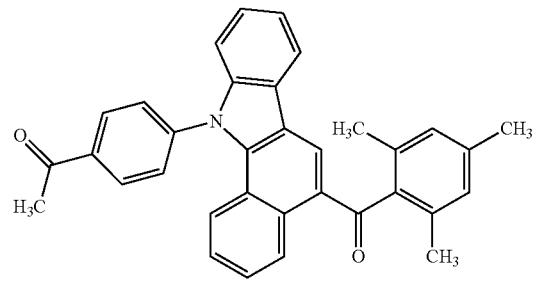 [SMILES: CC(=O)c1ccc(-n2c3ccccc3c3cc(C(=O)c4c(C)cc(C)cc4C)c4ccccc4c32)cc1]

To 1-(4-benzo[a]carbazol-11-yl-phenyl)-ethanone (649 mg, 1.93 mmol) in CH$_2$Cl$_2$ (10 mL) are added 2,4,6-trimethylbenzoyl chloride (369 mg, 2.02 mmol) and AlCl$_3$ (1.50 g, 11.24 mmol) at 0° C. After stirring for 0.5 hour, the reaction mixture is stirred for 2 hours at room temperature. The reaction mixture is poured into ice-water, and the crude product is extracted with CH$_2$Cl$_2$. The organic layer is washed with water and brine, dried over MgSO$_4$. After concentration, the crude product is purified by column chromatography on silica gel eluting with a mixed solvent of n-hexane and CH$_2$Cl$_2$ (1:1) to obtain an off-white solid (383 mg; 41%). The structure is confirmed by $^1$H-NMR spectrum (CDCl$_3$). δ [ppm]: 2.22 (s), 2.41 (s), 2.77 (s), 6.97 (s), 7.15 (d), 7.30-7.34 (m), 7.39 (t), 7.51 (d), 7.63 (d), 7.65 (d), 8.01 (d), 8.28 (d), 8.28 (d), 8.39 (s), 9.53 (d).

5.c Synthesis of 1-[11-(4-acetyl-phenyl)-5-(2,4,6-trimethyl-benzoyl)-11H-benzo[a]-carbazol-8-yl]-3-methyl-butan-1-one

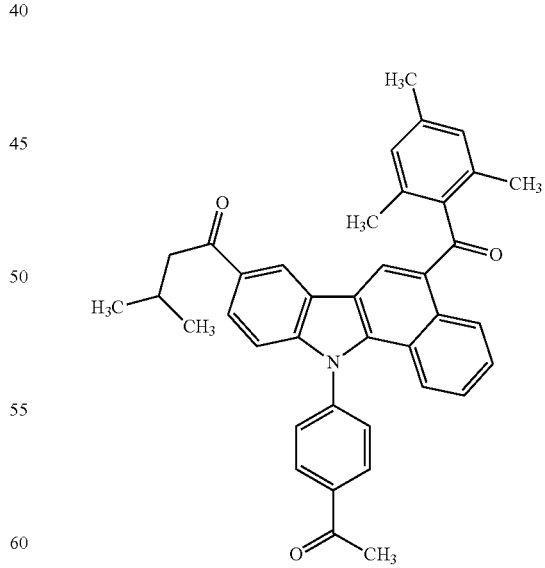

To 1-{4-[5-(2,4,6-trimethyl-benzoyl)-benzo[a]carbazol-11-yl]-phenyl}-ethanone (383 mg, 0.795 mmol) in CH$_2$Cl$_2$ (10 mL) are added isovaleroyl chloride (120 mg, 0.995 mmol) and AlCl$_3$ (350 mg, 2.62 mmol) at 0° C. After stirring for 2 hours, the reaction mixture is poured into ice-water, and the crude product is extracted with $CH_2Cl_2$. The organic layer is washed with water and brine, dried over $MgSO_4$. After concentration, the crude product is purified by column chromatography on silica gel eluting with $CH_2Cl_2$ to obtain an off-white solid (345 mg; 76%). The structure is confirmed by $^1$H-NMR spectrum ($CDCl_3$). δ [ppm]: 1.02 (d), 2.22 (s), 2.34 (m), 2.43 (s), 2.78 (s), 2.94 (d), 7.00 (s), 7.14 (d), 7.33 (t), 7.48 (d), 7.64-7.68 (m), 7.98 (d), 8.31 (d), 8.43 (s), 8.67 (s), 9.47 (d).

5.d Synthesis of 1-[11-[4-(1-hydroxyimino-ethyl)-phenyl]-5-(2,4,6-trimethyl-benzoyl)-11H-benzo[a]carbazol-8-yl]-3-methyl-butan-1-one oxime To 1-[11-(4-acetyl-phenyl)-5-(2,4,6-trimethyl-benzoyl)-11H-benzo[a]carbazol-8-yl]-3-methyl-butan-1-one (345 mg, 0.61 mmol) in pyridine (10 mL) is added hydroxylammonium chloride (136 mg, 1.95 mmol), and it is stirred at 80° C. overnight. After it is cooled at room temperature, the reaction mixture is poured into ice-water, and the crude product is extracted with ethyl acetate. The organic layer is washed with water and brine, dried over $MgSO_4$. After concentration, the residue is recrystallized with a mixed solvent of $CH_2Cl_2$ and n-hexane to obtain an off-white solid (345 mg; 76%). The structure is confirmed by $^1$H-NMR spectrum ($CDCl_3$). δ [ppm]: 0.94 (d), 1.98 (m), 2.22 (s), 2.41 (s), 2.44 (s), 2.84 (d), 6.98 (s), 7.13 (d), 7.32 (t), 7.54-7.59 (m), 7.64 (t), 7.96 (d), 8.22 (s), 8.40 (s), 9.48 (d).

5.e Synthesis of 1-[11-[4-(1-acetoxyimino-ethyl)-phenyl]-5-(2,4,6-trimethyl-benzoyl)-11H-benzo[a]carbazol-8-yl]-3-methyl-butan-1-one oxime O-acetate

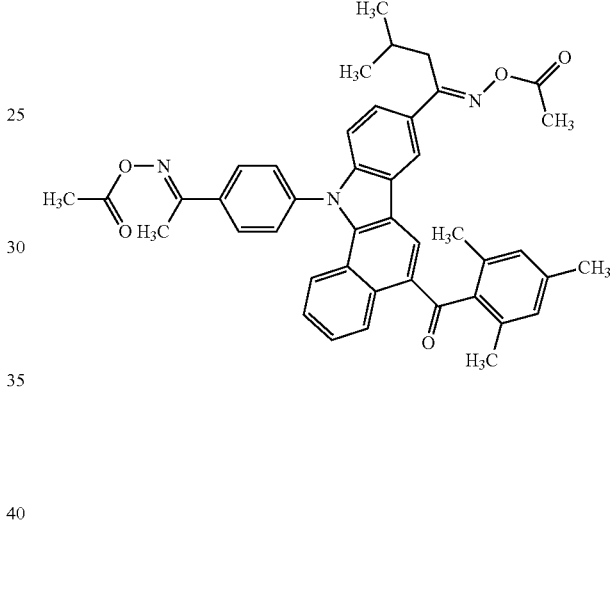

To 1-[11-[4-(1-hydroxyimino-ethyl)-phenyl]-5-(2,4,6-trimethyl-benzoyl)-11H-benzo[a]-carbazol-8-yl]-3-methyl-butan-1-one oxime (290 mg, 0.50 mmol) in THF (10 mL) are added triethylamine (144 mg, 1.42 mmol) and acetyl chloride (110 mg, 1.40 mmol) at 0° C. After stirring for 2 hours, the reaction mixture is poured into water, and the crude product is extracted with ethyl acetate. The organic layer is washed with water and brine, dried over $MgSO_4$. After concentration, the crude product is purified by column chromatography on silica gel eluting with a mixed solvent of $CH_2Cl_2$ and ethyl acetate (20:1) to obtain an off-white solid (210 mg; 62%). The structure is confirmed by $^1$H-NMR spectrum ($CDCl_3$). δ [ppm]: 0.95 (s), 2.22 (s), 2.26 (s), 2.33 (s), 2.40 (s), 2.55 (s), 2.87 (d), 6.98 (s), 7.12 (d), 7.33 (t), 7.56 (d), 7.58-7.67 (m), 8.09 (d), 8.39 (s), 8.42 (s), 9.43 (d).

Examples 6-21

The compounds of the examples 6-21 are prepared according to the methods as described above. The structures of the compounds are compiled in table 1.

TABLE 1
| Example | Structure | ¹H-NMR spectrum (CDCl₃) δ [ppm] |
|---|---|---|
| 6 | 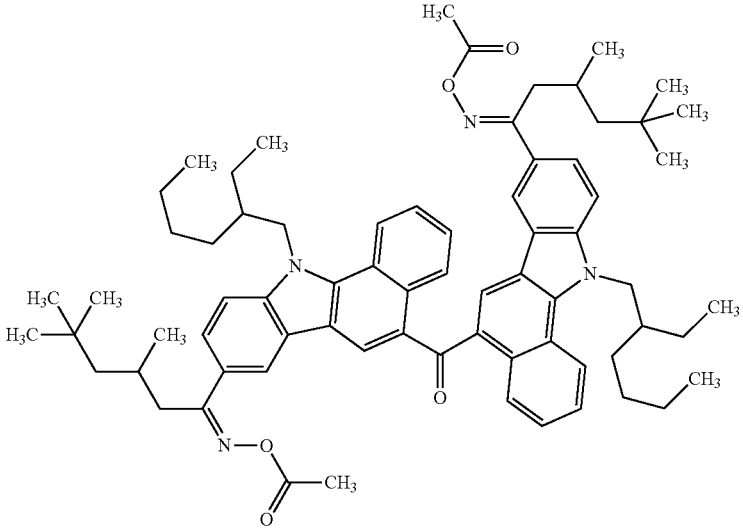 [SMILES: CCCCC(CC)Cn1c2ccc(/C(CC(C)CC(C)(C)C)=N\OC(C)=O)cc2c2cc(C(=O)c3cc4c5cc(/C(CC(C)CC(C)(C)C)=N/OC(C)=O)ccc5n(CC(CC)CCCC)c4c4ccccc34)c3ccccc3c21] | 0.58-0.74 (d), 0.75-1.00 (m), 1.81 (m), 2.19 (s), 2.30 (s), 2.82 (d), 4.78 (m), 7.56 (d), 7.76 (t), 7.84 (t), 7.89 (d), 8.23 (s), 8.68 (d), 8.83 (s), 9.87 (d) |
| 7 | 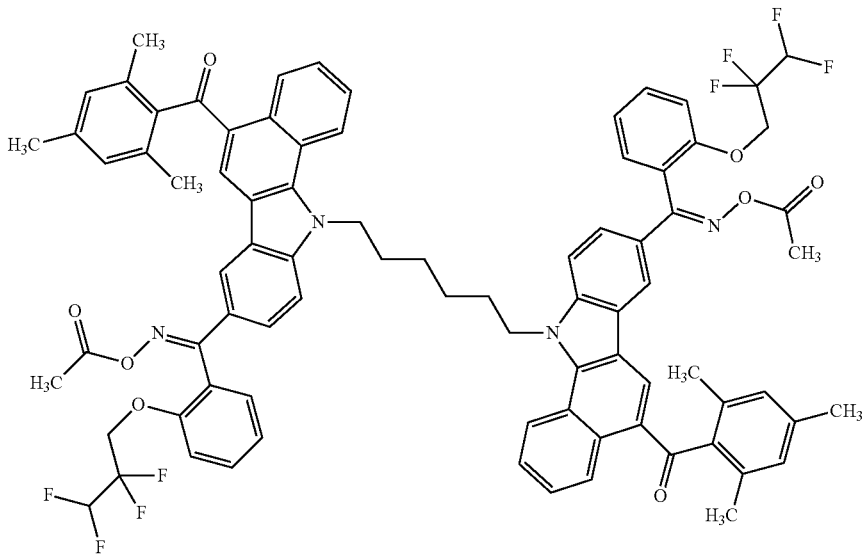 | — |

TABLE 1-continued
| Example | Structure | $^1$H-NMR spectrum (CDCl$_3$) δ [ppm] |
|---|---|---|
| 8 | 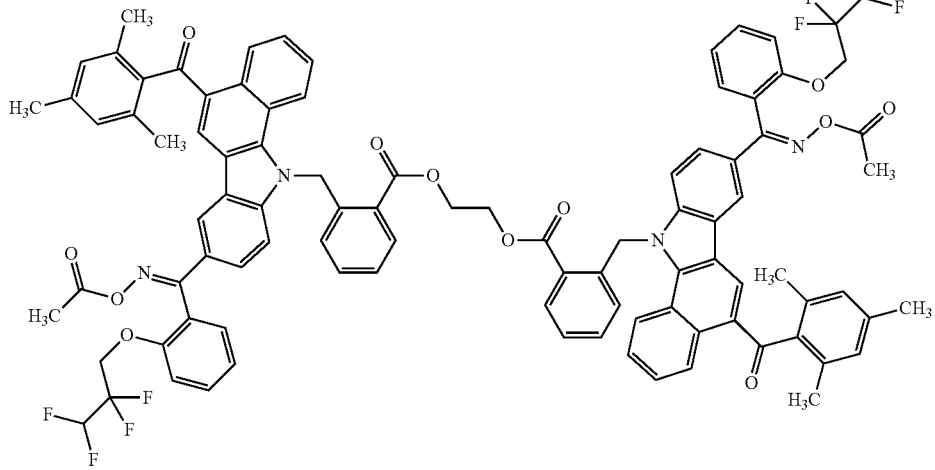 | — |
| 9 | 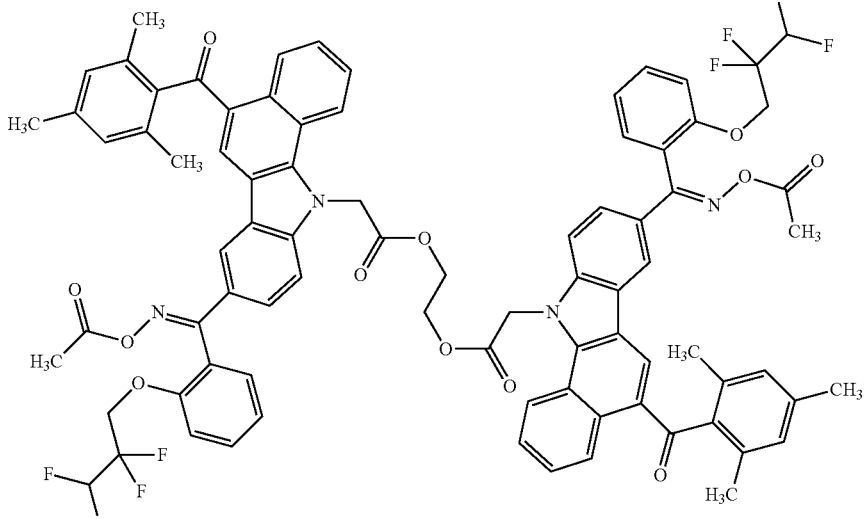 | — |

TABLE 1-continued
| Example | Structure | ¹H-NMR spectrum (CDCl₃) δ [ppm] |
|---|---|---|
| 10 | 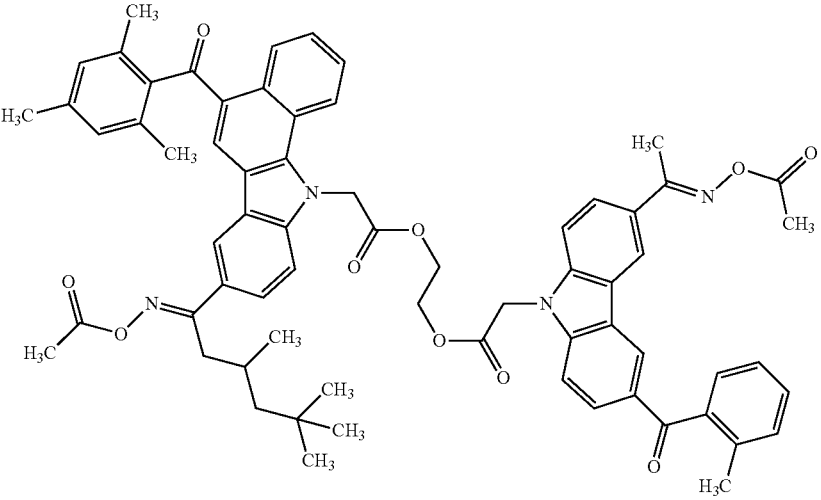 [SMILES: CC(=O)O/N=C(\C)c1ccc2c(c1)c1cc(C(=O)c3ccccc3C)ccc1n2CC(=O)OCCOC(=O)Cn1c2ccc(/C(CC(C)CC(C)(C)C)=N/OC(C)=O)cc2c2cc(C(=O)c3c(C)cc(C)cc3C)c3ccccc3c21] | 0.78-0.92 (m), 1.18-1.34 (m), 1.87 (m), 2.14 (s), 2.25 (s), 2.30 (s), 2.37 (s), 2.41 (s), 4.35 (m), 4.43 (m), 4.83 (w), 5.45 (s), 6.93 (s), 7.18-7.36 (m), 7.37-7.46 (m), 7.57 (t), 7.71 (t), 7.82 (t), 8.02 (d), 8.27 (d), 8.29 (s), 8.35 (s), 8.39 (s), 8.48 (s) |
| 11 | 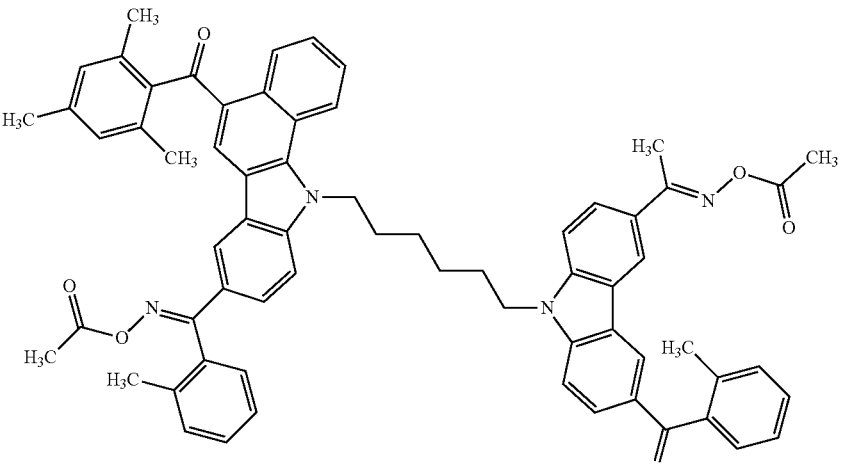 | — |

| Example | Structure | ¹H-NMR spectrum (CDCl₃) δ [ppm] |
|---|---|---|
| 12 | 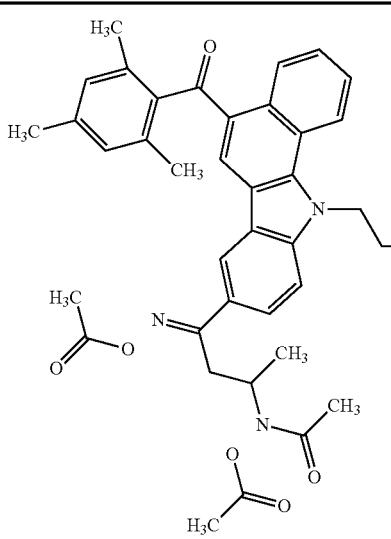 | 1.15 (d), 1.91 (s), 2.02 (s), 2.16 (s), 2.38 (s), 2.39 (s), 3.45 (m), 4.04 (m), 4.90 (m), 4.92 (m), 6.95 (s), 7.25-8.10 (m), 8.38 (m), 8.50 (m), 9.52 (m) |
| 13 | 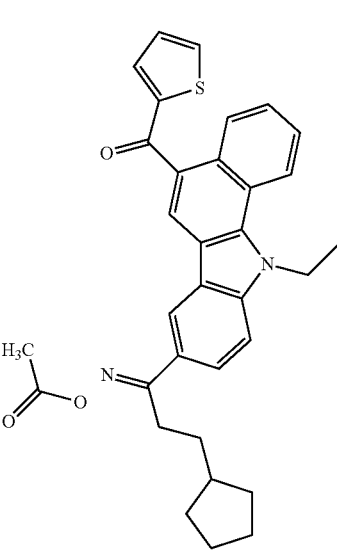 | 1.11 (m), 1.51 (m), 1.78 (m), 2.22 (s), 2.26 (s), 2.48 (t), 2.90 (t), 4.00 (t), 4.88 (t), 7.12 (t), 7.52-7.64 (m), 7.75 (d), 7.81 (d), 8.43 (s), 8.50 (s), 8.51 (d), 8.55 (d) |

TABLE 1-continued
| Example | Structure | $^1$H-NMR spectrum (CDCl$_3$) δ [ppm] |
|---|---|---|
| 14 | 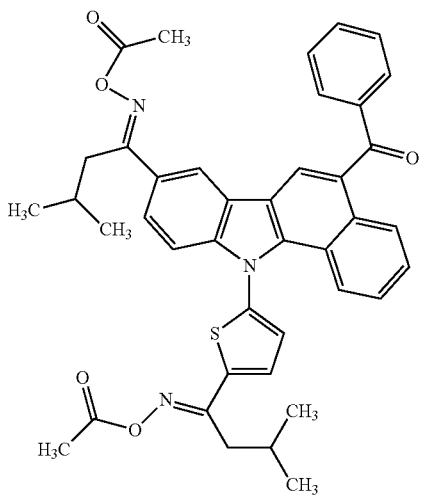 [SMILES: CC(=O)O/N=C(\CC(C)C)c1ccc2c(c1)c1cc(C(=O)c3ccccc3)c3ccccc3c1n2-c1ccc(/C(CC(C)C)=N/OC(C)=O)s1] | 0.95 (d), 1.12 (d), 1.96 (m), 2.22 (m), 2.26 (s), 2.84 (d), 2.86 (d), 7.29 (d), 7.34 (d), 7.40 (t), 7.51 (d), 7.53 (d), 7.60 (d), 7.67 (t), 7.78 (d), 7.80 (d), 7.95 (d), 8.35 (s), 8.39 (d), 8.42 (s) |
| 15 | 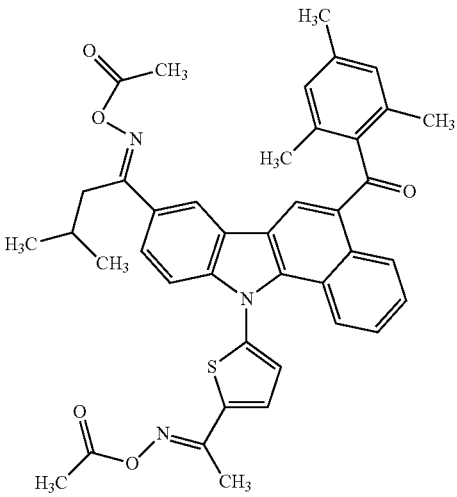 [SMILES: CC(=O)O/N=C(\CC(C)C)c1ccc2c(c1)c1cc(C(=O)c3c(C)cc(C)cc3C)c3ccccc3c1n2-c1ccc(/C(C)=N/OC(C)=O)s1] | — |
| 16 | 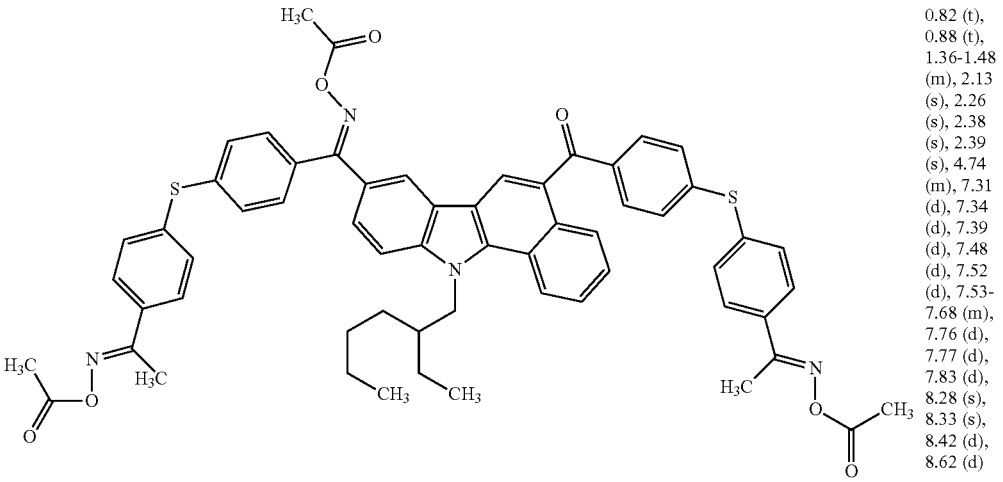 | 0.82 (t), 0.88 (t), 1.36-1.48 (m), 2.13 (s), 2.26 (s), 2.38 (s), 2.39 (s), 4.74 (m), 7.31 (d), 7.34 (d), 7.39 (d), 7.48 (d), 7.52 (d), 7.53-7.68 (m), 7.76 (d), 7.77 (d), 7.83 (d), 8.28 (s), 8.33 (s), 8.42 (d), 8.62 (d) |

TABLE 1-continued

| Example | Structure | $^1$H-NMR spectrum (CDCl$_3$) δ [ppm] |
|---|---|---|
| 17 | 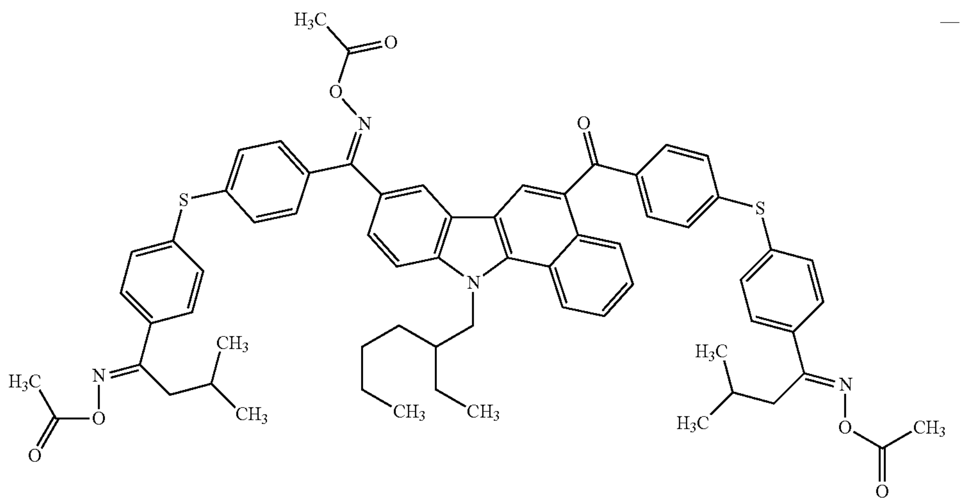 | — |
| 18 | 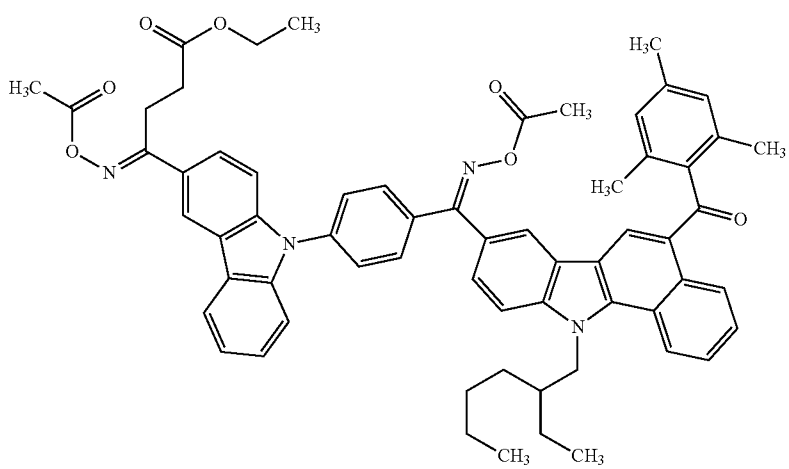 [SMILES: CCCCC(CC)Cn1c2ccc(/C(=N\OC(C)=O)c3ccc(-n4c5ccccc5c5cc(/C(CCC(=O)OCC)=N/OC(C)=O)ccc54)cc3)cc2c2cc(C(=O)c3c(C)cc(C)cc3C)c3ccccc3c21] | 0.79-1.00 (m), 1.18-1.56 (m), 2.04 (s), 2.20 (s), 2.29 (s), 2.31 (s), 2.33 (s), 2.36 (s), 2.64 (q), 3.30 (q), 4.12 (m), 4.78 (m), 6.92 (s), 6.94 (s), 7.34-7.42 (m), 7.44-7.58 (m), 7.66 (d), 7.67 (t), 7.70-7.86 (m), 7.88 (d), 8.09 (s), 8.18 (d), 8.22 (d), 8.34 (s), 8.40 (s), 8.52 (s), 8.53 (s), 8.56 (s), 8.65 (d), 8.68 (d), 9.53 (d), 9.55 (d) |

TABLE 1-continued

| Example | Structure | ¹H-NMR spectrum (CDCl₃) δ [ppm] |
|---|---|---|
| 19 | 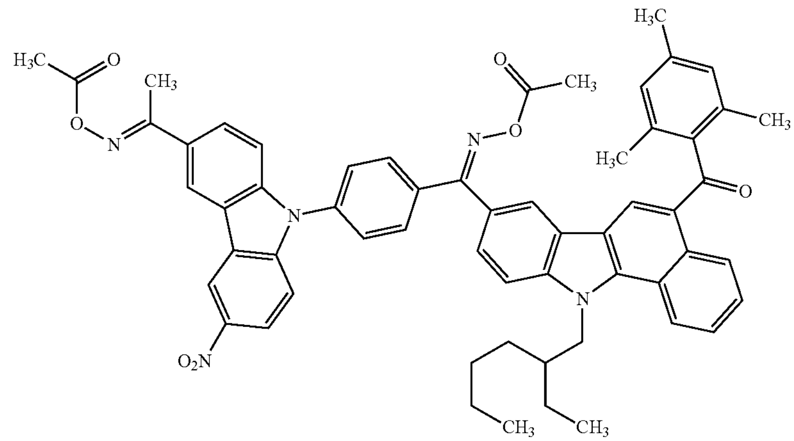 [SMILES: CCCCC(CC)Cn1c2ccc(/C(=N\OC(C)=O)c3ccc(-n4c5ccc(/C(C)=N/OC(C)=O)cc5c5cc([N+](=O)[O-])ccc54)cc3)cc2c2cc(C(=O)c3c(C)cc(C)cc3C)c3ccccc3c21] | — |
| 20 | 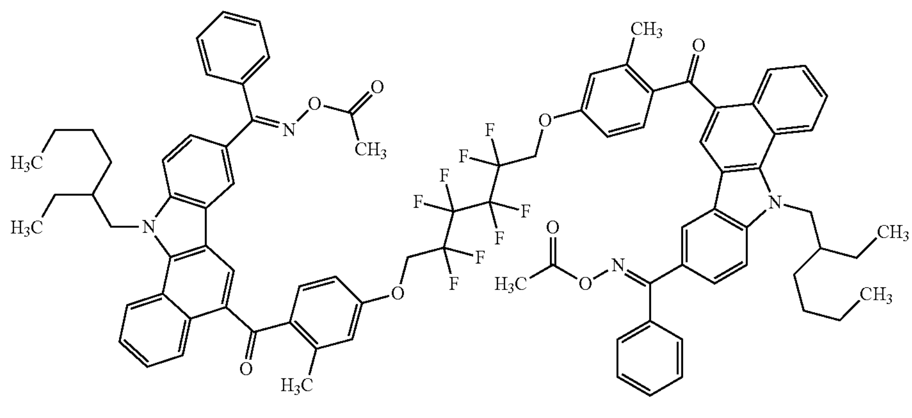 [SMILES: CCCCC(CC)Cn1c2ccc(/C(=N/OC(C)=O)c3ccccc3)cc2c2cc(C(=O)c3ccc(OCC(F)(F)C(F)(F)C(F)(F)C(F)(F)COc4ccc(C(=O)c5cc6c7cc(/C(=N/OC(C)=O)c8ccccc8)ccc7n(CC(CC)CCCC)c6c6ccccc56)c(C)c4)cc3C)c3ccccc3c21] | — |
| 21 | 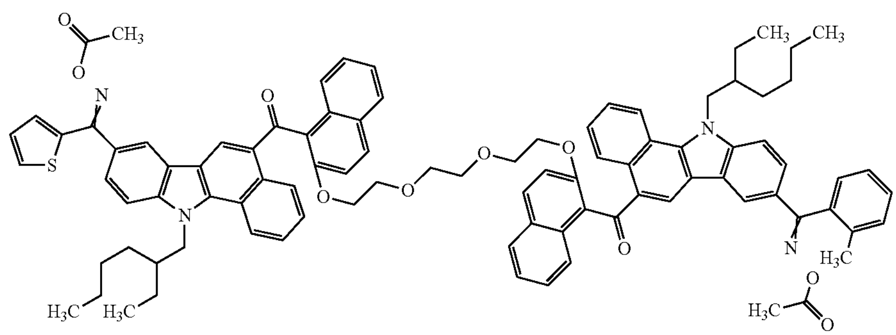 | 0.78-0.96 (m), 1.12-1.28 (m), 1.92 (s), 1.98 (s), 2.09 (s), 2.19 (s), 2.31 (s), 2.71 (s), 3.08 (m), 3.04 (m), 3.88 (m), 4.51-4.58 (m), 6.90-7.06 (m), 7.14-7.48 (m), 7.62-7.74 (m), 7.76-7.98 (m), 8.00 (s), 8.23 (s), 8.29 (d), 8.60 (d), 9.44 (d) |

APPLICATION EXAMPLES

Example A1

Preparation of poly(benzylmethacrylate-co-methacrylic acid)

24 g of benzylmethacrylate, 6 g of methacrylic acid and 0.525 g of azobisisobutyronitrile (AIBN) are dissolved in 90 ml of propylene glycol 1-monomethyl ether 2-acetate (PGMEA). The resulting reaction mixture is placed in a preheated oil bath at 80° C. After stirring for 5 hours at 80° C. under nitrogen, the resulting viscous solution is cooled to room temperature and used without further purification. The solid content is about 25%.

Example A2

Sensitivity Tests

A photocurable composition for a sensitivity test is prepared by mixing the following components:
200.0 parts by weight of copolymer of benzylmethacrylate and methacrylic acid (benzylmethacrylate:methacrylic acid=80:20 by weight) 25% propylene glycol 1-monomethyl ether 2-acetate (PGMEA) solution, prepared in above example A1
50.0 parts by weight of dipentaerythritol hexaacrylate ((DPHA), provided by UCBChemicals),
1.0 parts by weight of photoinitiator
150.0 parts by weight of PGMEA All operations are carried out under yellow light. The compositions are applied to an aluminum plate using an electric applicator with a wire wound bar. The solvent is removed by heating at 80° C. for 10 minutes in a convection oven. The thickness of the dry film is approximately 2 µm. A standardized test negative film with 21 steps of different optical density (Stouffer step wedge) is placed with an air gap of around 100 µm between the film and the resist. A glass filter (UV-35) is placed on the negative film. Exposure is carried out using a 250W super high pressure mercury lamp (USHIO, USH-250BY) at a distance of 15 cm. A total exposure dose measured by an optical power meter (ORC UV Light Measure Model UV-M02 with UV-35 detector) on the glass filter is 1000 mJ/cm$^2$. After exposure, the exposed film is developed with an alkaline solution (5% aqueous solution of DL-A4, Yokohama Yushi) for 120 sec. at 28° C. by using a spray type developer (AD-1200, Takizawa Sangyo). The sensitivity of the initiator used is characterized by indicating the highest number of the step remained (i.e. polymerized) after developing. The higher the number of steps, the more sensitive is the initiator tested. The results are listed in table 2.

TABLE 2

| photoinitiator of example | number of steps |
|---|---|
| 1 | 19 |
| 2 | 19 |
| 3 | 19 |

Example A3

Sensitivity Tests

A photocurable composition for a sensitivity test is prepared by mixing the following components:
11.0 parts by weight of REGAL® 400 pigment black (provided by CABOT)
11.0 parts by weight of EFKA® 4046, dispersant (provided by BASF)
10.3 parts by weight of Ripoxy® SPC1000, binder polymer (provided by SHOWA DENKO)
3.6 parts by weight of dipentaerythritol penta-/hexa-acrylate ((DPHA), provided by SIGMA-ALDRICH)
1.0 parts by weight of photoinitiator
48.5 parts by weight of propylene glycol monomethyl ether acetate (PGMEA)
15.6 parts by weight of cyclohexanone All operations are carried out under yellow light. The compositions are applied to a glass plate using spincoater. The solvent is removed by heating at 80° C. for 10 minutes in a convection oven. The thickness of the dry film is approximately 1.4 µm. A step-wedge pattern mask with 9 linear steps and 9 logarithmic steps of different optical density (Edumund Optics, EIA GrayScale Pattern Slide) is placed on the resist directly. Exposure is carried out using a 250 W super high pressure mercury lamp (USHIO, USH-250BY) at a distance of 15 cm. A total exposure dose measured by an optical power meter (ORC UV Light Measure Model UV-M02 with UV-35 detector) on the glass filter is 500 mJ/cm$^2$. After exposure, the exposed film is developed with an alkaline solution (5% aqueous solution of DL-A4, YOKOHAMA OILS & FATS) for 10 seconds after break time at 28° C. by using a spray type developer (AD-1200, MIKASA). Break time is the development time of unexposed region. The necessary UV dose for full curing (i.e. the pattern is not dissolved with the alkaline solution) is calculated from the residual thickness of each step after development. The smaller the value of the dose, the more sensitive is the tested initiator. The results are listed in Table 3.

TABLE 3

| photoinitiator of example | The necessary UV dose for UV full curing |
|---|---|
| 4 | 32 mJ/cm$^2$ |
| 5 | 23 mJ/cm$^2$ |
| 10 | 51 mJ/cm$^2$ |
| 13 | 59 mJ/cm$^2$ |
| 16 | 54 mJ/cm$^2$ |
| 18 | 41 mJ/cm$^2$ |
| 21 | 53 mJ/cm$^2$ |
| Irgacure ® OXE02 | 80 mJ/cm$^2$ |

Irgacure ®OXE 02 is ethanone, 1-[9-ethyl-6-(2-methyl-benzoyl)-9H-carbazol-3-yl]-1-(O-acetyloxime)

The invention claimed is:

1. A compound of formula (I):

$$\text{(I)}$$

[Chemical structure showing a carbazole-like fused ring system with substituents $R_1$, $R_2$, $R_3$, $R_4$, $R_5$, $R_6$, $R_7$, $R_8$, $R_9$, $R_{10}$ on the ring carbons and $R_{11}$ on nitrogen]

wherein:

$R_1, R_2, R_3, R_4, R_5, R_6, R_7, R_8, R_9$ and $R_{10}$ independently of each other are hydrogen, $C_1$-$C_{20}$alkyl,

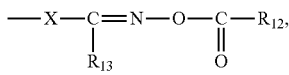

$COR_{14}$, $NO_2$, or $OR_{15}$, provided that at least one of $R_1, R_2, R_3, R_4, R_5, R_6, R_7, R_8, R_9$, and $R_{10}$ is

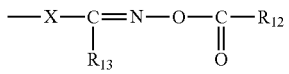

and provided that at least one of the remaining $R_1, R_2, R_3, R_4, R_5, R_6, R_7, R_8, R_9$, and $R_{10}$ is $COR_{14}$ or $NO_2$;

X is CO or a direct bond;

$R_{11}$ is $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$, $PO(OC_kH_{2k+1})_2$, or M, or $R_{11}$ is $C_2$-$C_{20}$alkyl which is interrupted by one or more O, CO, S, C(O)O, OC(O), phenylene, naphthylene or $NR_{19}$, wherein the interrupted $C_2$-$C_{20}$alkyl is unsubstituted or substituted by one or more halogen, $OR_{15}$, $SR_{16}$, $COOR_{15}$, $CONR_{17}R_{18}$, $NR_{17}R_{18}$ or M;

or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, M,

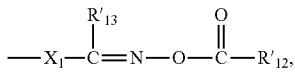

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

$R_{12}$ is hydrogen, $C_3$-$C_8$cycloalkyl, $C_2$-$C_5$alkenyl, $C_1$-$C_{20}$alkoxy or $C_1$-$C_{20}$alkyl which is unsubstituted or substituted by one or more halogen, phenyl, $C_1$-$C_{20}$alkylphenyl or CN, or $R_{12}$ is phenyl or naphthyl, each of which is unsubstituted or substituted by one or more $C_1$-$C_6$alkyl, $C_1$-$C_4$haloalkyl, halogen, CN, $OR_{15}$, $SR_{16}$, or $NR_{17}R_{18}$, or $R_{12}$ is $C_3$-$C_{20}$heteroaryl, benzyloxy or phenoxy, each of which is unsubstituted or substituted by one or more $C_1$-$C_6$alkyl, $C_1$-$C_4$haloalkyl and/or halogen;

$R_{13}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, $PO(OC_kH_{2k+1})_2$, SO—$C_1$-$C_{10}$alkyl, $SO_2$—$C_1$-$C_{10}$alkyl, M, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$, $NR_{17}R_{18}$ or by M, or $R_{13}$ is $C_1$-$C_{20}$alkyl which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $NR_{17}R_{18}$, $COOR_{15}$, $CONR_{17}R_{18}$, $PO(OC_kH_{2k+1})_2$,

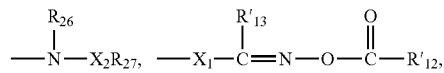

phenyl or by M, or $R_{13}$ is $C_1$-$C_{20}$alkyl which is substituted by phenyl which is substituted by one or more halogen, $C_1$-$C_{20}$alkyl, $C_1$-$C_4$haloalkyl, $OR_{15}$, $SR_{16}$ or by $NR_{17}R_{18}$, or $R_{13}$ is $C_2$-$C_{20}$alkyl which is interrupted by one or more O, CO, S, C(O)O, OC(O), phenylene, naphthylene, or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, M, or by phenyl which is substituted by $OR_{15}$, $SR_{16}$ or $NR_{17}R_{18}$, or $R_{13}$ is CN, $CONR_{17}R_{18}$, $NO_2$, $C_1$-$C_4$haloalkyl, $S(O)_m$—$C_1$-$C_6$alkyl; $S(O)_m$-phenyl which is unsubstituted or substituted by $C_1$-$C_{12}$alkyl or $SO_2$—$C_1$-$C_6$alkyl, or $R_{13}$ is $SO_2O$-phenyl which is unsubstituted or substituted by $C_1$-$C_{12}$alkyl; or is diphenyl phosphinoyl or di-($C_1$-$C_4$alkoxy)-phosphinoyl;

M is

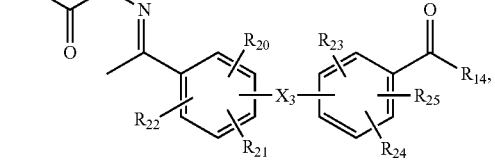

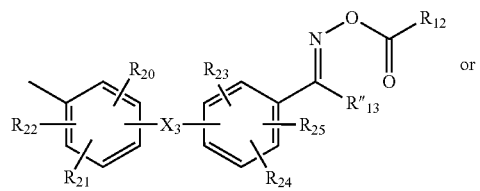

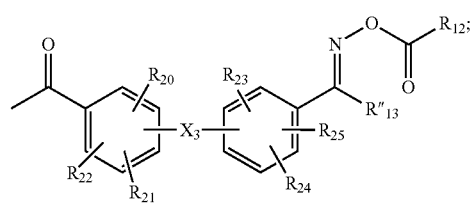

k is an integer 1-10;

m is 1 or 2;

$R'_{12}$ has one of the meanings as given for $R_{12}$;

$R'_{13}$ has one of the meanings as given for $R_{13}$;

$R''_{13}$ is $C_1$-$C_{20}$alkyl which is unsubstituted or substituted by phenyl or by phenyl which is substituted by halogen, $C_1$-$C_{20}$alkyl, $C_1$-$C_4$haloalkyl, $OR_{15}$, $SR_{16}$ or by $NR_{17}R_{18}$, or R"$_{13}$ is C$_2$-C$_{20}$alkyl which is interrupted by one or more O, CO, S, C(O)O, OC(O), phenylene, naphthylene or NR$_{19}$, wherein the interrupted C$_2$-C$_{20}$alkyl is unsubstituted or substituted by one or more halogen, OR$_{15}$, COOR$_{15}$, CONR$_{17}$R$_{18}$, phenyl, or by phenyl which is substituted by OR$_{15}$, SR$_{16}$ or NR$_{17}$R$_{18}$, or R"$_{13}$ is CN, CONR$_{17}$R$_{18}$, NO$_2$, C$_1$-C$_4$haloalkyl, S(O)$_m$—C$_1$-C$_6$alkyl; S(O)$_m$-phenyl which is unsubstituted or substituted by C$_1$-C$_{12}$alkyl or SO$_2$—C$_1$-C$_6$alkyl, or R"$_{13}$ is SO$_2$O-phenyl which is unsubstituted or substituted by C$_1$-C$_{12}$alkyl; or is diphenyl phosphinoyl or di-(C$_1$-C$_4$alkoxy)-phosphinoyl, or R"$_{13}$ is C$_6$-C$_{20}$aryl or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, PO(OC$_k$H$_{2k+1}$)$_2$, SO—C$_1$-C$_{10}$alkyl, SO$_2$—C$_1$-C$_{10}$alkyl, or by C$_2$-C$_{20}$alkyl which is interrupted by one or more O, CO, S, C(O)O, OC(O), phenylene, naphthylene or by NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or by NR$_{17}$R$_{18}$;

X$_1$ is O, CO, S or a direct bond;
X$_2$ is O, S, SO or SO$_2$;
X$_3$ is O, S or NR$_{19}$;
R$_{14}$ is C$_6$-C$_{20}$aryl or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, or by C$_2$-C$_{20}$alkyl which is interrupted by one or more O, S, or NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or NR$_{17}$R$_{18}$, or R$_{14}$ is

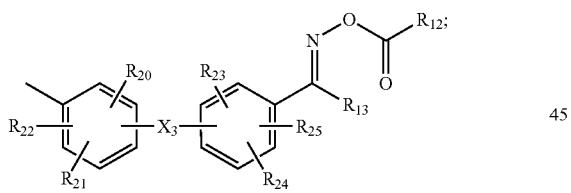

R$_{15}$ is hydrogen, phenyl-C$_1$-C$_3$alkyl, C$_1$-C$_{20}$alkyl which is unsubstituted or substituted by one or more halogen, OH, SH, CN, C$_3$-C$_6$alkenoxy, OCH$_2$CH$_2$CN, OCH$_2$CH$_2$(CO)O(C$_1$-C$_4$alkyl), O(CO)—(C$_1$-C$_4$alkyl), O(CO)—(C$_2$-C$_4$)alkenyl, O(CO)-phenyl, (CO)OH, (CO)O(C$_1$-C$_4$alkyl), C$_3$-C$_{20}$cycloalkyl, SO$_2$—(C$_1$-C$_4$haloalkyl), O(C$_1$-C$_4$haloalkyl), O(C$_1$-C$_{20}$arylene)-M, or by C$_3$-C$_{20}$cycloalkyl which is interrupted by one or more O, or R$_{15}$ is C$_2$-C$_{20}$alkyl which is interrupted by one or more O, S or NR$_{19}$, which interrupted C$_2$-C$_{20}$alkyl is unsubstituted or substituted by O—C$_6$-C$_{20}$arylene-M, or R$_{15}$ is (CH$_2$CH$_2$O)$_{n+1}$H, (CH$_2$CH$_2$O)$_n$(CO)—(C$_1$-C$_8$alkyl), C$_1$-C$_8$alkanoyl, C$_2$-C$_{12}$alkenyl, C$_3$-C$_6$alkenoyl or C$_3$-C$_{20}$cycloalkyl which is uninterrupted or interrupted by one or more O, S, CO or NR$_{19}$, or R$_{15}$ is C$_1$-C$_8$alkyl-C$_3$-C$_{10}$cycloalkyl which is uninterrupted or interrupted by one or more O, or R$_{15}$ is benzoyl which is unsubstituted or substituted by one or more C$_1$-C$_6$alkyl, halogen, OH or C$_1$-C$_3$alkoxy, or R$_{15}$ is phenyl, naphthyl or C$_3$-C$_{20}$heteroaryl, each of which is unsubstituted or substituted by one or more halogen, OH, C$_1$-C$_{12}$alkyl, C$_1$-C$_{12}$alkoxy, CN, NO$_2$, phenyl-C$_1$-C$_3$alkyloxy, phenoxy, C$_1$-C$_{12}$alkylsulfanyl, phenylsulfanyl, N(C$_1$-C$_{12}$alkyl)$_2$, diphenylamino or

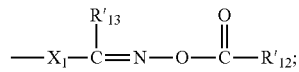

n is 1-20;

R$_{16}$ is hydrogen, C$_2$-C$_{12}$alkenyl, C$_3$-C$_{20}$cycloalkyl, or phenyl-C$_1$-C$_3$alkyl, wherein the C$_2$-C$_{12}$alkenyl, C$_3$-C$_{20}$cycloalkyl, or phenyl-C$_1$-C$_3$alkyl is uninterrupted or interrupted by one or more O, S, CO, NR$_{19}$, or R$_{16}$ is C$_1$-C$_{20}$alkyl which is unsubstituted or is substituted by one or more OH, SH, CN, C$_3$-C$_6$alkenoxy, OCH$_2$CH$_2$CN, OCH$_2$CH$_2$(CO)O(C$_1$-C$_4$alkyl), O(CO)—(C$_2$-C$_4$)alkenyl, O(CO)—(C$_1$-C$_4$alkyl), O(CO)-phenyl or COOR$_{15}$ or S—C$_6$-C$_{20}$arylene-S-M, or R$_{16}$ is C$_2$-C$_{20}$alkyl which is interrupted by one or more O, S, CO, NR$_{19}$, which interrupted C$_2$-C$_{20}$alkyl is unsubstituted or substituted by S—C$_6$-C$_{20}$arylene-M, or R$_{16}$ is (CH$_2$CH$_2$O)$_n$H, (CH$_2$CH$_2$O)$_n$(CO)—(C$_1$-C$_8$alkyl), C$_2$-C$_8$alkanoyl or C$_3$-C$_6$alkenoyl, or R$_{16}$ is benzoyl which is unsubstituted or substituted by one or more C$_1$-C$_6$alkyl, halogen, OH, C$_1$-C$_4$alkoxy or C$_1$-C$_4$alkylsulfanyl, or R$_{16}$ is phenyl, naphthyl or C$_3$-C$_{20}$heteroaryl, each of which is unsubstituted or substituted by one or more halogen, C$_1$-C$_{12}$alkyl, C$_1$-C$_4$haloalkyl, C$_1$-C$_{12}$alkoxy, CN, NO$_2$, phenyl-C$_1$-C$_3$alkyloxy, phenoxy, C$_1$-C$_{12}$alkylsulfanyl, phenylsulfanyl, N(C$_1$-C$_{12}$alkyl)$_2$, diphenylamino, (CO)O(C$_1$-C$_8$alkyl), (CO)—C$_1$-C$_8$alkyl, (CO)N(C$_1$-C$_8$alkyl)$_2$ or

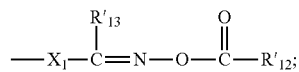

R$_{17}$ and R$_{18}$ independently of each other are hydrogen, C$_1$-C$_{20}$alkyl, C$_2$-C$_4$hydroxyalkyl, C$_2$-C$_{10}$alkoxyalkyl, C$_2$-C$_5$alkenyl, C$_3$-C$_{20}$cycloalkyl, phenyl-C$_1$-C$_3$alkyl, C$_1$-C$_8$alkanoyl, C$_1$-C$_8$alkanoyloxy, C$_3$-C$_{12}$alkenoyl, SO$_2$—(C$_1$-C$_4$haloalkyl) or benzoyl, or R$_{17}$ and R$_{18}$ are phenyl, naphthyl or C$_3$-C$_{20}$heteroaryl, each of which is unsubstituted or substituted by one or more halogen, C$_1$-C$_4$haloalkyl, C$_1$-C$_{20}$alkoxy, C$_1$-C$_{12}$alkyl, benzoyl or C$_1$-C$_{12}$alkoxy, or R$_{17}$ and R$_{18}$ together with the N-atom to which they are attached form a 5- or 6-membered saturated or unsaturated ring which is uninterrupted or is interrupted by O, S or NR$_{19}$, and which 5- or 6-membered saturated or unsaturated ring is unsubstituted or substituted by one or more C$_1$-C$_{20}$alkyl, C$_1$-C$_{20}$alkoxy, =O, OR$_{15}$, SR$_{16}$, NR$_{28}$R$_{29}$, COR$_{30}$, NO$_2$, halogen, C$_1$-C$_4$-haloalkyl, CN, phenyl,

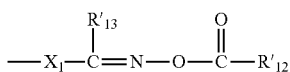

or by $C_3$-$C_{20}$cycloalkyl which is uninterrupted or is interrupted by one or more O, S, CO or $NR_{19}$, or $R_{17}$ and $R_{18}$ together with the N-atom to which they are attached form a group

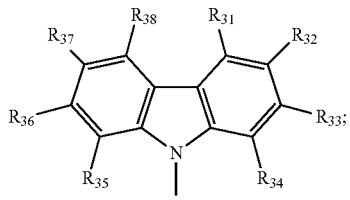

$R_{19}$ is hydrogen, $C_1$-$C_{20}$alkyl, $C_1$-$C_4$haloalkyl, $C_2$-$C_{20}$alkyl which is interrupted by one or more O, CO, C(O)O, or OC(CO), or is phenyl-$C_1$-$C_4$alkyl, $C_3$-$C_8$cycloalkyl which is uninterrupted or is interrupted by one or more O or CO, or $R_{19}$ is $COR_{30}$, or $R_{19}$ is phenyl or naphthyl both of which are unsubstituted or substituted by one or more $C_1$-$C_{20}$alkyl, halogen, $C_1$-$C_4$haloalkyl, $OR_{15}$, $SR_{16}$, $NR_{17}R_{18}$, $COR_{14}$, or

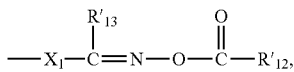

or $R_{19}$ is $C_1$-$C_6$alkylene or $C_2$-$C_6$alkenylene linked to the phenyl or naphthyl ring of the carbazole moiety and forming a 5- or 6-membered saturated or unsaturated ring;

$R_{20}$, $R_{21}$, $R_{22}$, $R_{23}$, $R_{24}$ or $R_{25}$ independently of each other are hydrogen, $COR_{14}$, $NO_2$,

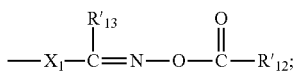

or one of $R_{21}$ and $R_{22}$, or $R_{24}$ and $R_{25}$ is

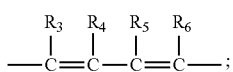

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system which is unsubstituted or substituted by one or more $C_1$-$C_{20}$alkyl, $C_1$-$C_4$haloalkyl, $C_1$-$C_{20}$alkoxy, =O, $OR_{15}$, $SR_{16}$, $NR_{17}R_{18}$, $COR_{14}$,

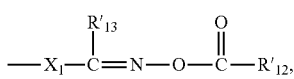

halogen, $NO_2$, CN, phenyl or by $C_3$-$C_{20}$cycloalkyl which is uninterrupted or is interrupted by one or more O, S, CO or $NR_{19}$;

$R_{26}$ is $COOR_{15}$, $CONR_{17}R_{18}$, $(CO)R_{15}$; or $R_{26}$ has one of the meanings given for $R_{17}$ and $R_{18}$;

$R_{27}$ is $COOR_{15}$, $CONR_{17}R_{18}$, $(CO)R_{15}$; or $R_{27}$ has one of the meanings given for $R_{15}$;

$R_{28}$ and $R_{29}$ independently of each other are hydrogen, $C_1$-$C_{20}$alkyl, $C_1$-$C_4$haloalkyl, $C_3$-$C_{10}$cycloalkyl or phenyl, or $R_{28}$ and $R_{29}$ together with N-atom to which they are attached form a 5- or 6-membered saturated or unsaturated ring, which is uninterrupted or interrupted by O, S or $NR_{19}$, and which 5- or 6-membered saturated or unsaturated ring is not condensed or to which 5- or 6-membered saturated or unsaturated ring a benzene ring is condensed;

$R_{30}$ is hydrogen, OH, $C_1$-$C_{20}$alkyl, $C_1$-$C_4$haloalkyl, $C_2$-$C_{20}$alkyl which is interrupted by one or more O, CO or by $NR_{19}$, or is $C_3$-$C_{20}$cycloalkyl which is uninterrupted or is interrupted by O, S, CO or $NR_{19}$, or $R_{30}$ is phenyl, naphthyl, phenyl-$C_1$-$C_4$alkyl, $OR_{15}$, $SR_{16}$ or $NR_{17}R_{18}$;

$R_{31}$, $R_{32}$, $R_{33}$, $R_{34}$, $R_{35}$, $R_{36}$, $R_{37}$ and $R_{38}$ independently of each other are hydrogen,

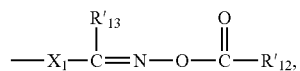

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl which is uninterrupted or is interrupted by one or more O, S, CO or $NR_{19}$;

or $R_{33}$ and $R_{34}$ or $R_{35}$ and $R_{36}$ or both, $R_{33}$ and $R_{34}$ and $R_{35}$ and $R_{36}$ are

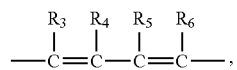

provided that at least two oxime ester groups selected from the group consisting of

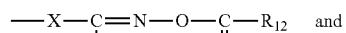
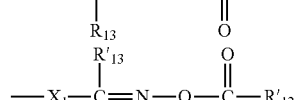

are present in the molecule.

2. The compound of claim 1, wherein:

$R_1$, $R_2$, $R_3$, $R_4$, $R_5$, $R_6$, $R_7$, $R_8$, $R_9$, and $R_{10}$ independently of each other are hydrogen, $C_1$-$C_{20}$alkyl,

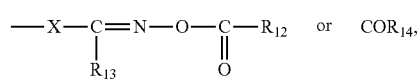

provided that at least one of $R_1$, $R_2$, $R_3$, $R_4$, $R_5$, $R_6$, $R_7$, $R_8$, $R_9$ and $R_{10}$ is

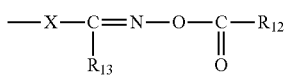

and provided that at least one of the remaining $R_1$, $R_2$, $R_3$, $R_4$, $R_5$, $R_6$, $R_7$, $R_8$, $R_9$, and $R_{10}$ is $COR_{14}$;

X is CO or a direct bond;

$R_{11}$ is $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$, $PO(OC_kH_{2k+1})_2$, or M, or $R_{11}$ is $C_2$-$C_{20}$alkyl which is interrupted by one or more O, CO, S, C(O)O, OC(O), phenylene, naphthylene or $NR_{19}$, wherein the interrupted $C_1$-$C_{20}$alkyl is unsubstituted or substituted by one or more halogen, $OR_{15}$, $SR_{16}$, $COOR_{15}$, $CONR_{17}R_{18}$, $NR_{17}R_{18}$, or M, or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, M,

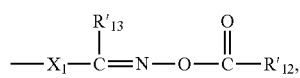

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

$R_{12}$ is $C_1$-$C_{20}$alkyl, phenyl, or $C_1$-$C_8$alkoxy;

$R_{13}$ is phenyl, naphthyl, or $C_3$-$C_{20}$heteroaryl each of which is unsubstituted or substituted by one or more phenyl, halogen, $C_1$-$C_4$haloalkyl, $OR_{15}$, $SR_{16}$, $NR_{17}R_{18}$, M, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_4$-$C_{20}$heteroaryl, $C_6$-$C_{20}$aryloxycarbonyl, $C_4$-$C_{20}$heteroaryloxycarbonyl, $OR_{15}$, $SR_{16}$, $NR_{17}R_{18}$ or by M, or $R_{13}$ is $C_1$-$C_{20}$alkyl which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$ heteroaryloxycarbonyl, $NR_{17}R_{18}$, $COOR_{15}$, $CONR_{17}R_{18}$, $PO(OC_kH_{2k+1})_2$, phenyl or by M, or $R_{13}$ is $C_1$-$C_{20}$alkyl which is substituted by phenyl which is substituted by halogen, $C_1$-$C_{20}$alkyl, $C_1$-$C_4$haloalkyl, $OR_{15}$, $SR_{16}$ or by $NR_{17}R_{18}$, or $R_{13}$ is $C_2$-$C_{20}$alkyl which is interrupted by one or more O, CO, S, C(O)O, OC(O), phenylene, naphthylene, or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, M, or by phenyl which is substituted by $OR_{15}$, $SR_{16}$ or $NR_{17}R_{18}$;

M is

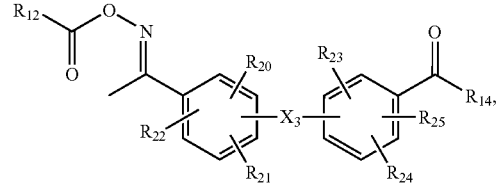

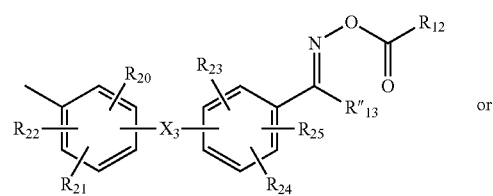

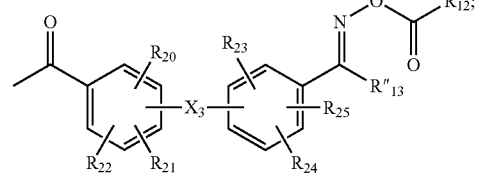

k is an integer 1-10;

m is 1 or 2;

$R'_{12}$ has one of the meanings as given for $R_{12}$;

$R'_{13}$ has one of the meanings as given for $R_{13}$;

$R''_{13}$ is $C_1$-$C_{20}$alkyl which is unsubstituted or substituted by phenyl or by phenyl which is substituted by halogen, $C_1$-$C_{20}$alkyl, $C_1$-$C_4$haloalkyl, $OR_{15}$, $SR_{16}$ or by $NR_{17}R_{18}$, or $R''_{13}$ is $C_2$-$C_{20}$alkyl which is interrupted by one or more O, CO, S, C(O)O, OC(O), phenylene, naphthylene or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, or by phenyl which is substituted by $OR_{15}$, $SR_{16}$ or $NR_{17}R_{18}$, or $R''_{13}$ is CN, $CONR_{17}R_{18}$, $NO_2$ or $C_1$-$C_4$haloalkyl;

or $R''_{13}$ is $C_6$-$C_{20}$aryl, each of which is unsubstituted or substituted by one or more $OR_{15}$, $SR_{16}$, $NR_{17}R_{18}$, or each of which is substituted by one or more $C_1$-$C_{20}$alkyl;

$X_1$ is O, CO, S or a direct bond;

$X_3$ is O, S or $NR_{19}$;

$R_{14}$ is phenyl, naphthyl, or $C_3$-$C_{20}$heteroaryl each of which is unsubstituted or substituted by one or more $OR_{15}$, $SR_{16}$, $NR_{17}R_{18}$, M or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{19}R_{20}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

or $R_{14}$ is

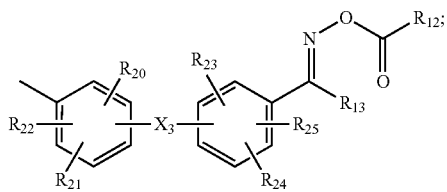

$R_{15}$ is hydrogen, phenyl-$C_1$-$C_3$alkyl, $C_1$-$C_{20}$alkyl which is unsubstituted or substituted by one or more halogen, $OCH_2CH_2CN$, $OCH_2CH_2(CO)O(C_1$-$C_4$alkyl), $O(CO)$—$(C_1$-$C_4$alkyl), $O(CO)$—$(C_2$-$C_4)$alkenyl, $O(CO)$-phenyl, $(CO)OH$, $(CO)O(C_1$-$C_4$alkyl), $C_3$-$C_{20}$cycloalkyl, $SO_2$—$(C_1$-$C_4$haloalkyl), $O(C_1$-$C_4$haloalkyl), $O(C_1$-$C_{20}$arylene)-M, or by $C_3$-$C_{20}$cycloalkyl which is interrupted by one or more O, or $R_{15}$ is $C_2$-$C_{20}$alkyl which is interrupted by one or more O, S or $NR_{19}$;

$R_{16}$ is methyl substituted by $COOR_{15}$, or $R_{16}$ is phenyl unsubstituted or substituted by one or more $C_1$-$C_{12}$alkyl, $C_1$-$C_{12}$alkoxy, or

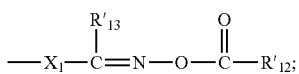

$R_{17}$ and $R_{18}$ independently of each other are hydrogen, phenyl, $C_1$-$C_{20}$alkyl, $C_1$-$C_8$alkanoyl, $C_1$-$C_8$alkanoyloxy, or $R_{17}$ and $R_{18}$ together with the N-atom to which they are attached form a heteroaromatic ring system which is uninterrupted or is interrupted by

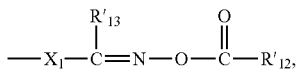

or $R_{17}$ and $R_{18}$ together with the N-atom to which they are attached form a group

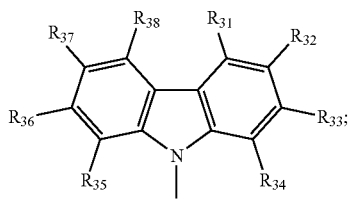

$R_{19}$ is hydrogen, $C_1$-$C_{20}$alkyl, or $C_2$-$C_{20}$alkyl which is interrupted by one or more O or CO, or $R_{19}$ is phenyl or naphthyl both of which are unsubstituted or substituted by one or more $C_1$-$C_{20}$alkyl, halogen, $C_1$-$C_4$haloalkyl, $OR_{15}$, $SR_{16}$, $NR_{17}R_{18}$, $COR_{14}$, or

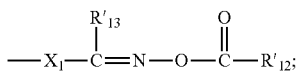

$R_{20}$, $R_{21}$, $R_{22}$, $R_{23}$, $R_{24}$, or $R_{25}$ independently of each other is hydrogen, $COR_{14}$, $NO_2$,

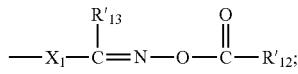

or one of $R_{21}$ and $R_{22}$ or $R_{24}$ and $R_{25}$ is

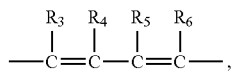

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system which is unsubstituted or substituted by one or more $C_1$-$C_{20}$alkyl, $C_1$-$C_{20}$alkoxy, $OR_{15}$, $SR_{16}$, $NR_{17}R_{18}$, $COR_{14}$,

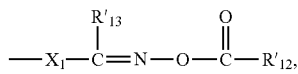

$NO_2$, phenyl;

$R_{31}$, $R_{32}$, $R_{33}$, $R_{34}$, $R_{35}$, $R_{36}$, $R_{37}$ and $R_{38}$ independently of each other are hydrogen,

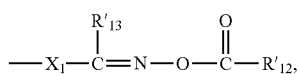

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl which is uninterrupted or is interrupted by one or more O, S, CO or $NR_{19}$, or $R_{33}$ and $R_{34}$ or $R_{35}$ and $R_{36}$ or both, $R_{33}$ and $R_{34}$ and $R_{35}$ and $R_{36}$ are

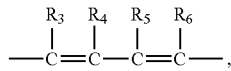

provided that at least two oxime ester groups are present in the molecule.

3. The compound of claim 1, wherein:

$R_1$, $R_2$, $R_3$, $R_4$, $R_5$, $R_6$, $R_7$, $R_8$, $R_9$ and $R_{10}$ independently of each other are hydrogen,

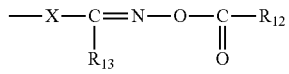

or $COR_{14}$, provided that at least one of $R_1$, $R_2$, $R_3$, $R_4$, $R_5$, $R_6$, $R_7$, $R_8$, $R_9$, and $R_{10}$ is

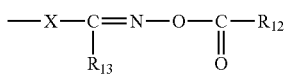

and provided that at least one of the remaining $R_1$, $R_2$, $R_3$, $R_4$, $R_5$, $R_6$, $R_7$, $R_8$, $R_9$, and $R_{10}$ is $COR_{14}$;

X is a direct bond;

$R_{11}$ is $C_1$-$C_{20}$alkyl which is unsubstituted or substituted by $NR_{17}R_{18}$, or $R_{11}$ is $C_2$-$C_{20}$alkyl which is interrupted by one or more C(O)O, OC(O) or phenylene, wherein the interrupted $C_1$-$C_{20}$alkyl is unsubstituted or substituted by $NR_{17}R_{18}$, or $R_{11}$ is phenyl or thienyl each of which is unsubstituted or substituted by

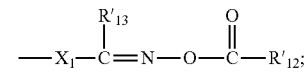

$R_{12}$ is $C_1$-$C_{20}$alkyl;

$R_{13}$ is phenyl or thienyl each of which is unsubstituted or substituted by one or more $OR_{15}$, $SR_{16}$, $NR_{17}R_{18}$, or is substituted by one or more $C_1$-$C_{20}$alkyl, or $R_{13}$ is $C_1$-$C_{20}$alkyl which is unsubstituted or substituted by $C_3$-$C_8$cycloalkyl, $COOR_{15}$

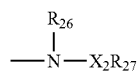

or by M;

M is

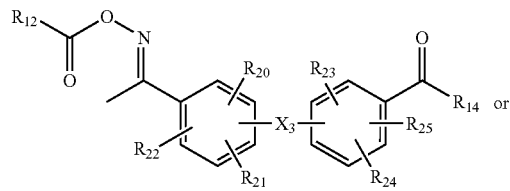

(X)

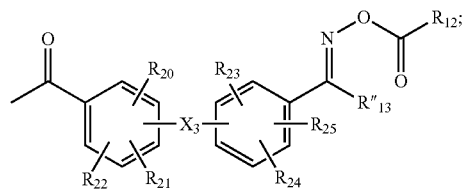

(Z)

$R'_{12}$ has one of the meanings as given for $R_{12}$;

$R'_{13}$ has one of the meanings as given for $R_{13}$;

$R''_{13}$ is $C_1$-$C_{20}$alkyl, phenyl or thienyl, wherein the phenyl or thienyl is unsubstituted or substituted by $C_1$-$C_{20}$alkyl;

$X_1$ is a direct bond;

$X_2$ is O;

$X_3$ is $NR_{19}$;

$R_{14}$ is phenyl or thienyl each of which is unsubstituted or substituted by one or more $OR_{15}$, $SR_{16}$, $NR_{17}R_{18}$ or $C_1$-$C_{20}$alkyl, or $R_{14}$ is

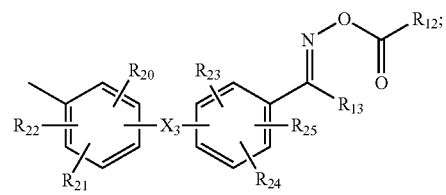

$R_{15}$ is $C_1$-$C_{20}$alkyl which is unsubstituted or substituted by one or more halogen or $O(C_1$-$C_{20}$arylene)-M, or $R_{15}$ is $C_2$-$C_{20}$alkyl which is interrupted by one or more O, which interrupted $C_2$-$C_{20}$alkyl is unsubstituted or substituted by O—$C_6$-$C_{20}$arylene-M;

$R_{16}$ is phenyl substituted by

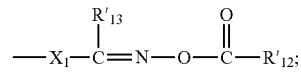

$R_{17}$ and $R_{18}$ together with the N-atom to which they are attached form a group

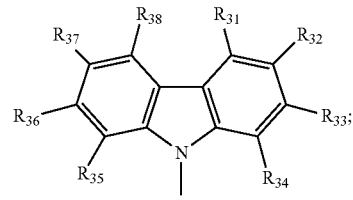

$R_{19}$ is $C_1$-$C_{20}$alkyl;

$R_{20}$, $R_{21}$, $R_{22}$, $R_{23}$, $R_{24}$, or $R_{25}$ independently of each other is hydrogen; or one of $R_{21}$ and $R_{22}$ or $R_{24}$ and $R_{25}$ is

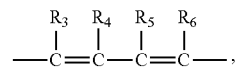

or $R_{20}$ and $R_{23}$ together with $X_3$ and the phenyl rings to which they are attached form a heteroaromatic ring system;

$R_{26}$ is $COOR_{15}$;

$R_{27}$ is $COOR_{15}$;

$R_{31}$, $R_{32}$, $R_{33}$, $R_{34}$, $R_{35}$, $R_{36}$, $R_{37}$ and $R_{38}$ independently of each other are hydrogen,

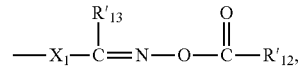

$NO_2$ or $COR_M$, or $R_{33}$ and $R_{34}$ are

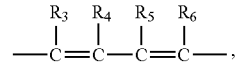

provided that at least two oxime ester groups are present in the molecule.

4. A photopolymerizable composition, comprising
(a) at least one ethylenically unsaturated photopolymerizable compound; and
(b) as photoinitiator, at least one compound of claim 1.

5. The photopolymerizable composition according to claim 4, wherein the component (a) is a resin obtained by reaction of a saturated or unsaturated polybasic acid anhydride with a product of the reaction of an epoxy resin and an unsaturated monocarboxylic acid.

6. The photopolymerizable composition according to claim 4, further comprising at least one of a further photoinitiator (c) and an additive (d).

7. The photopolymerizable composition according to claim 6, comprising, as the additive (d), a pigment or a mixture of pigments or a mixture of one or more pigments with one or more dyes.

8. The photopolymerizable composition according to claim 6, comprising, as the additive (d), a dispersant or a mixture of dispersants.

9. The photopolymerizable composition of claim 6, comprising, as the additive (d), a photosensitizer.

10. The photopolymerizable composition of claim 4, comprising 0.05 to 25% by weight of the photoinitiator (b), based on a total weight of the composition.

11. The photopolymerizable composition of claim 4, further comprising a binder polymer (e).

12. A process for photopolymerizing compounds containing ethylenically unsaturated double bonds, the process comprising irradiating the composition according to claim 4 with electromagnetic radiation in the range from 150 to 600 nm, or with electron beam or with X-rays, to form a polymer product.

13. The process of claim 12, wherein the polymer product is a component within at least one article selected from the group consisting of a pigmented paint, a nonpigmented paint, a pigmented varnish, a nonpigmented varnish, a powder coating, a printing ink, a printing plate, an adhesive, a pressure sensitive adhesive, a dental composition, a gel coat, a photoresist for electronics, an etch resist, a liquid film, a dry film, a solder resist, a resist to manufacture color filters, a resist to generate structures in the manufacturing processes of plasma-display panels, an electroluminescence display, an LCD, an article for encapsulating electrical and electronic components, an article for producing magnetic recording materials, a micromechanical part, a waveguide, an optical switch, a plating mask, a color proofing system, a glass fibre cable coating, a screen printing stencil, an article for producing three-dimensional objects by stereolithography, an image recording material for holographic recordings, a microelectronic circuit, a, decolorizing material, a formulation comprising microcapsules, a photoresist material for a UV and visible laser direct imaging system, and an article for forming dielectric layers in a sequential build-up layer of a printed circuit board.

14. A coated substrate which is coated on at least one surface with the composition according to claim 4.

15. A process for photographic production of relief images, the process comprising subjecting the coated substrate according to claim 14 to imagewise exposure and then removing unexposed portions with a developer.

16. A process for preparing the compound of claim 1, the process comprising reacting a corresponding oxime compound with an acyl halide of formula (II) or an anhydride of formula (III):

in the presence of at least one base,
wherein:
Hal is a halogen, in particular Cl, and
$R_{12}$ is hydrogen, $C_3$-$C_8$cycloalkyl, $C_2$-$C_5$alkenyl, $C_1$-$C_{20}$alkoxy or $C_1$-$C_{20}$alkyl which is unsubstituted or substituted by one or more halogen, phenyl, $C_1$-$C_{20}$alkylphenyl or CN,
or $R_{12}$ is phenyl or naphthyl, each of which is unsubstituted or substituted by one or more $C_1$-$C_6$alkyl, $C_1$-$C_4$haloalkyl, halogen, CN, $OR_{15}$, $SR_{16}$, or $NR_{17}R_{18}$,
or $R_{12}$ is $C_3$-$C_{20}$heteroaryl, benzyloxy or phenoxy, each of which is unsubstituted or substituted by one or more $C_1$-$C_6$alkyl, $C_1$-$C_4$haloalkyl and/or halogen.

17. A color filter prepared by providing red, green and blue picture elements and a black matrix, all comprising a photosensitive resin and a pigment on a transparent substrate, and providing a transparent electrode either on the surface of the substrate or on the surface of the color filter layer, wherein said photosensitive resin comprises a polyfunctional acrylate monomer, an organic polymer binder and the compound of claim 1 as a photopolymerization initiator.

18. A process comprising photopolymerization of a composition comprising at least one ethylenically unsaturated photopolymerizable compound in the presence of the composition of claim 1.

19. A compound of formula (IA):

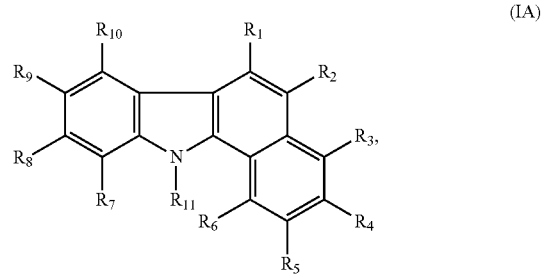

wherein $R_1$, $R_2$, $R_3$, $R_4$, $R_5$, $R_6$, $R_7$, $R_8$, $R_9$ and $R_{10}$ independently of each other are hydrogen, $C_1$-$C_{20}$alkyl,

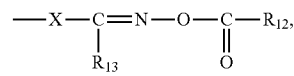

$COR_{14}$, $NO_2$, or $OR_{15}$,
provided that at least one of $R_1$, $R_2$, $R_3$, $R_4$, $R_5$, $R_6$, $R_7$, $R_8$, $R_9$, and $R_{10}$ is

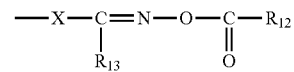

and provided that at least one of the remaining $R_1$, $R_2$, $R_3$, $R_4$, $R_5$, $R_6$, $R_7$, $R_8$, $R_9$, and $R_{10}$ is $COR_{14}$ or $NO_2$;

X is CO or a direct bond;

$R_{11}$ is $C_1$-$C_{20}$alkyl which is unsubstituted or substituted by one or more halogen, $OR_{15}$, $SR_{16}$, $COOR_{15}$, $CONR_{17}R_{18}$, $NR_{17}R_{18}$, $PO(OC_kH_{2k+1})_2$, or M, or $R_{11}$ is $C_2$-$C_{20}$alkyl which is interrupted by one or more O, CO, S, C(O)O, OC(O), phenylene, naphthylene or $NR_{19}$, wherein the interrupted $C_2$-$C_{20}$alkyl is unsubstituted or substituted by one or more halogen, $OR_{15}$, $SR_{16}$, $COOR_{15}$, $CONR_{17}R_{18}$, $NR_{17}R_{18}$ or M;

or $R_{11}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, M,

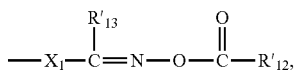

or by $C_2$-$C_{20}$alkyl which is interrupted by one or more O, S, or $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$ or $NR_{17}R_{18}$;

$R_{12}$ is hydrogen, $C_3$-$C_8$cycloalkyl, $C_2$-$C_5$alkenyl, $C_1$-$C_{20}$alkoxy or $C_1$-$C_{20}$alkyl which is unsubstituted or substituted by one or more halogen, phenyl, $C_1$-$C_{20}$alkylphenyl or CN, or $R_{12}$ is phenyl or naphthyl, each of which is unsubstituted or substituted by one or more $C_1$-$C_6$alkyl, $C_1$-$C_4$haloalkyl, halogen, CN, $OR_{15}$, $SR_{16}$, or $NR_{17}R_{18}$, or $R_{12}$ is $C_3$-$C_{20}$heteroaryl, benzyloxy or phenoxy, each of which is unsubstituted or substituted by one or more $C_1$-$C_6$alkyl, $C_1$-$C_4$haloalkyl and/or halogen;

$R_{13}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, $PO(OC_kH_{2k+1})_2$, SO—$C_1$-$C_{10}$alkyl, $SO_2$—$C_1$-$C_{10}$alkyl, M, or by $C_2$-$C_{20}$alkyl which is interrupted by one or more O, CO, S, C(O)O, OC(O), phenylene, naphthylene or by $NR_{19}$, or each of which is substituted by one or more $C_1$-$C_{20}$alkyl which is unsubstituted or substituted by one or more halogen, $COOR_{15}$, $CONR_{17}R_{18}$, phenyl, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $OR_{15}$, $SR_{16}$, $NR_{17}R_{18}$ or by M, or $R_{13}$ is $C_1$-$C_{20}$alkyl which is unsubstituted or substituted by one or more halogen, $OR_{15}$, $SR_{16}$, $C_3$-$C_8$cycloalkyl, $C_3$-$C_{20}$heteroaryl, $C_6$-$C_{20}$aryloxycarbonyl, $C_3$-$C_{20}$heteroaryloxycarbonyl, $NR_{17}R_{18}$, $COOR_{15}$, $CONR_{17}R_{18}$, $PO(OC_kH_{2k+1})_2$,

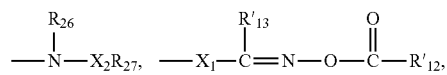

phenyl or by M, or $R_{13}$ is $C_1$-$C_{20}$alkyl which is substituted by phenyl which is substituted by one or more halogen, $C_1$-$C_{20}$alkyl, $C_1$-$C_4$haloalkyl, $OR_{15}$, $SR_{16}$ or by $NR_{17}R_{18}$, or $R_{13}$ is $C_2$-$C_{20}$alkyl which is interrupted by one or more O, CO, S, C(O)O, OC(O), phenylene, naphthylene, or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, M, or by phenyl which is substituted by $OR_{15}$, $SR_{16}$ or $NR_{17}R_{18}$, or $R_{13}$ is CN, $CONR_{17}R_{18}$, $NO_2$, $C_1$-$C_4$haloalkyl, $S(O)_m$—$C_1$-$C_6$alkyl; $S(O)_m$-phenyl which is unsubstituted or substituted by $C_1$-$C_{12}$alkyl or $SO_2$—$C_1$-$C_6$alkyl, or $R_{13}$ is $SO_2O$-phenyl which is unsubstituted or substituted by $C_1$-$C_{12}$alkyl; or is diphenyl phosphinoyl or di-($C_1$-$C_4$alkoxy)-phosphinoyl;

M is

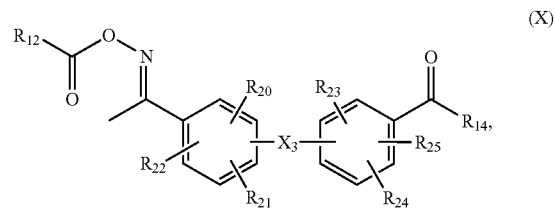

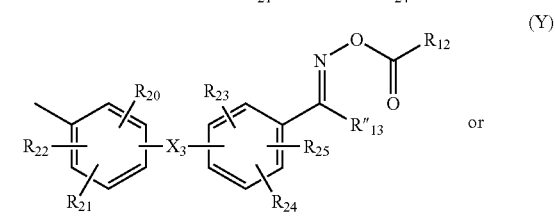

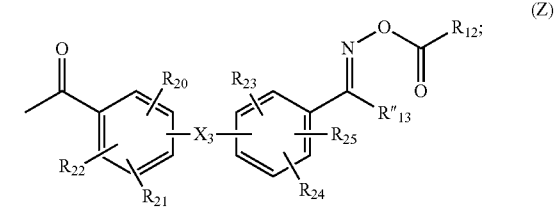

k is an integer 1-10;

m is 1 or 2;

$R'_{12}$ has one of the meanings as given for $R_{12}$;

$R'_{13}$ has one of the meanings as given for $R_{13}$;

$R''_{13}$ is $C_1$-$C_{20}$alkyl which is unsubstituted or substituted by phenyl or by phenyl which is substituted by halogen, $C_1$-$C_{20}$alkyl, $C_1$-$C_4$haloalkyl, $OR_{15}$, $SR_{16}$ or by $NR_{17}R_{18}$, or $R''_{13}$ is $C_2$-$C_{20}$alkyl which is interrupted by one or more O, CO, S, C(O)O, OC(O), phenylene, naphthylene or $NR_{19}$, wherein the interrupted $C_2$-$C_{20}$alkyl is unsubstituted or substituted by one or more halogen, $OR_{15}$, $COOR_{15}$, $CONR_{17}R_{18}$, phenyl, or by phenyl which is substituted by $OR_{15}$, $SR_{16}$ or $NR_{17}R_{18}$, or $R''_{13}$ is CN, $CONR_{17}R_{18}$, $NO_2$, $C_1$-$C_4$haloalkyl, $S(O)_m$—$C_1$-$C_6$alkyl; $S(O)_m$-phenyl which is unsubstituted or substituted by $C_1$-$C_{12}$alkyl or $SO_2$—$C_1$-$C_6$alkyl, or $R''_{13}$ is $SO_2O$-phenyl which is unsubstituted or substituted by $C_1$-$C_{12}$alkyl; or is diphenyl phosphinoyl or di-($C_1$-$C_4$alkoxy)-phosphinoyl, or $R''_{13}$ is $C_6$-$C_{20}$aryl or $C_3$-$C_{20}$heteroaryl each of which is unsubstituted or substituted by one or more phenyl, halogen, $C_1$-$C_4$haloalkyl, CN, $NO_2$, $OR_{15}$, $SR_{16}$, $NR_{17}R_{18}$, $PO(OC_kH_{2k+1})_2$, SO—$C_1$-$C_{10}$alkyl, $SO_2$—$C_1$-$C_{10}$alkyl, or by $C_2$-$C_{20}$alkyl which is interrupted by one or more O, CO, S, C(O)O, OC(O), phenylene, naphthylene or by NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or by NR$_{17}$R$_{18}$;

X$_1$ is O, CO, S or a direct bond;
X$_2$ is O, S, SO or SO$_2$;
X$_3$ is O, S or NR$_{19}$;
R$_{14}$ is C$_6$-C$_{20}$aryl or C$_3$-C$_{20}$heteroaryl each of which is unsubstituted or substituted by one or more phenyl, halogen, C$_1$-C$_4$haloalkyl, CN, NO$_2$, OR$_{15}$, SR$_{16}$, NR$_{17}$R$_{18}$, or by C$_2$-C$_{20}$alkyl which is interrupted by one or more O, S, or NR$_{19}$, or each of which is substituted by one or more C$_1$-C$_{20}$alkyl which is unsubstituted or substituted by one or more halogen, COOR$_{15}$, CONR$_{17}$R$_{18}$, phenyl, C$_3$-C$_8$cycloalkyl, C$_3$-C$_{20}$heteroaryl, C$_6$-C$_{20}$aryloxycarbonyl, C$_3$-C$_{20}$heteroaryloxycarbonyl, OR$_{15}$, SR$_{16}$ or NR$_{17}$R$_{18}$,
or R$_{14}$ is

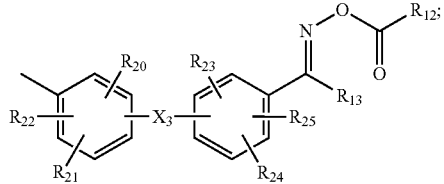

R$_{15}$ is hydrogen, phenyl-C$_1$-C$_3$alkyl, C$_1$-C$_{20}$alkyl which is unsubstituted or substituted by one or more halogen, OH, SH, CN, C$_3$-C$_6$alkenoxy, OCH$_2$CH$_2$CN, OCH$_2$CH$_2$(CO)O(C$_1$-C$_4$alkyl), O(CO)—(C$_1$-C$_4$alkyl), O(CO)—(C$_2$-C$_4$)alkenyl, O(CO)-phenyl, (CO)OH, (CO)O(C$_1$-C$_4$alkyl), C$_3$-C$_{20}$cycloalkyl, SO$_2$—(C$_1$-C$_4$haloalkyl), O(C$_1$-C$_4$haloalkyl), O(C$_1$-C$_{20}$arylene)-M, or by C$_3$-C$_{20}$cycloalkyl which is interrupted by one or more O,
or R$_{15}$ is C$_2$-C$_{20}$alkyl which is interrupted by one or more O, S or NR$_{19}$, which interrupted C$_2$-C$_{20}$alkyl is unsubstituted or substituted by O—C$_6$-C$_{20}$arylene-M,
or R$_{15}$ is (CH$_2$CH$_2$O)$_{n+1}$H, (CH$_2$CH$_2$O)$_n$(CO)—(C$_1$-C$_8$alkyl), C$_1$-C$_8$alkanoyl, C$_2$-C$_{12}$alkenyl, C$_3$-C$_6$alkenoyl or C$_3$-C$_{20}$cycloalkyl which is uninterrupted or interrupted by one or more O, S, CO or NR$_{19}$,
or R$_{15}$ is C$_1$-C$_8$alkyl-C$_3$-C$_{10}$cycloalkyl which is uninterrupted or interrupted by one or more O,
or R$_{15}$ is benzoyl which is unsubstituted or substituted by one or more C$_1$-C$_6$alkyl, halogen, OH or C$_1$-C$_3$alkoxy,
or R$_{15}$ is phenyl, naphthyl or C$_3$-C$_{20}$heteroaryl, each of which is unsubstituted or substituted by one or more halogen, OH, C$_1$-C$_{12}$alkyl, C$_1$-C$_{12}$alkoxy, CN, NO$_2$, phenyl-C$_1$-C$_3$alkyloxy, phenoxy, C$_1$-C$_{12}$alkylsulfanyl, phenylsulfanyl, N(C$_1$-C$_{12}$alkyl)$_2$, diphenylamino or

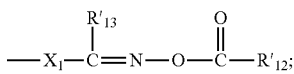

n is 1-20;
R$_{16}$ is hydrogen, C$_2$-C$_{12}$alkenyl, C$_3$-C$_{20}$cycloalkyl, or phenyl-C$_1$-C$_3$alkyl, wherein the C$_2$-C$_{12}$alkenyl, C$_3$-C$_{20}$cycloalkyl, or phenyl-C$_1$-C$_3$alkyl is uninterrupted or interrupted by one or more O, S, CO, NR$_{19}$, or R$_{16}$ is C$_1$-C$_{20}$alkyl which is unsubstituted or is substituted by one or more OH, SH, CN, C$_3$-C$_6$alkenoxy, OCH$_2$CH$_2$CN, OCH$_2$CH$_2$(CO)O(C$_1$-C$_4$alkyl), O(CO)—(C$_2$-C$_4$)alkenyl, O(CO)—(C$_1$-C$_4$alkyl), O(CO)-phenyl or COOR$_{15}$ or S—C$_6$-C$_{20}$arylene-S-M,
or R$_{16}$ is C$_2$-C$_{20}$alkyl which is interrupted by one or more O, S, CO, NR$_{19}$ which interrupted C$_2$-C$_{20}$alkyl is unsubstituted or substituted by S—C$_6$-C$_{20}$arylene-M,
or R$_{16}$ is (CH$_2$CH$_2$O)$_n$H, (CH$_2$CH$_2$O)$_n$(CO)—(C$_1$-C$_8$alkyl), C$_2$-C$_8$alkanoyl or C$_3$-C$_6$alkenoyl,
or R$_{16}$ is benzoyl which is unsubstituted or substituted by one or more C$_1$-C$_6$alkyl, halogen, OH, C$_1$-C$_4$alkoxy or C$_1$-C$_4$alkylsulfanyl,
or R$_{16}$ is phenyl, naphthyl or C$_3$-C$_{20}$heteroaryl, each of which is unsubstituted or substituted by one or more halogen, C$_1$-C$_{12}$alkyl, C$_1$-C$_4$haloalkyl, C$_1$-C$_{12}$alkoxy, CN, NO$_2$, phenyl-C$_1$-C$_3$alkyloxy, phenoxy, C$_1$-C$_{12}$alkylsulfanyl, phenylsulfanyl, N(C$_1$-C$_{12}$alkyl)$_2$, diphenylamino, (CO)O(C$_1$-C$_8$alkyl), (CO)—C$_1$-C$_8$alkyl, (CO)N(C$_1$-C$_8$alkyl)$_2$ or

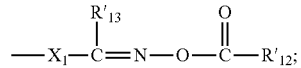

R$_{17}$ and R$_{18}$ independently of each other are hydrogen, C$_1$-C$_{20}$alkyl, C$_2$-C$_4$hydroxyalkyl, C$_2$-C$_{10}$alkoxyalkyl, C$_2$-C$_5$alkenyl, C$_3$-C$_{20}$cycloalkyl, phenyl-C$_1$-C$_3$alkyl, C$_1$-C$_8$alkanoyl, C$_1$-C$_8$alkanoyloxy, C$_3$-C$_{12}$alkenoyl, SO$_2$—(C$_1$-C$_4$haloalkyl) or benzoyl,
or R$_{17}$ and R$_{18}$ are phenyl, naphthyl or C$_3$-C$_{20}$heteroaryl, each of which is unsubstituted or substituted by one or more halogen, C$_1$-C$_4$haloalkyl, C$_1$-C$_{20}$alkoxy, C$_1$-C$_{12}$alkyl, benzoyl or C$_1$-C$_{12}$alkoxy,
or R$_{17}$ and R$_{18}$ together with the N-atom to which they are attached form a 5- or 6-membered saturated or unsaturated ring which is uninterrupted or is interrupted by O, S or NR$_{19}$, and which 5- or 6-membered saturated or unsaturated ring is unsubstituted or substituted by one or more C$_1$-C$_{20}$alkyl, C$_1$-C$_{20}$alkoxy, =O, OR$_{15}$, SR$_{16}$, NR$_{28}$R$_{29}$, COR$_{30}$, NO$_2$, halogen, C$_1$-C$_4$-haloalkyl, CN, phenyl,

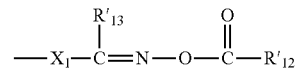

or by C$_1$-C$_{20}$cyclalkyl which is uninterrupted or is interrupted by one or more O, S, CO or NR$_{19}$,
or R$_{17}$ and R$_{18}$ together with the N-atom to which they are attached form a group

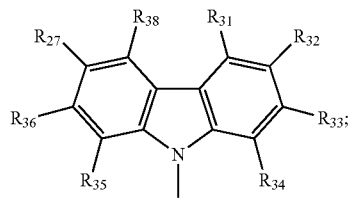

R$_{19}$ is hydrogen, C$_1$-C$_{20}$alkyl, C$_1$-C$_4$haloalkyl, C$_2$-C$_{20}$alkyl which is interrupted by one or more O, CO, C(O)O, or OC(CO), or is phenyl-$C_1$-$C_4$alkyl, $C_3$-$C_8$cycloalkyl which is uninterrupted or is interrupted by one or more O or CO, or $R_{19}$ is $COR_{30}$, or $R_{19}$ is phenyl or naphthyl both of which are unsubstituted or substituted by one or more $C_1$-$C_{20}$alkyl, halogen, $C_1$-$C_4$haloalkyl, $OR_{15}$, $SR_{16}$, $NR_{17}R_{18}$, $COR_{14}$, or

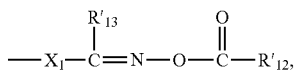

or $R_{19}$ is $C_1$-$C_6$alkylene or $C_2$-$C_6$alkenylene linked to the phenyl or naphthyl ring of the carbazole moiety and forming a 5- or 6-membered saturated or unsaturated ring;

$R_{20}$, $R_{21}$, $R_{22}$, $R_{23}$, $R_{24}$ or $R_{25}$ independently of each other are hydrogen, $COR_{14}$, $NO_2$,

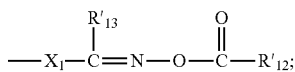

or one of $R_{21}$ and $R_{22}$, or $R_{24}$ and $R_{25}$ is

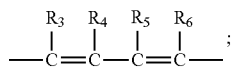

or one of $R_{20}$, $R_{21}$ or $R_{22}$ and one of $R_{23}$, $R_{24}$ or $R_{25}$ together with $X_3$ and the phenyl rings to which they are attached form a heteroaromatic ring system which is unsubstituted or substituted by one or more $C_1$-$C_{20}$alkyl, $C_1$-$C_4$haloalkyl, $C_1$-$C_{20}$alkoxy, =O, $OR_{15}$, $SR_{16}$, $NR_{17}R_{18}$, $COR_{14}$,

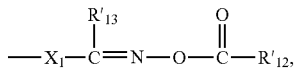

halogen, $NO_2$, CN, phenyl or by $C_3$-$C_{20}$cycloalkyl which is uninterrupted or is interrupted by one or more O, S, CO or $NR_{19}$;

$R_{26}$ is $COOR_{15}$, $CONR_{17}R_{18}$, $(CO)R_{15}$; or $R_{26}$ has one of the meanings given for $R_{17}$ and $R_{18}$;

$R_{27}$ is $COOR_{15}$, $CONR_{17}R_{18}$, $(CO)R_{15}$; or $R_{27}$ has one of the meanings given for $R_{15}$;

$R_{28}$ and $R_{29}$ independently of each other are hydrogen, $C_1$-$C_{20}$alkyl, $C_1$-$C_4$haloalkyl, $C_3$-$C_{10}$cycloalkyl or phenyl, or $R_{28}$ and $R_{29}$ together with N-atom to which they are attached form a 5- or 6-membered saturated or unsaturated ring, which is uninterrupted or interrupted by O, S or $NR_{19}$, and which 5- or 6-membered saturated or unsaturated ring is not condensed or to which 5- or 6-membered saturated or unsaturated ring a benzene ring is condensed;

$R_{30}$ is hydrogen, OH, $C_1$-$C_{20}$alkyl, $C_1$-$C_4$haloalkyl, $C_2$-$C_{20}$alkyl which is interrupted by one or more O, CO or by $NR_{19}$ or is $C_3$-$C_{20}$cycloalkyl which is uninterrupted or is interrupted by O, S, CO or $NR_{19}$, or $R_{30}$ is phenyl, naphthyl, phenyl-$C_1$-$C_4$alkyl, $OR_{15}$, $SR_{16}$ or $NR_{17}R_{18}$;

$R_{31}$, $R_{32}$, $R_{33}$, $R_{34}$, $R_{35}$, $R_{36}$, $R_{37}$ and $R_{38}$ independently of each other are hydrogen,

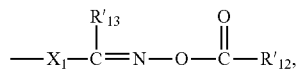

$NO_2$, $COR_{14}$, $C_1$-$C_{20}$alkyl, $C_1$-$C_4$haloalkyl, $OR_{15}$, $SR_{16}$, $NR_{17}R_{18}$, halogen, CN, phenyl or $C_3$-$C_{20}$cycloalkyl which is uninterrupted or is interrupted by one or more O, S, CO or $NR_{19}$;

or $R_{33}$ and $R_{34}$ or $R_{35}$ and $R_{36}$ or both, $R_{33}$ and $R_{34}$ and $R_{35}$ and $R_{36}$ are

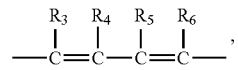

provided that at least one group

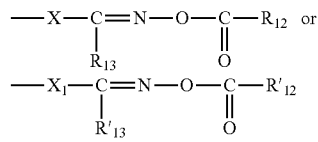

is replaced by a group

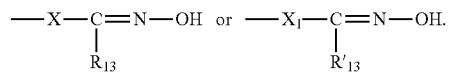

* * * * *